(12) United States Patent
Burke et al.

(10) Patent No.: US 9,328,102 B2
(45) Date of Patent: *May 3, 2016

(54) SLOW RELEASE OF ORGANOBORONIC ACIDS IN CROSS-COUPLING REACTIONS

(71) Applicant: The Board of Trustees of the University of Illinois, Urbana, IL (US)

(72) Inventors: Martin D. Burke, Champaign, IL (US); David M. Knapp, Boonville, IN (US); Eric P. Gillis, Wallingford, CT (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/686,502

(22) Filed: Apr. 14, 2015

(65) Prior Publication Data

US 2015/0246905 A1 Sep. 3, 2015

Related U.S. Application Data

(60) Division of application No. 13/669,906, filed on Nov. 6, 2012, now Pat. No. 9,006,463, which is a continuation of application No. 12/567,443, filed on Sep. 25, 2009, now Pat. No. 8,338,601.

(60) Provisional application No. 61/173,012, filed on Apr. 27, 2009, provisional application No. 61/100,441, filed on Sep. 26, 2008.

(51) Int. Cl.

| | |
|---|---|
| C07F 5/02 | (2006.01) |
| C07F 5/04 | (2006.01) |
| C07D 413/04 | (2006.01) |
| C07C 1/32 | (2006.01) |
| C07C 41/30 | (2006.01) |
| C07D 207/325 | (2006.01) |
| C07D 213/73 | (2006.01) |
| C07D 241/42 | (2006.01) |
| C07D 263/56 | (2006.01) |
| C07D 307/42 | (2006.01) |
| C07D 401/04 | (2006.01) |
| C07D 405/12 | (2006.01) |
| C07D 409/04 | (2006.01) |
| C07B 61/00 | (2006.01) |
| C07D 207/333 | (2006.01) |
| C07D 209/12 | (2006.01) |
| C07D 307/36 | (2006.01) |
| C07D 307/80 | (2006.01) |
| C07D 333/16 | (2006.01) |
| C07D 405/04 | (2006.01) |

(52) U.S. Cl.
CPC .............. *C07D 413/04* (2013.01); *C07B 61/00* (2013.01); *C07C 1/321* (2013.01); *C07C 41/30* (2013.01); *C07D 207/325* (2013.01); *C07D 207/333* (2013.01); *C07D 209/12* (2013.01); *C07D 213/73* (2013.01); *C07D 241/42* (2013.01); *C07D 263/56* (2013.01); *C07D 307/36* (2013.01); *C07D 307/42* (2013.01); *C07D 307/80* (2013.01); *C07D 333/16* (2013.01); *C07D 401/04* (2013.01); *C07D 405/04* (2013.01); *C07D 405/12* (2013.01); *C07D 409/04* (2013.01); *C07C 2101/02* (2013.01); *C07C 2531/24* (2013.01); *Y02P 20/55* (2015.11)

(58) Field of Classification Search
USPC ........................... 548/405; 558/289; 549/405
See application file for complete search history.

(56) References Cited

U.S. PATENT DOCUMENTS

| | | | |
|---|---|---|---|
| 6,096,906 A | 8/2000 | Piscopio et al. | |
| 8,013,203 B2 | 9/2011 | Burke et al. | |
| 8,338,601 B2 | 12/2012 | Burke et al. | |
| 8,754,251 B2 * | 6/2014 | Duncton et al. | ............... 558/289 |
| 9,006,463 B2 | 4/2015 | Burke et al. | |

OTHER PUBLICATIONS

Gillis, E.P., et al., "A Simple and Modular Strategy for Small Molecule Synthesis: Iterative Suzuki-Miyaura Coupling of B-Protected Haloboronic Acid Building Blocks", *J. Am. Chem. Soc.*, 129(21):6716-6717 (American Chemical Society, USA, 2007).

Kitamura, Y. et al., "Heterogeneous Pd/C-catalyzed ligand-free Suzuki-Miyaura coupling reaction using argyl boronic esters", *Tetrahedron*, 63(43):10596-10602 (Elsevier Ltd., Oct. 22, 2007).

Mancilla, T. et al., "Synthesis and characterization of (N-B) phenyl [N-alkyl-N-(2-alkyl) aminodiacetate-O, O', N] boranes and phenyl [N-alkyl-N-(2-alkyl) aminodiacetate-O, O', N] boranes", *Polyhedron*, 26:1023-1028 (Elsevier Ltd., 2006).

Stewart, S. K., et al., "Synthesis of *trans*-arylvinylboronates via a palladium catalysed cross-coupling of a vinylboronate ester with aryl halides", *J. of Organometallic Chemistry*, 482(1-2):293-300 (Elsevier Science S. A., Nov. 29, 1994).

International Search Report for PCT/US2009/058421 dated May 7, 2010.

Written Opinion for PCT/US2009/058421 dated May 7, 2010.

* cited by examiner

*Primary Examiner* — Charanjit Aulakh

(74) *Attorney, Agent, or Firm* — Alan W. Steele; Foley Hoag LLP

(57) ABSTRACT

A method of performing a chemical reaction includes reacting a compound selected from the group consisting of an organohalide and an organo-pseudohalide, and a protected organoboronic acid represented by formula (I) in a reaction mixture:

$$R^1\text{—B-T} \qquad \qquad (I);$$

where $R^1$ represents an organic group, T represents a conformationally rigid protecting group, and B represents boron having $sp^3$ hybridization. When unprotected, the corresponding organoboronic acid is unstable by the boronic acid neat stability test. The reaction mixture further includes a base having a $pK_B$ of at least 1 and a palladium catalyst. The method further includes forming a cross-coupled product in the reaction mixture.

12 Claims, 9 Drawing Sheets

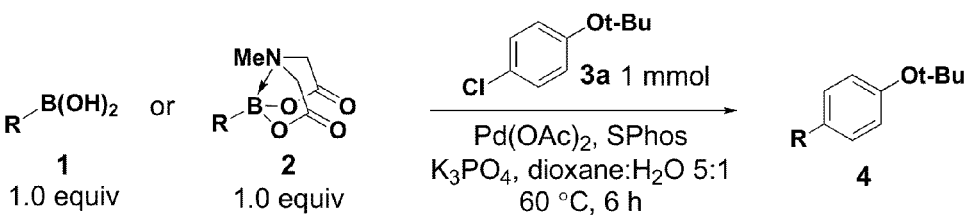

| entry | R | % remaining after benchtop storage under air[a] | | % isolated yield from cross-coupling[c] | |
| --- | --- | --- | --- | --- | --- |
| | | 1 (15 days) | 2 (60 days) | 4 | |
| | | | | 1 | 2 |
| 1 | a (furyl) | 7 | >95[b] | 4a | 68 | 94 |
| 2 | b (benzofuryl) | 88 | >95 | 4b | 50 | 92 |
| 3 | c (thienyl) | 80 | >95 | 4c | 37 | 94 |
| 4 | d (Me-bithienyl) | 80 | >95[b] | 4d | 45 | 96 |
| 5 | e (Boc-pyrrolyl) | <5 | >95 | 4e | 61 | 90 |
| 6 | f (PhO$_2$S-indolyl) | <5 | >95 | 4f | 14 | 93 |
| 7[d] | g (vinyl) | 5 | >95[b] | 4g | 79 | 98 |
| 8[d] | h (cyclopropyl) | 31 | >95 | 4h | 95 | 96 |

[a]Freshly prepared boronic acids 1 and MIDA boronates 2 were stored as solids on the benchtop under air for 15 and 60 days, respectively. [b]107 days [c]Reaction conditions: 1.0 equiv of 3a (1 mmol), 1.0 equiv of 1 (freshly prepared, >95% pure) or 1.0 equiv of 2, 5 mol % Pd(OAc)$_2$, 10 mol % SPhos, 7.5 equi. K$_3$PO$_4$, 0.07 M in dioxane:H$_2$O 5:1, 60 °C, 6 h. [d]Cross-couplings were run at 100 °C.

FIG. 2

| entry | 2 | 3 | 4 | % isolated yield |
|---|---|---|---|---|
| 1 | 2a | 3b | 4i | 99 |
| 2 | 2a | 3c | 4j | 97 |
| 3 | 2a | 3d | 4k | 99 |
| 4 | 2a | 3e | 4l | 91 |
| 5 | 2b | 3b | 4m | 94 |
| 6 | 2b | 3f | 4n | 94 |
| 7[b] | 2b | 3g | 4o | 85 |
| 8[b] | 2b | 3h | 4p | 85 |
| 9 | 2c | 3b | 4q | 98 |
| 10 | 2c | 3d | 4r | 99 |
| 11 | 2c | 3i | 4s | 97 |

[a]General reaction conditions: 1 equiv of aryl halide (1 mmol), 1.2 equiv of MIDA boronate, 5 mol % Pd(OAc)$_2$, 10 mol % SPhos, 7.5 equiv of K$_3$PO$_4$, 0.07 M in dioxane:H$_2$O 5:1, 60 °C, 6 h. [b]1.5 equiv of MIDA boronate. [c]0.5 mmol of aryl halide, 0.6 mmol of MIDA boronate (1.2 equiv). [d] 100 °C. [e]2 h. [f] 24 h.

| entry | 2 | 3 | 4 | % isolated yield |
|---|---|---|---|---|
| 12[c] | 2e (Boc-pyrrole-MIDA boronate) | 3b | 4t (Boc-pyrrole-2,4-dimethoxyphenyl) | 81 |
| 13[c] | 2e | 3d | 4u (Boc-pyrrole-2-methylbenzoxazole) | 98 |
| 14 | 2f (N-PhO₂S-indole-MIDA boronate) | 3b | 4v (N-PhO₂S-indole-2,4-dimethoxyphenyl) | 97 |
| 15 | 2f | 3d | 4w (N-PhO₂S-indole-2-methylbenzoxazole) | 93 |
| 16[d,e] | 2g (vinyl-MIDA boronate) | 3c | 4x (2,4,6-trimethylstyrene) | 91 |
| 17[d,e] | 2g | 3i | 4y (2-vinylquinoxaline) | 87 |
| 18[d,e] | 2g | 3g | 4z (5-vinyl-2-aminopyridine) | 76 |
| 19[d,e] | 2g | 3d | 4aa (5-vinyl-2-methylbenzoxazole) | 96 |
| 20[b,d,f] | 2h (cyclopropyl-MIDA boronate) | 3c | 4bb (2,4,6-trimethylcyclopropylbenzene) | 79 |
| 21[d] | 2h | 3b | 4cc (2,4-dimethoxycyclopropylbenzene) | 97 |

[a]General reaction conditions: 1 equiv of aryl halide (1 mmol), 1.2 equiv of MIDA boronate, 5 mol % Pd(OAc)₂, 10 mol % SPhos, 7.5 equiv of K₃PO₄, 0.07 M in dioxane:H₂O 5:1, 60 °C, 6 h. [b]1.5 equiv of MIDA boronate. [c]0.5 mmol of aryl halide, 0.6 mmol of MIDA boronate (1.2 equiv). [d]100 °C. [e]2 h. [f]24 h.

FIG. 9B

| Entry | MIDA boronate 2 | aryl halide | Product | | Yield |
|---|---|---|---|---|---|
| 1 | 2a | 5a | | 6a | 98 |
| 2 | 2a | 5b | | 6b | 94 |
| 3 | 2a | 5c | | 6c | 94 |
| 4 | 2b | 5a | | 6d | 98 |
| 5 | 2b | 5b | | 6e | 96 |
| 6 | 2b | 5c | | 6f | 95 |
| 7[b] | 2c | 5a | | 6g | 95 |
| 8 | 2c | 5b | | 6h | 98 |
| 9 | 2c | 5c | | 6i | 88 |
| 10 | 2d | 5d | | 6j | 89 |
| 11 | 2j | 5a | | 6k | 99 |
| 12 | 2j | 5b | | 6l | 99 |
| 13 | 2j | 5c | | 6m | 91 |
| 14 | 2g | 5a | | 6n | 95 |
| 15[b] | 2g | 5a | | 6n | 93 |
| 16 | 2g | 5b | | 6o | 92 |
| 17 | 2g | 3j | | 6n | 97 |
| 18 | 2g | 5e | | 6p | 84 |
| 19[c] | 2h | 5a | | 6q | 93 |

[a]Reaction conditions: 1 equiv of aryl halide (1 mmol), 1.5 equiv of MIDA boronate, 2 mol % Pd(OAc)$_2$, 4 mol % SPhos, 7.5 equiv of K$_3$PO$_4$. [b]Pd(PPh$_3$)$_4$ was used instead of Pd(OAc)$_2$/SPhos. [c]PdCl$_2$dppf was used instead of Pd(OAc)$_2$/SPhos, 85 °C.

FIG. 11

SLOW RELEASE OF ORGANOBORONIC ACIDS IN CROSS-COUPLING REACTIONS

REFERENCE TO RELATED APPLICATIONS

This application is a divisional of U.S. patent application Ser. No.13/669,906, filed Nov. 6, 2012, now U.S. Pat. No. 9,006,463, which is a continuation of U.S. patent application. Ser. No. 12/567,443, filed Sep. 25, 2009, now U.S. Pat. No. 8,338,601, which claims the benefit of U.S. Provisional Application No. 61/100,441 entitled "Slow Release of Boronic Acids in Cross-Coupling Reactions" filed Sep. 26, 2008, and claims the benefit of U.S. Provisional Application No. 61/173,012 entitled "Slow Release of Organoboronic Acids in Cross-Coupling Reactions" filed Apr. 27, 2009. Each of the above-referenced applications is incorporated by reference in its entirety.

FEDERALLY SPONSORED RESEARCH OR DEVELOPMENT

The subject matter of this application may have been funded in part under a research grant from the National Science Foundation under Grant Number Career 0747778, and under a research grant from the National Institutes of Health under Chemical Biology Interface Training Number 1-492576-510000-191788. The U.S. Government may have rights in this invention.

BACKGROUND

The Suzuki-Miyaura reaction is a palladium- or nickel-catalyzed cross coupling between a boronic acid or a boronic ester, and an organohalide or an organo-pseudohalide. (Miyaura, A. *Chem. Rev.*, 1995) This cross coupling transformation is a powerful method for C—C bond formation in complex molecule synthesis. The reaction is tolerant of functional groups, and has become increasingly general and widespread in its use for coupling of organic compounds. (Barder, 2005; Billingsley, 2007; Littke, 2000; Nicolaou, 2005)

Organoboronic acids are notoriously sensitive to many common reagents. (Hall, 2005; Tyrell, 2003) It is therefore typical to introduce the boronic acid functional group during the last step of a building block synthesis. However, many of the methods for doing so (hydroboration, trapping organometallic reagents with trimethylborate, etc.) are intolerant to a variety of common functional groups, such as alcohols, aldehydes, ketones, alkynes and olefins. This makes the synthesis of structurally complex organoboronic acid building blocks quite challenging.

One area of research on the Suzuki-Miyaura reaction is the development of protecting groups for the boronic acid functional group. A compound that includes a protected boronic acid group and another functional group can undergo chemical transformations of the other functional group without chemically transforming the boron. Removal of the protecting group (deprotection) then provides the free boronic acid group, which can undergo a Suzuki-Miyaura reaction to cross-couple the compound with an organohalide or an organo-pseudohalide.

In one example of a boronic acid protecting group, each of the two B—OH groups is converted into a boronic ester group (>B—O—R) or a boronic amide group (>B—NH—R), where R is an organic group. The organic group can be removed by hydrolysis to provide the free boronic acid group. (Deng, 2002; Hohn, 2004; Holmes, 2006; Noguchi, 2007) The heteroatom boron bonds in these protected compounds tend to be very strong, however. The relatively harsh conditions required for cleaving these ligands typically are incompatible with complex molecule synthesis. In another example of a boronic acid protecting group, three organoboronic acid molecules can be condensed to form a cyclic boroxine. (Kerins, 2002) These protected organoboronic acids, however, tend to be unstable to long term storage.

The reactivity of a boronic acid group also may be decreased by conversion of the boronic acid group into a tetracoordinate anion, such as $[R-BF_3]^-$, where R represents an organic group. These anions may be present as salts with a counterion, such as $K^+$ or $Na^+$. (Molander, 2007) Another class of tetracoordinate boron anions, $[R-B(OH)_3]^-$, has been reported in the context of purifying organoboronic acids for use in the Suzuki-Miyaura reaction. (Cammidge, 2006) In each of these systems, the boron itself is not protected from the Suzuki-Miyaura reaction, but can be used directly in the coupling transformation.

Recently, it was discovered that N-methyliminodiacetic acid (MIDA) boronates can be used to protect boronic acid functional groups from a variety of chemical reactions. (Gillis, 2007; Lee, 2008) These MIDA boronates are stable to air and to purification by chromatography, and do not cross-couple under anhydrous conditions. However, the MIDA boronates can be hydrolyzed rapidly with aqueous NaOH (<10 minutes at 23° C.) to release the corresponding unprotected organoboronic acid. Thus, MIDA boronates can be used as convenient surrogates for stable organoboronic acids under aqueous NaOH-promoted Suzuki-Miyaura coupling conditions. This approach has been shown to be effective for both aryl- and alkenyl-MIDA boronates. The only change to the standard coupling protocol is the inclusion of extra base to hydrolyze the MIDA boronate. The cleaved $MIDA^{2-}$ ion appears to have no deleterious effect on these reactions, even though it is known to be a ligand for Pd(II).

The published synthetic methods for protection of organoboronic acids as MIDA boronates have been less successful when used to protect unstable organoboronic acids. Unstable organoboronic acids are susceptible to degradation, which can preclude their benchtop storage and/or their efficient cross-coupling. When MIDA boronates of unstable boronic acids are simultaneously deprotected and reacted with an organohalide or organopsuedohalide under NaOH-promoted Suzuki-Miyaura coupling conditions, the yield of cross-coupled product can be undesirably low. Examples of unstable organoboronic acids include 2-heterocyclic boronic acids (Billingsley, 2007; Tyrrell, 2003), vinyl boronic acids (Matteson, 1960), and cyclopropyl boronic acids (Wallace, 2002). Although unstable organoboronic acids can be successfully prepared and stored in the form of their corresponding MIDA boronates, the deprotected organoboronic acids may be susceptible to degradation during their subsequent use.

It would be desirable to perform high yield cross-coupling reactions using MIDA boronates of unstable organoboronic acids. Preferably the cross-coupling would be as selective and as tolerant of functional groups as a conventional cross-coupling reaction. It would also be desirable for such a reaction to be efficient and simple.

SUMMARY

In one aspect, the invention provides a method of performing a chemical reaction, which includes reacting in a reaction mixture a compound selected from the group consisting of an organohalide and an organo-pseudohalide, and a protected organoboronic acid represented by formula (I):

$$R^1—B-T \qquad (I),$$

where $R^1$ represents an organic group, T represents a conformationally rigid protecting group, B represents boron having $sp^3$ hybridization, and a corresponding unprotected organoboronic acid is unstable by the boronic acid neat stability test. The reaction mixture further includes a base having a $pK_B$ of at least 1 and a palladium catalyst. The method further includes forming a cross-coupled product in the reaction mixture.

In another aspect, the invention provides a method of performing a chemical reaction, which includes deprotecting in a reaction mixture a protected organoboronic acid represented by formula (I):

$$R^1—B-T \qquad (I),$$

where $R^1$ represents an organic group, B represents boron having $sp^3$ hybridization, T represents a conformationally rigid protecting group, and the reaction mixture further includes a base and a palladium catalyst; to form a corresponding unprotected organoboronic acid that is unstable by the boronic acid neat stability test. The method further includes reacting in the reaction mixture the unprotected organoboronic acid and a compound selected from the group consisting of an organohalide and an organo-pseudohalide; and forming a cross-coupled product in the reaction mixture. The time required for at least 90% of the protected organoboronic acid to be deprotected in the reaction mixture is at least equal to the time required for 90% of the cross-coupled product to be formed in the reaction mixture.

In another aspect, the invention provides a method of performing a chemical reaction, which includes reacting in a reaction mixture a compound selected from the group consisting of an organohalide and an organo-pseudohalide, and a protected organoboronic acid represented by formula (I):

$$R^1—B-T \qquad (I),$$

where $R^1$ represents a 2-pyridyl group, T represents a conformationally rigid protecting group, and B represents boron having $sp^3$ hybridization. The reaction mixture further includes a protic solvent, a base having a $pK_B$ of at least 1, and a palladium catalyst. The method further includes forming a cross-coupled product in the reaction mixture.

The following definitions are included to provide a clear and consistent understanding of the specification and claims.

The term "organoboronic acid" means a compound represented by formula (II):

$$R^1—B(OH)_2 \qquad (II),$$

where $R^1$ is an organic group that is bonded to the boron through a boron-carbon bond.

The term "group" means a linked collection of atoms or a single atom within a molecular entity, where a molecular entity is any constitutionally or isotopically distinct atom, molecule, ion, ion pair, radical, radical ion, complex, conformer etc., identifiable as a separately distinguishable entity. The description of a group as being "formed by" a particular chemical transformation does not imply that this chemical transformation is involved in making the molecular entity that includes the group.

The term "organic group" means a group containing at least one carbon atom.

The term "protected organoboronic acid" means a chemical transform of an organoboronic acid, in which the boron has a lower chemical reactivity relative to the original organoboronic acid.

The term "chemical transform" of a substance means a product of a chemical transformation of the substance, where the product has a chemical structure different from that of the substance. A chemical transform of a substance may or may not actually be formed from the substance.

The term "chemical transformation" means the conversion of a substance into a product, irrespective of reagents or mechanisms involved.

The term "$sp^3$ hybridization" means that an atom is bonded and/or coordinated in a configuration having a tetrahedral character of at least 50%. For tetracoordinate boron atoms, the tetrahedral character of the boron atom is calculated by the method of Hopfl, H., *J. Organomet. Chem.* 581, 129-149, 1999. In this method, the tetrahedral character is defined as:

$$THC_{DA} [\%]=100\times[1-(\Sigma_{n=1-6}|109.5-\theta_n|°/90°)]$$

where $\theta_n$ is one of the six bond angles of the boron atom.

The term "protecting group" means an organic group bonded to at least one atom, where the atom has a lower chemical activity than when it is not bonded to the protecting group. For boron containing compounds, the term excludes non-organic groups used to lower the chemical activity of the boron, such as the $F^-$ and $OH^-$ ligands of $—BF_3^-$ and $—B(OH)_3^-$.

The term "conformationally rigid protecting group" means an organic protecting group that, when bonded to a boron atom, is determined to be conformationally rigid by the "conformational rigidity test".

The term "alkyl group" means a group formed by removing a hydrogen from a carbon of an alkane, where an alkane is an acyclic or cyclic compound consisting entirely of hydrogen atoms and saturated carbon atoms. An alkyl group may include one or more substituent groups.

The term "heteroalkyl group" means a group formed by removing a hydrogen from a carbon of a heteroalkane, where a heteroalkane is an acyclic or cyclic compound consisting entirely of hydrogen atoms, saturated carbon atoms, and one or more heteroatoms. A heteroalkyl group may include one or more substituent groups.

The term "alkenyl group" means a group formed by removing a hydrogen from a carbon of an alkene, where an alkene is an acyclic or cyclic compound consisting entirely of hydrogen atoms and carbon atoms, and including at least one carbon-carbon double bond. An alkenyl group may include one or more substituent groups.

The term "heteroalkenyl group" means a group formed by removing a hydrogen from a carbon of a heteroalkene, where a heteroalkene is an acyclic or cyclic compound consisting entirely of hydrogen atoms, carbon atoms and one or more heteroatoms, and including at least one carbon-carbon double bond. A heteroalkenyl group may include one or more substituent groups.

The term "alkynyl group" means a group formed by removing a hydrogen from a carbon of an alkyne, where an alkyne is an acyclic or cyclic compound consisting entirely of hydrogen atoms and carbon atoms, and including at least one carbon-carbon triple bond. An alkynyl group may include one or more substituent groups.

The term "heteroalkynyl group" means a group formed by removing a hydrogen from a carbon of a heteroalkyne, where a heteroalkyne is an acyclic or cyclic compound consisting entirely of hydrogen atoms, carbon atoms and one or more heteroatoms, and including at least one carbon-carbon triple bond. A heteroalkynyl group may include one or more substituent groups.

The term "aryl group" means a group formed by removing a hydrogen from a ring carbon atom of an aromatic hydrocarbon. An aryl group may by monocyclic or polycyclic and may include one or more substituent groups.

The term "heteroaryl group" means a group formed by replacing one or more methine (—C≡) and/or vinylene (—CH═CH—) groups in an aryl group with a trivalent or divalent heteroatom, respectively. A heteroaryl group may by monocyclic or polycyclic and may include one or more substituent groups.

The term "heterocyclic group" means a group formed by removing a hydrogen from a carbon of a heterocycle, where a heterocycle is a cyclic compound consisting entirely of hydrogen atoms, saturated carbon atoms, and one or more heteroatoms. A heterocyclic group may include one or more substituent groups. Heterocyclic groups include cyclic heteroalkyl groups, cyclic heteroalkenyl groups, cyclic heteroalkynyl groups and heteroaryl groups. A 2-heterocyclic groups is a heterocyclic group containing a heteroatom at the 2-position in the ring.

The term "substituent group" means a group that replaces one or more hydrogen atoms in a molecular entity.

The term "halogen group" means —F, —Cl, —Br or —I.

The term "organohalide" means an organic compound that includes at least one halogen group.

The term "haloorganoboronic acid" means an organoboronic acid in which the organic group bonded to the boron through a boron-carbon bond includes a halogen group or a pseudohalogen group.

The term "pseudohalogen group" means a group that has chemical reactivity similar to that of a halogen group. Examples of pseudohalogen groups include triflate (—O—S(═O)$_2$—CF$_3$), methanesulfonate (—O—S(═O)$_2$—CH$_3$), cyanate (—C≡N), azide (—N$_3$) thiocyanate (—N═C═S), thioether (—S—R), anhydride (—C(═O)—O—C(═O)—R), and phenyl selenide (—Se—C$_6$H$_5$).

The term "organo-pseudohalide" means an organic compound that includes at least one pseudohalogen group.

BRIEF DESCRIPTION OF THE DRAWINGS

The invention can be better understood with reference to the following drawings and description. The components in the figures are not necessarily to scale and are not intended to accurately represent molecules or their interactions, emphasis instead being placed upon illustrating the principles of the invention.

FIG. 2 represents chemical structures, reaction schemes and product yields for examples of reactions of protected organoboronic acids and of unprotected organoboronic acids in cross-coupling reactions.

FIG. 4 depicts a graph of the cross-coupling conversion of 2-furyl boronic acid 1a with 1-tert-butoxy-4-chlorobenzene 3a.

FIGS. 9A and 9B include chemical structures, reaction schemes and product yields for cross-coupling reactions of a variety of MIDA boronates with a variety of aryl chlorides.

FIG. 11 includes chemical structures, reaction schemes and product yields for cross-coupling reactions of a variety of MIDA boronates with a variety of aryl bromides and aryl chlorides.

DETAILED DESCRIPTION

In accordance with the present invention, an efficient chemical transformation of an unstable organoboronic acid can be accomplished by simultaneously deprotecting a protected MIDA boronate to form an unprotected boronic acid, and cross-coupling the unprotected boronic acid with an organohalide or an organo-pseudohalide. In one example of this chemical reaction, the MIDA boronate is reacted with an organohalide or an organo-pseudohalide in a reaction mixture that includes a base and a palladium catalyst. The rate of the deprotection of the protected boronate is at most equal to the rate of formation of the cross-coupled product.

The base used to simultaneously deprotect the MIDA boronate and promote the cross-coupling reaction may be a mild base. Deprotection of MIDA boronates with a mild base can provide a slower release of the unprotected organoboronic acid into the reaction mixture than that provided through deprotection with a strong base. This slower release can allow cross-coupling to occur between an organohalide or an organo-pseudohalide and an organoboronic acid that would otherwise degrade during the reaction. This slower release also can allow cross-coupling to occur with organoboronic acids that cannot be prepared or isolated in pure form.

Figure 1:
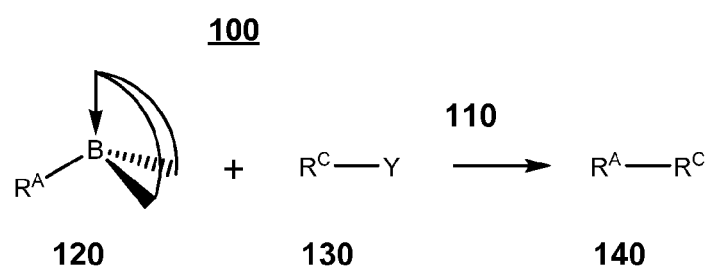
FIG. 1 represents a method of performing a chemical reaction.

FIG. 1 represents a method 100 of performing a chemical reaction, including reacting 110 a protected organoboronic acid 120 and an organohalide or organo-pseudohalide 130, to provide a cross-coupled product 140. R$^A$ and R$^C$ independently are organic groups, and Y is a halogen group or a pseudohalogen group. The reacting 110 may include contacting the protected organoboronic acid 120 and the organohalide or organo-pseudohalide 130 with a palladium catalyst in the presence of a mild base, such as a base having a pK$_B$ of at least 1. The protecting group may be removed from the boron atom in situ, providing a corresponding unprotected organoboronic acid, which can then cross-couple with the organohalide or organo-pseudohalide 130. The protected organoboronic acid 120 includes a boron having an sp$^3$ hybridization and a conformationally rigid protecting group, and the organic group R$^A$ is bonded to the boron through a B—C bond. Preferably the protected organoboronic acid 120 includes a trivalent protecting group bonded to the boron.

A method of performing a chemical reaction includes reacting a compound selected from the group consisting of an organohalide and an organo-pseudohalide, and a protected organoboronic acid represented by formula (I) in a reaction mixture:

R$^1$—B-T              (I);

where R$^1$ represents an organic group, T represents a conformationally rigid protecting group, and B represents boron having sp$^3$ hybridization. When unprotected, the corresponding organoboronic acid is unstable by the boronic acid neat stability test. The reaction mixture also includes a base having a pK$_B$ of at least 1 and a palladium catalyst. The method further includes forming a cross-coupled product in the reaction mixture. The corresponding unprotected organoboronic acid may be represented by formula (II):

R$^1$—B(OH)$_2$              (II), where $R^1$ represents $R^1$ from formula (I), and B represents boron having $sp^2$ hybridization.

The $R^1$ group is bonded to the boron through a B—C bond. The $R^1$ group may be an alkyl group, a heteroalkyl group, an alkenyl group, a heteroalkenyl group, an alkynyl group, a heteroalkynyl group, an aryl group, a heteroaryl group, or a combination of at least two of these groups. Moreover, $R^1$ may include one or more substituent groups, which may include a heteroatom bonded to a carbon of the alkyl, heteroalkyl, alkenyl, heteroalkenyl, alkynyl, heteroalkynyl, aryl, and/or heteroaryl group.

The $R^1$ group may include one or more functional groups. Examples of functional groups that may be present as part of $R^1$ include halogen or pseudohalogen (—X), alcohol (—OH), aldehyde (—CH═O), ketone (>C(═O)), carboxylic acid (—C(═O)OH), thiol (—SH), sulfone, sulfoxide, amine, phosphine, phosphite, phosphate, and combinations of these. Moreover, examples of functional groups that may be present as part of $R^1$ include metal-containing groups, such as groups that contain metals such as tin (Sn), zinc (Zn), silicon (Si), boron, and combinations of these.

Examples of functional groups that may be present as part of $R^1$ include protected alcohols, such as alcohols protected as silyl ethers, for example trimethylsilyl ether (TMS), t-butyldiphenylsilyl ether (TBDPS), t-butyldimethylsilyl ether (TBDMS), triisopropylsilyl ether (TIPS); alcohols protected as alkyl ethers, for example methoxymethyl ether (MOM), methoxyethoxymethyl ether (MEM), p-methoxybenzyl ether (PMB), tetrahydropyranyl ether (THP), methylthiomethyl ether; and alcohols protected as carbonyl groups, such as acetate or pivaloylate. Examples of functional groups that may be present as part of $R^1$ include protected carboxylic acids, such as carboxylic acids protected as esters, for example methyl ester, t-butyl ester, benzyl ester and silyl ester. Examples of functional groups that may be present as part of $R^1$ include protected amines, such as amines protected as carbamates, for example N-(trimethyl-silyl)-ethoxycarbamate (Teoc), 9-fluorenylmethyl carbamate (FMOC), benzylcarbamate (CBZ), t-butoxycarbamate (t-BOC); and amines protected as benzylamines.

In another example, the R' group may be represented by formula (III):

$$Y—R^2—(R^3)_m— \qquad (III),$$

where Y represents a halogen group or a pseudohalogen group; $R^2$ represents an aryl group or a heteroaryl group; $R^3$ represents an alkyl group, a heteroalkyl group, an alkenyl group, a heteroalkenyl group, an alkynyl group, a heteroalkynyl group, an aryl group, a heteroaryl group, or a combination of at least two of these groups; and m is 0 or 1. $R^2$ may be, for example, a heteroaryl group. Moreover, $R^2$ and $R^3$ independently may include one or more substituent groups, which may include a heteroatom bonded to a carbon of the $R^2$ or $R^3$ group. The $R^2$ and $R^3$ groups independently also may include one or more functional groups, as described for $R^1$ above. In one example, m is 1, and $R^3$ includes a 2-heterocyclic group.

Preferably the $R^1$ group is a 2-heterocyclic group, a vinyl group, or a cyclopropyl group. More preferably the $R^1$ group is a 2-heterocyclic group or a vinyl group. More preferably the $R^1$ group is a 2-heterocyclic group. More preferably the $R^1$ group is a 2-furyl group, a 2-benzofuryl group, a 2-thiophenyl group, a 4-(4'-methylthiophene)-thiophenyl group, a 2-(N-butoxycarbonyl-pyrollyl) group, a 2-(N-phenylsulfonate-indolyl) group, or a 2-pyridyl group. These groups independently also may include one or more substituent groups, which may include a heteroatom bonded to a carbon of the 2-heterocyclic group, the vinyl group, or the cyclopropyl group. Substituent groups, if present, may include one or more functional groups.

For the protected organoboronic acid of formula (I), when $R^1$ is represented by formula (III), the protected organoboronic acid is a protected haloorganoboronic acid or pseudohaloorganoboronic acid. The Y— group may undergo Suzuki-Miyaura cross-coupling with another compound that includes a free boronic acid group, without reaction of the boron of the protected organoboronic acid. Deprotection of the boron provides the free boronic acid group, which may then undergo Suzuki-Miyaura cross-coupling with another compound that includes a halogen group or a pseudohalogen group. These protected haloorganoboronic acids thus may be used as bifunctional building blocks for iterative synthesis through selective Suzuki-Miyaura transformations.

In formula (I), the T group represents a conformationally rigid protecting group bonded to the boron. Conformationally rigid protecting groups for boron are described, for example, in copending U.S. patent application Ser. No. 11/937,338, entitled "System For Controlling the Reactivity of Boronic Acids", with inventors Martin D. Burke et al., published as US 20090030238, which is incorporated herein by reference. Conformational rigidity of an organic protecting group bonded to a boron atom is determined by the following "conformational rigidity test". A 10 mg sample of a compound including a boron atom and an organic protecting group bonded to the boron is dissolved in dry $d_6$-DMSO and transferred to an NMR tube. The sample is then analyzed by $^1$H-NMR at temperatures ranging from 23° C. to 150° C. At each temperature, the sample shim is optimized, and a $^1$H-NMR spectrum obtained. If the protecting group is not conformationally rigid, then split peaks for a set of diastereotopic protons in the $^1$H-NMR spectrum obtained at 23° C. will coalesce into a single peak in the $^1$H-NMR spectrum obtained at 100° C. If the protecting group is conformationally rigid, then split peaks for a set of diastereotopic protons in the $^1$H-NMR spectrum obtained at 23° C. will remain split, and will not coalesce into a single peak in the $^1$H-NMR spectrum obtained at 90° C.

In one example of a protected organoboronic acid that includes a conformationally rigid protecting group bonded to the boron, a protected organoboronic acid may be represented by formula (IV):

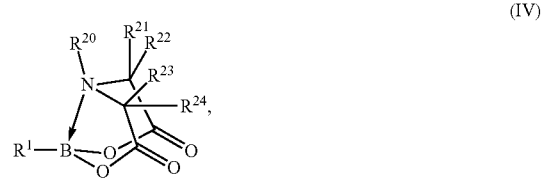

where $R^1$ represents an organic group, B represents a boron having $sp^3$ hybridization, and $R^{20}$, $R^{21}$, $R^{22}$, $R^{23}$ and $R^{24}$ independently are a hydrogen group or an organic group. $R^{20}$, $R^{21}$, $R^{22}$, $R^{23}$ and $R^{24}$ independently may be an alkyl group, a heteroalkyl group, an alkenyl group, a heteroalkenyl group, an alkynyl group, a heteroalkynyl group, an aryl group, a heteroaryl group, or a combination of at least two of these groups. In one example, $R^{20}$ is methyl, and each of $R^{21}$, $R^{22}$, $R^{23}$ and $R^{24}$ is hydrogen. The protected organoboronic acid of this example may be represented by formula (V):

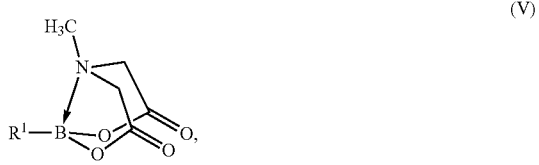

where $R^1$ represents the organic group, and B represents the boron having sp$^3$ hybridization. The $R^1$ group of formulas (IV) and (V) is as described above for $R^1$ of formulas (I) and (II).

Protected organoboronic acids according to formula (IV) may be prepared by reaction of an appropriate imino-di-carboxylic acid with the corresponding unprotected organoboronic acid (II), as illustrated in the following reaction scheme:

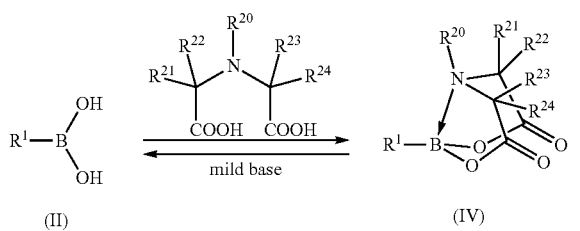

If $R^{20}$ is an organic group, the imino-di-carboxylic acid is an N-substituted imino-di-carboxylic acid. In a specific example, protected organoboronic acids according to formula (V) may be prepared by reaction of N-methyliminodiacetic acid (MIDA) with the corresponding unprotected organoboronic acid (II), as illustrated in the following reaction scheme:

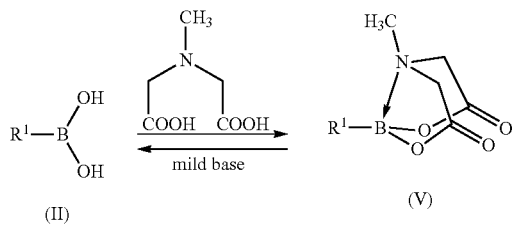

In each case, the protected organoboronic acid may be deprotected by contact with a mild base, to provide the free organoboronic acid (II).

Protected organoboronic acids according to formula (IV) also may be prepared without using an isolated organoboronic acid as a reactant. The organoboronic acid may be formed in situ, just prior to its conversion to a protected organoboronic acid. For example, the organoboronic acid may be produced in situ by hydrolysis of a boronate ester (i.e. $R^1$—B—(OR')(OR"), R' and R" are organic groups). The boronate ester may be formed, for example, by addition of HB(OR')(OR") across the C—C multiple bond of an alkene or an alkyne. (Brown, 1972) The boronate ester also may be formed by a Miyaura borylation (Miyaura, 1997; Miyaura, JOC, 1995); by reaction of an organohalide with an organolithium reagent, followed by reaction with boronate triester (i.e. B(OR)$_3$); or by reaction of a boronate triester with an organometal reagent (i.e. R—Li, R—Mg, R—Zn; Brown, 1983). In another example, the organoboronic acid may be produced in situ by treatment of a tri-substituted borane (i.e. $R^1$—BR'R") with acetaldehyde (R' and R" are organic groups). The tri-substituted borane may be formed, for example, by hydroborylation of an alkene or an alkyne with HBR'R", to add the HBR'R" across the C—C multiple bond.

Protected organoboronic acids also may be formed without ever forming the free organoboronic acid. For example, a boronic halide (VI) may be reacted with a diacid or its corresponding salt to provide protected organoboronic acid (IV), as illustrated in the following reaction scheme:

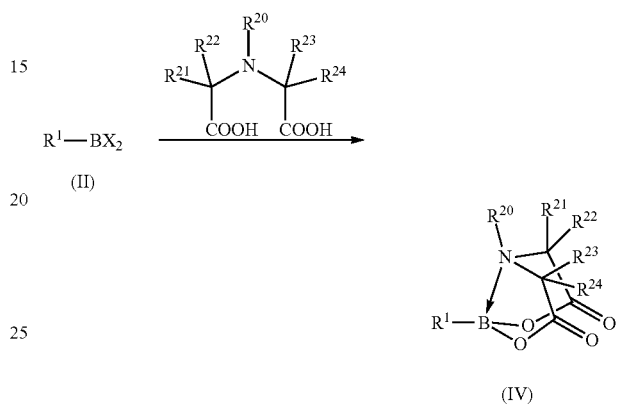

The boronic halide may be formed by hydroborylation of an alkene or an alkyne with HBX$_2$ (Brown, 1984; Brown, 1982) or with BX$_3$ (Soundararajan, 1990). The boronic halide also may be formed by treatment of a silane such as $R^1$—SiR$_3$ with BBr$_3$. (Qin, 2002; Qin, 2004)

Protected organoboronic acids including a MIDA boronate ester protecting group are readily purified by column chromatography. This is unusual for organoboronic acids, which are typically unstable to chromatographic techniques. These protected organoboronic acids also may be crystalline, which can facilitate purification, utilization, and storage. These protected organoboronic acids are stable to long term storage, including storage on the bench top under air. This is also unusual, as many organoboronic acids are unstable to long term storage.

When unprotected, the corresponding organoboronic acid is unstable by the "boronic acid neat stability test". In the "boronic acid neat stability test," an NMR stock solution is prepared by combining bromoacetophenone (0.336 g, 1.69 mmol, internal standard for quantification of the organoboronic acid), tetramethylsilane (TMS, 1 mL, internal standard for the NMR shifts), and DMSO-d$_6$:D$_2$O 95:5 in a 25 mL volumetric flask, to a final solution volume of 25.0 mL. Two 7-mL vials are charged with 10 mg of a freshly prepared unprotected organoboronic acid. These vials are sealed with screwcaps lined with poly(tetafluoroethylene) (PTFE) under ambient atmosphere and are maintained at 23° C. The solid sample present in one of the vials is combined with 1.00 mL of the NMR stock solution, and the resulting solution is analyzed by $^1$H NMR. This first NMR analysis is used to measure the moles of unprotected organoboronic acid present at time zero. The moles of unprotected organoboronic acid present is determined by comparing the ratio of the integrated 4-bromoacetophenone aryl C—H doublets (7.90 ppm relative to TMS) to that of the organoboronic acid C—H signals. After 15 days, the solid sample in the other vial is combined with 1.00 mL of the NMR stock solution, and the resulting solution is analyzed by $^1$H NMR in the same way. This second NMR analysis is used to determine the moles of unprotected organoboronic acid remaining after 15 days of exposure to the ambient atmosphere at 23° C. If the unprotected organoboronic acid is stable by the "boronic acid neat stability test", then the number of moles of the unprotected organoboronic acid measured in the second NMR analysis will be at least 90% of the number of moles of the unprotected organoboronic acid measured in the first NMR analysis.

Preferably, when an unstable unprotected organoboronic acid is subjected to the boronic acid neat stability test, the number of moles of the unprotected organoboronic acid measured in the second NMR analysis sample is at most 90% of the number of moles of the unprotected organoboronic acid measured in the first NMR analysis. More preferably, the number of moles of the unprotected organoboronic acid measured in the second NMR analysis sample is at most 80% of the number of moles of the unprotected organoboronic acid measured in the first NMR analysis. More preferably, the number of moles of the unprotected organoboronic acid measured in the second NMR analysis sample is at most 50% of the number of moles of the unprotected organoboronic acid measured in the first NMR analysis. More preferably, the number of moles of the unprotected organoboronic acid measured in the second NMR analysis sample is at most 20% of the number of moles of the unprotected organoboronic acid measured in the first NMR analysis. More preferably, the number of moles of the unprotected organoboronic acid measured in the second NMR analysis sample is at most 10% of the number of moles of the unprotected organoboronic acid measured in the first NMR analysis. More preferably, the number of moles of the unprotected organoboronic acid measured in the second NMR analysis sample is at most 5% of the number of moles of the unprotected organoboronic acid measured in the first NMR analysis.

FIG. 2 includes chemical structures, reaction schemes and product yields for examples of the above method, as well as for cross-coupling reactions involving unprotected organoboronic acids. Listed in FIG. 2 are examples of unstable unprotected organoboronic acids, including 2-furyl boronic acid, 2-benzofuryl boronic acid, 2-thiophenyl boronic acid, 4-(4'-methylthiophene)-thiophen-2-boronic acid, 2-(N-butoxycarbonyl-pyrollyl) boronic acid, 2-(N-phenylsulfonate-indolyl) boronic acid, vinyl boronic acid and cyclopropyl boronic acid. These structures of these unprotected organoboronic acids are depicted as compounds 1a-1h, respectively. FIG. 2 also lists the moles of each unprotected organoboronic acid as measured in the second NMR analysis of the boronic acid neat stability test, as a percentage of the moles of each unprotected organoboronic acid as measured in the first NMR analysis of the boronic acid neat stability test. Unprotected organoboronic acids 1a-1h all decomposed significantly on the benchtop under air over the course of just 15 days. For unprotected organoboronic acids 1a and 1e-1h, very little of the original material remained after 15 days. Examples of unstable unprotected organoboronic acids not listed in FIG. 2 include 2-pyridyl boronic acid.

In contrast to the unprotected organoboronic acids 1a-1h, the corresponding MIDA boronates 2a-2h were indefinitely stable to air, with no detectable decomposition by $^1$H NMR even after more than 60 days on the benchtop under air. These MIDA boronates were stable to purification by chromatographically, and were purified as free-flowing solids.

The compound with which the protected organoboronic acid is reacted may be an organohalide or an organo-pseudohalide. The compound may be an organohalide, which is an organic compound that includes at least one halogen group. Examples of halogen groups that may be present in an organohalide compound include —F, —Cl, —Br or —I. The compound may be an organo-pseudohalide, which is an organic compound that includes at least one pseudohalogen group. Examples of pseudohalogen groups that may be present in an organo-pseudohalide compound include triflate (—O—S(=O)$_2$—CF$_3$), methanesulfonate (—O—S(=O)$_2$—CH$_3$), cyanate (—C≡N), azide (—N$_3$) thiocyanate (—N=C=S), thioether (—S—R), anhydride (—C(=O)—O—C(=O)—R), and phenyl selenide (—Se—C$_6$H$_5$). The halogen or pseudo-halogen group may be bonded to an alkyl group, a heteroalkyl group, an alkenyl group, a heteroalkenyl group, an alkynyl group, a heteroalkynyl group, an aryl group, a heteroaryl group, or a combination of at least two of these groups.

The compound with which the protected organoboronic acid is reacted may be an organohalide or an organo-pseudohalide in which the halogen or pseudo-halogen group is bonded to an aryl group or a heteroaryl group. In one example, the compound is an unactivated aryl chloride or an unactivated heteroaryl chloride. Unactivated aryl chlorides, which do not contain any electron-withdrawing groups, typically react more slowly than aryl bromides or activated aryl chlorides in cross-coupling reactions.

The reaction mixture includes a base, and preferably the base has a pK$_B$ of at least 1. Preferably the base has a pK$_B$ of at least 1.5, more preferably of at least 2, more preferably of at least 3. Examples of bases having a pK$_B$ of at least 1 include bases that include an anion selected from [PO$_4$]$^{3-}$, [C$_6$H$_5$O]$^-$, [CO$_3$]$^{2-}$ and [HCO$_3$]$^{1-}$, such as alkali and alkaline earth salts of these anions. Specific examples of such bases include Li$_3$PO$_4$, Na$_3$PO$_4$, K$_3$PO$_4$, Li$^+$[C$_6$H$_5$O]$^-$, Na$^+$[C$_6$H$_5$O]$^-$, K$^+$[C$_6$H$_5$O]$^-$, Li$_2$CO$_3$, Na$_2$CO$_3$, K$_2$CO$_3$, MgCO$_3$, CaCO$_3$, LiHCO$_3$, NaHCO$_3$, and KHCO$_3$.

Preferably the reaction mixture includes a solvent. Examples of solvents include protic solvents such as water, methanol, ethanol, isopropyl alcohol (IPA) and butanol. Examples of solvents include aprotic solvents such as tetrahydrofuran (THF), dioxane, dimethyl formamide (DMF), toluene and xylene. The reaction mixture may include a mixture of two or more solvents, which independently may be a protic or aprotic solvent. Preferably the reaction mixture includes a protic solvent. A protic solvent may facilitate dissociation of the base in the reaction mixture. The identity of the protic solvent may affect the chemical structure of the product of the removal of the protecting group from the protected organoboronic acid. For example, if the reaction mixture includes water, this product is believed to have the structure of the corresponding unprotected organoboronic acid, represented by formula (II):

$$R^1\text{—B(OH)}_2 \tag{II}$$

If the reaction mixture instead includes an alcohol having the structure R$^{10}$—OH, where R$^{10}$ is an organic group, this product is believed to have the structure represented by formula (VII):

$$R^1\text{—B(OR}^{10})_2 \tag{VII}$$

The reaction mixture may include other ingredients, such as a copper-containing compound and/or a fluoride anion source. Examples of copper-containing compounds include CuI, CuCl and Cu(OAc)$_2$. Examples of fluoride anion sources include KF, NaF, and CsF.

Forming a cross-coupled product in the reaction mixture may include maintaining the reaction mixture at a temperature and for a time sufficient to form a cross-coupled product. For example, forming a cross-coupled product in the reaction mixture may include maintaining the reaction mixture at a temperature from 0° C. to 200° C. Preferably the forming includes maintaining the reaction mixture at a temperature from 25° C. to 150° C., and more preferably includes maintaining the reaction mixture at a temperature from 50° C. to 120° C. Forming a cross-coupled product in the reaction mixture may include maintaining the reaction mixture for a period of 1 hour to 100 hours. Preferably the forming includes maintaining the reaction mixture for a period of 2 hours to 72 hours, and more preferably includes maintaining the reaction mixture for a period of 4 hours to 48 hours. Preferably the forming a cross-coupled product in the reaction mixture includes maintaining the reaction mixture at a temperature from 25° C. to 150° C. for a period of 2 hours to 72 hours, and more preferably includes maintaining the reaction mixture at a temperature from 50° C. to 120° C. for a period of 4 hours to 48 hours.

The yield of cross-coupled product from this method may be remarkably improved, relative to a similar method in which the base is not a mild base, such as a base having a $pK_B$ less than 1. The yield of cross-coupled product in the reaction mixture from this method may be at least 50%. Preferably the yield of cross-coupled product in the reaction mixture from this method is at least 60%. More preferably the yield of cross-coupled product in the reaction mixture from this method is at least 70%, more preferably is at least 75%, more preferably is at least 80%, more preferably is at least 85%, more preferably is at least 90%, more preferably is at least 95%, and more preferably is at least 99%.

Figure 3:
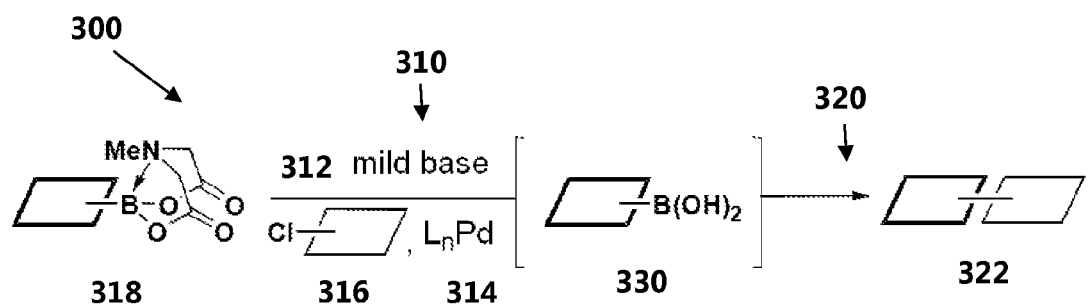
FIG. 3 represents a method of performing a chemical reaction.

FIG. 3 represents a method 300 of performing a chemical reaction, including reacting 310 an organochloride 316 and a protected organoboronic acid 318 in a reaction mixture containing a mild base 312 and a palladium catalyst 314; and forming 320 a cross-coupled product 322 in the reaction mixture. The MIDA protecting group of the protected organoboronic acid 318 may be cleaved in situ, providing the corresponding unprotected organoboronic acid 330, which can then cross-couple with the organochloride 316.

Referring again to FIG. 2, the unprotected organoboronic acids 1a-1h or the corresponding protected organoboronic acids 2a-2h were reacted with an aryl chloride in a reaction mixture, and a cross-coupled product was formed in the reaction mixture. In each set of examples, the reaction mixture included water, $K_3PO_4$ as the base, $Pd(OAc)_2$/SPhos as the catalyst, aryl chloride 1-tert-butoxy-4-chlorobenzene 3a as the organohalide, and one equivalent of either a protected organoboronic acid or a corresponding unprotected organoboronic acid, where the unprotected organoboronic acid was prepared just prior to the reaction. Each of the unprotected organoboronic acids was determined to be unstable by the boronic acid neat stability test.

For the unprotected organoboronic acids according to formula (II), where $R^1$ was a 2-heterocyclic group (1a-1f), the isolated yields of cross-coupled products 4a-4f ranged from 14-68%. In contrast, for the corresponding protected organoboronic acids according to formula (I), where $R^1$ was a 2-heterocyclic group (2a-2f), the isolated yields of cross-coupled products 4a-4f ranged from 90-96%. For compounds 1a-1e and 2a-2e, the isolated yields for the protected organoboronic acids increased by 38% to 148% relative to those of the corresponding unprotected organoboronic acids. For compounds 1f and 2f, the isolated yield for the protected organoboronic acids increased by over 500% relative to that of the corresponding unprotected organoboronic acid.

For the unprotected vinyl boronic acid (1g), the isolated yield of cross-coupled product 4g was 79%. In contrast, the corresponding MIDA vinyl boronate 2g had an isolated yield of 98%, an increase of 24%. For the unprotected cyclopropyl boronic acid (1h), the isolated yield of cross-coupled product 4h was 95%, and the corresponding MIDA cyclopropyl boronate 2h had an isolated yield of 96%.

Figure 4:
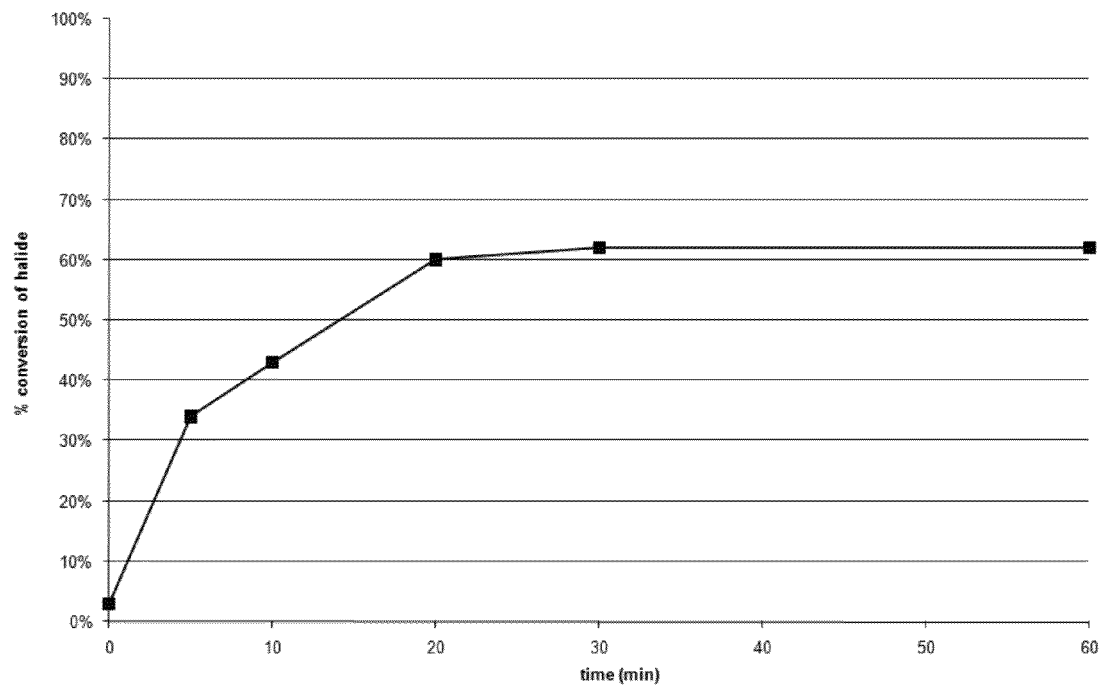
Figure 5:
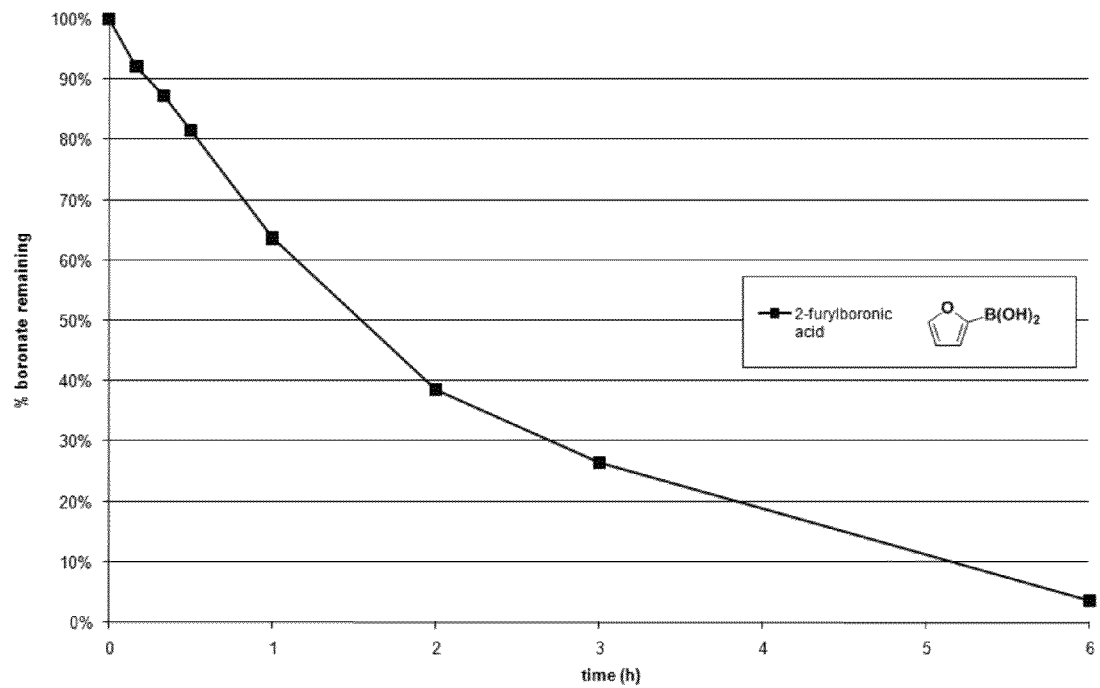
FIG. 5 depicts a graph of the decomposition of 1a over time.

One possible explanation for these results is that there is kinetic competition between the cross-coupling reaction and the decomposition of the unprotected organoboronic acids. Thus, an unstable organoboronic acid may significantly degrade under NaOH-promoted Suzuki-Miyaura coupling conditions, during the finite time between its formation by the deprotection reaction and its consumption in the cross-coupling reaction. FIG. 4 is a graph of the cross-coupling conversion of unprotected 2-furyl boronic acid 1a with 1-tert-butoxy-4-chlorobenzene 3a at 60° C., the results of which are listed in FIG. 2. The conversion of the aryl chloride 3a was slightly over 60% after 30 minutes, and then remained level for the remainder of the first hour of reaction. FIG. 5 is a graph of the decomposition of 1a over time under similar reaction conditions, but without the aryl chloride and catalyst. Within 30 minutes, over 10% of the organoboronic acid had decomposed, and less than 65% of the organoboronic acid remained after 1 hour. Thus, the cross-coupling and decomposition of 1a occurred simultaneously, and the two processes competed for the organoboronic acid in the reaction mixture.

Competition between the cross-coupling reaction and the decomposition of an unprotected organoboronic acid can have negative effects on the yield of cross-coupling reactions performed using protected organoboronic acids. The deprotection in aqueous NaOH of MIDA boronates to their corresponding organoboronic acids typically is complete within 10 min at 23° C. (Gillis, 2007). If the deprotection/cross-coupling reaction of protected organoboronic acid 2a with 3a is performed with NaOH as the base, all of the organoboronic acid would be in the unprotected form 1a within the first 10 minutes of the reaction. Once the organoboronic acid is unprotected, decomposition would begin to decrease the amount of this reactant in the mixture, as illustrated in FIG. 5. Since the organoboronic acid is present in its unprotected form very early in the reaction, the progress of conversion of the cross-coupling reaction with 3a should be similar to that illustrated in FIG. 4.

Consistent with this prediction, the cross-coupling reactions listed in FIG. 2 for 1a and 2a were modified to substitute 3 molar (M) aqueous NaOH as the base instead of the aqueous $K_3PO_4$. The isolated yields of product 4a in these reactions were 64% and 59%, respectively. These isolated yields were similar to each other and to the 68% isolated yield listed in FIG. 2 for the cross-coupling of the corresponding unprotected organoboronic acid 1a using $K_3PO_4$ as the base. The isolated yield of 4a from the cross-coupling reaction starting with protected organoboronic acid 2a thus decreased by 37% when the base in the reaction was changed from $K_3PO_4$ to NaOH.

The negative effects on the yield of cross-coupling reactions performed using protected organoboronic acids due to competition between the cross-coupling reaction and the decomposition of an unprotected organoboronic acid can be minimized or eliminated by providing for a slow release of the unprotected organoboronic acid. In one example, MIDA boronates can be deprotected in a mixture of $K_3PO_4$ in dioxane:$H_2O$ 5:1 at 60° C. over the course of 3 or more hours, gradually providing a supply of the corresponding unprotected organoboronic acid to the reaction mixture. This rate of this gradual deprotection can be modified by changing the temperature of the reaction mixture, with higher temperatures correlating with a faster deprotection rate, as well as a faster rate of the cross-coupling reaction.

Figure 6:
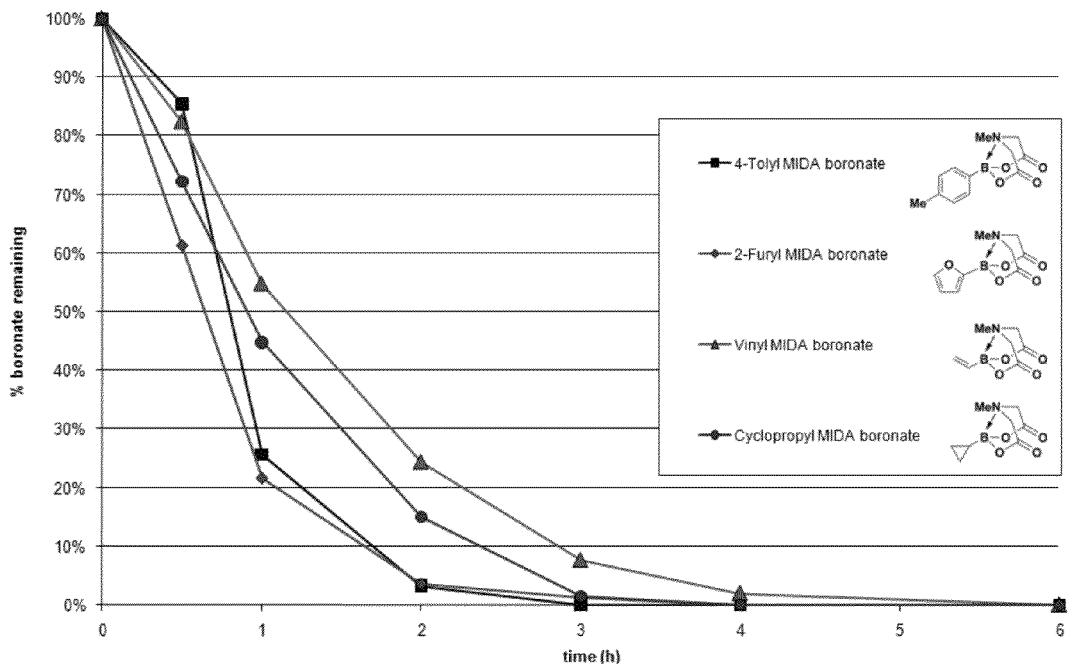
FIG. 6 depicts a graph of the deprotection of a variety of MIDA boronates over time.
Figure 7:
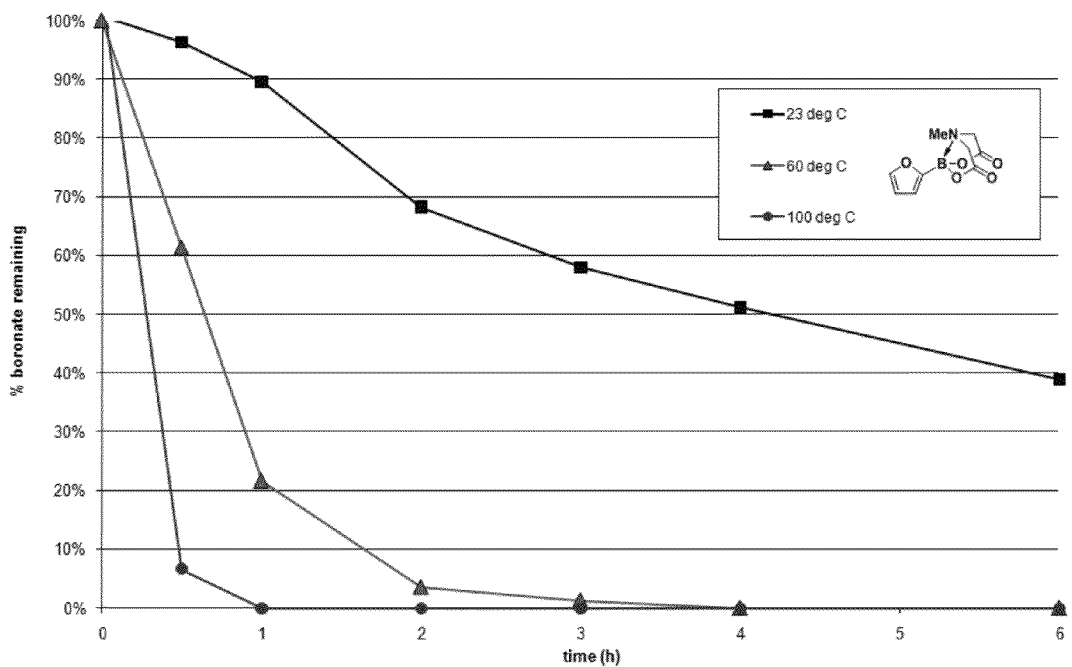
FIG. 7 is a graph of the deprotection of 2a over time at 23° C., 60° C. and 100° C.
Figure 8:
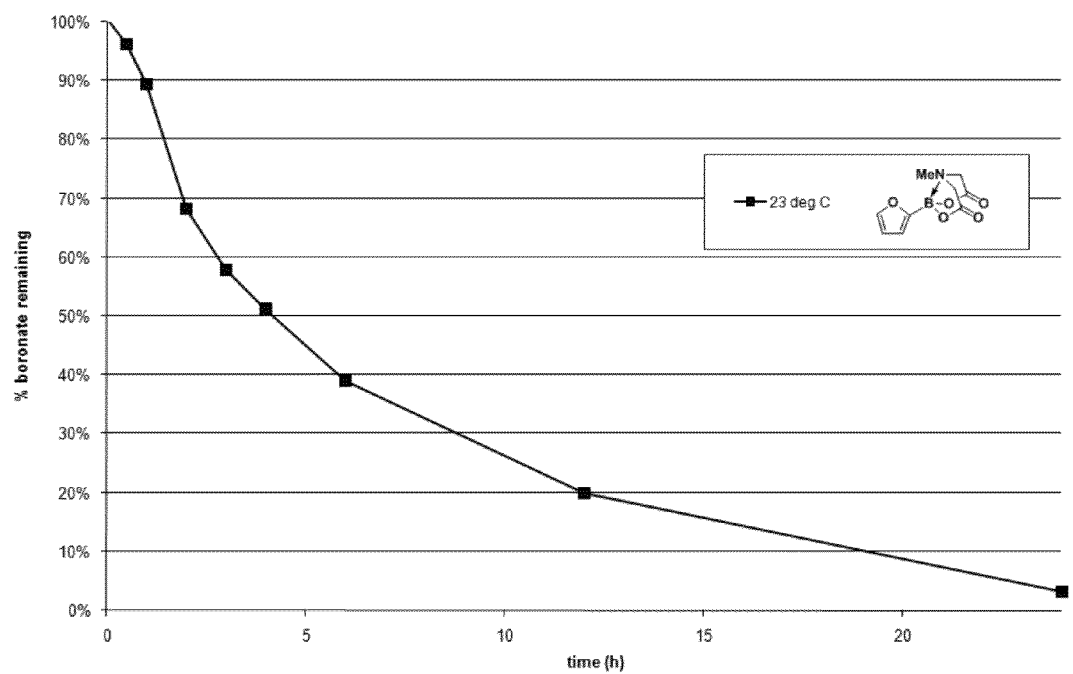
FIG. 8 is a graph of the deprotection of 2a over time at 23° C.

FIG. 6 is a graph of the deprotection of an aryl MIDA boronate (4-tolyl MIDA boronate), a heteroaryl MIDA boronate (2-furyl MIDA boronate, 2a), an alkenyl MIDA boronate (vinyl MIDA boronate, 2g), and an alkyl MIDA boronate (cyclopropyl MIDA boronate, 2g) in the presence of $K_3PO_4$ at 60° C. over time. The deprotection progress was similar for all of these different types of MIDA boronates. FIG. 7 is a graph of the deprotection of 2a at 23° C., 60° C. and 100° C. over time, and FIG. 8 is a graph of the deprotection of 2a at 23° C. over time. The time required for over 90% of the MIDA boronate to be deprotected decreased from approximately 24 hours at 23° C., to 30 minutes at 100° C.

The gradual deprotection of 2-furyl MIDA boronate 2a to 2-furyl boronic acid 1a was simulated by performing the cross-coupling reaction listed in FIG. 2 for 1a, but replacing the unprotected organoboronic acid initially present in the reaction mixture with a dropwise addition of a solution of the unprotected organoboronic acid in dioxane over the course of 3 hours using a syringe pump. The isolated yield of 4a from this reaction was 98%, which was comparable to the isolated yield provided by the reaction of the protected organoboronic acid 2a with $K_3PO_4$ as the base.

Thus, while not wishing to be bound by any theory of operation, it appears that the increased product yields listed in FIG. 2 for cross-coupling of MIDA boronates 2a-2g, relative to the yields for cross-coupling of the corresponding unprotected organoboronic acids 1a-1g, is due to the slow release of the unprotected organoboronic acids from the MIDA boronates, as facilitated by the mild base $K_3PO_4$.

A method of performing a chemical reaction includes deprotecting in a reaction mixture a protected organoboronic acid represented by formula (I):

$$R^1\text{—B-T} \qquad (I),$$

to form a corresponding unprotected organoboronic acid that is unstable by the boronic acid neat stability test, where $R^1$ represents an organic group, B represents boron having $sp^3$ hybridization, and T represents a conformationally rigid protecting group as described above. The reaction mixture also includes a base and a palladium catalyst. The method further includes reacting the unprotected organoboronic acid and a compound selected from the group consisting of an organohalide and an organo-pseudohalide in the reaction mixture, and forming a cross-coupled product in the reaction mixture. The time required for at least 90% of the protected organoboronic acid to be deprotected in the reaction mixture is at least equal to the time required for 90% of the cross-coupled product to be formed in the reaction mixture.

Preferably the time required for at least 90% of the protected organoboronic acid to be deprotected in the reaction mixture is greater than the time required for 90% of the cross-coupled product to be formed in the reaction mixture. More preferably, the time required for at least 90% of the protected organoboronic acid to be deprotected in the reaction mixture is at least twice the time required for 90% of the cross-coupled product to be formed in the reaction mixture, and more preferably is at least three times the time required for 90% of the cross-coupled product to be formed in the reaction mixture.

Referring again to FIGS. 4 and 6, the time required for at least 90% of the protected organoboronic acid 2a to be deprotected in a reaction mixture was at least equal to the time required for 90% of the cross-coupled product 4a to be formed in a comparable reaction mixture. In FIG. 4, the time required for 90% of the cross-coupled product 4a to be formed from the organohalide 3a and the unprotected organoboronic acid 1a was approximately 20 minutes at 60° C. In FIG. 6, the time required for 90% of the corresponding protected organoboronic acid 2a to be deprotected was approximately 1.5 hours at 60° C. Thus, the time required for at least 90% of the protected organoboronic acid 2a to be deprotected in a reaction mixture was at least four times the time required for 90% of the cross-coupled product 4a to be formed in a comparable reaction mixture.

The $R^1$ group may include, for example, a 2-heterocyclic group, a vinyl group or a cyclopropyl group, as described above. The compound with which the unprotected organoboronic acid is reacted may be an organohalide or an organo-pseudohalide, as described above. In one example, the compound may be an unactivated aryl chloride or an unactivated heteroaryl chloride. The reaction mixture may include a mild base, such as a base having a $pK_B$ of at least 1, of at least 1.5, of at least 2, or of at least 3, and may include an anion selected from the group consisting of $[PO_4]^{3-}$, $[C_6H_5O]^-$, $[CO_3]^{2-}$ and $[HCO_3]^{1-}$.

The reaction mixture preferably includes a solvent, which may be a mixture of two or more solvents. Examples of solvents include protic solvents and aprotic solvents, as described above. The reaction mixture may also include other ingredients, such as a copper-containing compound and/or a fluoride anion source, as described above.

Forming a cross-coupled product in the reaction mixture may include maintaining the reaction mixture at a temperature and for a time sufficient to form a cross-coupled product. The reaction temperature may be, for example, from 0° C. to 200° C., from 25° C. to 150° C., or from 50° C. to 120° C. The reaction time may be, for example, from 1 hour to 100 hours, from 2 hours to 72 hours, or from 4 hours to 48 hours. Preferably the reaction is maintained at a temperature from 25° C. to 150° C. for a period of 2 hours to 72 hours, and more preferably at a temperature from 50° C. to 120° C. for a period of 4 hours to 48 hours.

The yield of cross-coupled product from this method may be remarkably improved, relative to a similar method in which the time required for at least 90% of the protected organoboronic acid to be deprotected in the reaction mixture is less than the time required for 90% of the cross-coupled product to be formed in the reaction mixture. The yield of cross-coupled product in the reaction mixture from this method may be at least 50%, and preferably is at least 60%, at least 70%, at least 75%, at least 80%, at least 85%, at least 90%, at least 95%, or at least 99%.

Figure 9A:
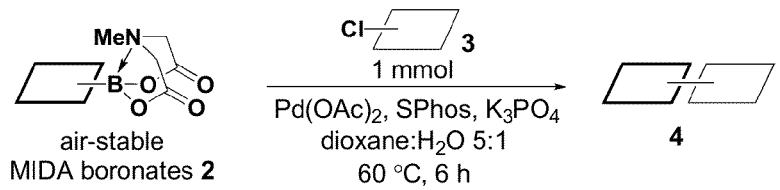

FIGS. 9A and 9B include chemical structures, reaction schemes and product yields for cross-coupling reactions of a variety of MIDA boronates with a variety of aryl chlorides. In each example, the reaction mixture included water, $K_3PO_4$ as the base, $Pd(OAc)_2/SPhos$ as the catalyst, an aryl chloride as the organohalide, and 1.2-1.5 equivalents of the protected organoboronic acid. Each of the unprotected organoboronic acids corresponding to the MIDA boronates was unstable by the boronic acid neat stability test.

In these reactions, even some of the most challenging aryl and heteroaryl chlorides were efficiently coupled with MIDA boronates 2a-h. For example, 2,4-dimethoxychlorobenzene 3b is highly deactivated, due to being electron rich and sterically hindered. This aryl chloride thus represented an exceptionally difficult cross-coupling partner for unstable 2-heterocyclic boronic acids. However, this aryl chloride was converted to a cross-coupled product with isolated yields of 81-99% when reacted with only 1.2 equivalents of one of MIDA boronates 2a-2f (FIGS. 9A-9B; entries 1, 5, 9, 12, and 14). Similarly, 3c is highly deactivated due to sterically hindrance, yet was converted to the cross-coupled product with an isolated yield of 97% when reacted with 1.2 equivalents of MIDA boronate 2a (FIG. 9A; entry 2).

Cross-couplings of 2-heterocyclic boronic acids with inexpensive and readily available heteroaryl chlorides would be highly valuable, due to the importance of polyheterocyclic scaffolds in pharmaceuticals. Heteroaryl chlorides 3d-i were converted to cross-coupled products with isolated yields of 85-99% when reacted with only 1.2 equivalents of one of MIDA boronates 2a-2f (FIGS. 9A-9B; entries 3-4, 6-8, 10-11, 13, and 15). Even the electronically deactivated heteroaryl chlorides 3f-h were coupled to 2b with isolated yields of 85-94% (FIG. 9A; entries 6-8).

Vinylation of aryl and heteroaryl halides can provide styrene-like building blocks for a wide range of small molecules and materials. Thus, the development of a highly effective, non-toxic, environmentally friendly, and air-stable vinyl metal species has long been an important goal. Vinyl MIDA boronate 2g embodies all of these favorable properties and efficiently coupled even with the highly deactivated aryl chloride 3c (FIG. 9B; entry 16), as well as with a variety of heteroaryl chlorides 3i, 3g and 3d (FIG. 9B; entries 17-19).

Cyclopropyl MIDA boronate 2h coupled with highly deactivated aryl chlorides 3c and 3b (FIG. 9B; entries 20-21). Referring again to FIG. 2, cyclopropyl boronic acid 1h was as effective as the corresponding MIDA boronate 2h in cross-coupling with aryl chloride 3a, if the cyclopropyl boronic acid was prepared immediately prior to the reaction. Thus, the decomposition of 1h in air may be the main reason this organoboronic acid has been challenging to use in cross-coupling reactions previously.

Figure 10:
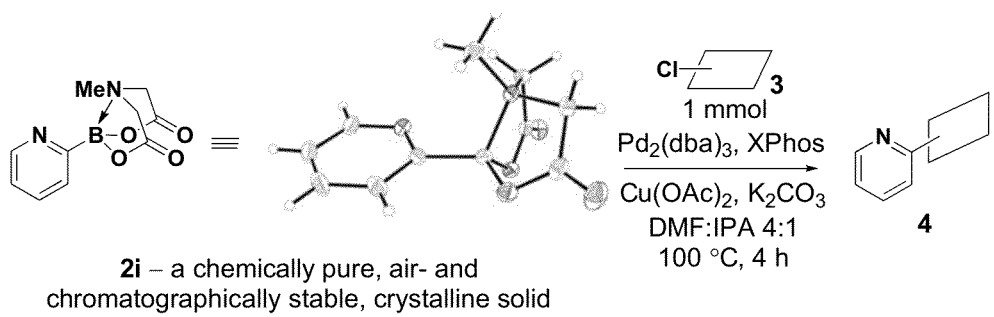
FIG. 10 includes chemical structures, reaction schemes and product yields for cross-coupling reactions of 2-pyridyl MIDA boronate with a variety of aryl chlorides.

FIG. 10 includes chemical structures, reaction schemes and product yields for cross-coupling reactions of 2-pyridyl MIDA boronate with a variety of aryl chlorides. In each example, the reaction mixture included a protic solvent, $K_3PO_4$ as the base, $Pd(OAc)_2$/SPhos as the catalyst, an aryl chloride as the organohalide, and 1.5 equivalents of the protected organoboronic acid. The unprotected organoboronic acid, 2-pyridyl boronic acid, is notoriously unstable and difficult to cross-couple, particularly with aryl chlorides. Currently-available surrogates are either not air-stable or cannot be isolated in chemically pure form. However, since the 2-pyridyl subunit appears frequently in biologically active small molecules, synthetic strategies involving the 2-pyridyl group could be valuable.

The 2-pyridyl MIDA boronate 2i was isolable as a chemically pure and air-stable solid. The X-ray structure is depicted in FIG. 10. Studies with $^1$H NMR of the material showed no decomposition after 60 days on the benchtop under air. The rate of transmetalation for 2-pyridylboranes is slower relative to other boron compounds. Reaction conditions similar to those listed in FIGS. 2, 9A and 9B typically were not effective for couplings with 2i; however, use of an alcohol-containing solvent mixture and a copper-containing compound improved the cross-coupling yields. In the reactions listed in FIG. 10, the solvent used was a 4:1 mixture of DMF:IPA, and the inexpensive and non-toxic $Cu(OAc)_2$ salt was also present. As shown in FIG. 10, under these modified slow-release conditions, 2-pyridyl MIDA boronate 2i was cross-coupled with a variety of aryl and heteroaryl chlorides 3e, 3i, 3j, 3k and 3l.

FIG. 11 includes chemical structures, reaction schemes and product yields for cross-coupling reactions of a variety of MIDA boronates with a variety of aryl bromides and aryl chlorides. In each example, the reaction mixture included water, $K_3PO_4$ as the base, $Pd(OAc)_2$/SPhos as the catalyst, an aryl bromide or aryl chloride as the organohalide, and 1.5 equivalents of the protected organoboronic acid.

The 2-furan MIDA boronate 2a cross-coupled with outstanding yields to electron-poor and electron-rich aryl bromides 5a and 5b (FIG. 11; entries 1 and 2), as well as to the unactivated aryl chloride 5c (FIG. 11; entry 3). 2-Benzofuran MIDA boronate 2b was also highly effective with all three coupling partners (FIG. 11; entries 4-6). 2-Thiophene boronic acids are important building blocks for many natural products, materials, and pharmaceuticals, but can be unstable to storage and cross-coupling conditions. (Billingsley, 2007; Tyrrell, 2003; Gronowitz, 1990) The 2-thiophene MIDA boronates 2c and 2d, however, were air-stable and were excellent coupling partners (FIG. 11; entries 7-10), and the cross-coupling of 2c and 5a was achieved simply using $Pd(PPh_3)_4$ (FIG. 11; entry 7).

Similarly, 2-substituted nitrogen heterocycles represent some of the most important building blocks for the synthesis of many pharmaceuticals and natural products, yet they have been especially poor substrates for Suzuki-Miyaura coupling. (Billingsley, 2007; Tyrrell, 2003; Billingsley, 2008; Yamamoto, 2008; Johnson, 1998) Remarkably, air-stable 2-indole MIDA boronate 2j delivered excellent cross-coupling yields using this method (FIG. 11; entries 11-13), even with an unactivated aryl chloride coupling partner (FIG. 11; entry 13).

Vinyl boronic acid is known to undergo rapid polymerization and usually cannot even be isolated. (Matteson, 1960; Lightfoot, 2005; Kerins, 2002; Molander, 2006; Matteson, 1980) In stark contrast, the corresponding MIDA boronate 2g was an air-stable, crystalline solid that could be conveniently prepared on the multigram scale. Using this method, this reagent was highly effective for the vinylation of aryl bromides using Pd/SPhos (FIG. 11; entries 14 and 16) or $Pd(PPh_3)_4$ (FIG. 11; entry 15). There are no prior reports of vinylation of an unactivated aryl chloride with an organoborane, and only a single example of cross-coupling of vinyl trifluoroborate with the electronically activated p-chloroacetophenone 3j, albeit in low yield. (Molander, 2006) Strikingly, cross-coupling with 2g using this method proved to be highly effective, not only for this activated substrate (FIG. 11; entry 17), but also for the unactivated aryl chloride 5m (FIG. 11; entry 18). Finally, cyclopropyl MIDA boronate 2h was a highly effective cross-coupling partner when using $PdCl_2dppf$ as catalyst (FIG. 11; entry 19).

The following examples are provided to illustrate one or more preferred embodiments of the invention. Numerous variations can be made to the following examples that lie within the scope of the invention.

EXAMPLES

General Methods

Commercial reagents were purchased from Sigma-Aldrich (St. Louis, Mo.), Fisher Scientific (Waltham, Mass.), Alfa Aesar/Lancaster Synthesis (Ward Hill, Mass.), TCI America (Portland, Oreg.), Frontier Scientific (Logan, Utah), Oakwood Products (West Columbia, S.C.) or Combi-Blocks (San Diego, Calif.) and were used without further purification unless otherwise noted. Solvents were purified via passage through packed columns as described by Pangborn and coworkers (Pangborn, 1996) (THF, $Et_2P$, $CH_3CN$, $CH_2Cl_2$: dry neutral alumina; hexane, benzene, and toluene, dry neutral alumina and Q5 reactant (copper(II) oxide on alumina); DMSO, DMF: activated molecular sieves). All water was deionized prior to use. Triethylamine, diisopropylamine, diethylamine, pyridine, and 2,6-lutidine were freshly distilled under an atmosphere of nitrogen from $CaH_2$. The following compounds were prepared according to procedures reported in the literature: N-methyliminodiacetic acid (Ballmer), vinyl MIDA boronate 2g (Uno, 2009), 5-bromo-2-thiopheneboronic acid MIDA ester (Gillis, 2007).

Unless otherwise noted, all reactions were performed in flame-dried glassware under argon. Organic solutions were concentrated via rotary evaporation under reduced pressure with a bath temperature of 35-40° C. Reactions were monitored by analytical thin layer chromatography (TLC) performed using the indicated solvent on E. Merck silica gel 60 F254 plates (0.25 mm). Compounds were visualized by: exposure to a UV lamp (λ=254 or 366 nm), incubation in a glass chamber containing iodine, and/or treatment with a solution of $KMnO_4$, an acidic solution of p-anisaldehyde or a solution of ceric ammonium molybdate (CAM) followed by brief heating with a Varitemp® heat gun (Master Appliance; Racine, Wis.).

Column chromatography was performed using standard methods (Still, 1978) or with a CombiFlash $R_f$ (Teledyne-Isco; Lincoln, Nebr.) purification system. Both methods were performed using Merck silica gel grade 9385 60 A (230-400 mesh). For loading, compounds were adsorbed onto non acid-washed Celite 545 (approximately 10 g/mmol crude product) in vacuo from an acetone solution. Specifically, in each case the crude residue was dissolved/suspended in acetone and to the mixture was added Celite. The mixture was concentrated in vacuo to afford a free flowing powder which was then loaded on top of a silica gel column. To ensure quantitative transfer, this procedure was repeated with a small amount of acetone and Celite to transfer any remaining residue. MIDA boronates were compatible with standard silica gel chromatography, including standard loading techniques.

$^1$H-NMR spectra were recorded at 23° C. on a Varian Unity or a Varian Unity Inova 500 MHz spectrometer (Varian; Palo Alto, Calif.). Chemical shifts (δ) were reported in parts per million (ppm) downfield from tetramethylsilane and referenced to residual protium in the NMR solvent ($CHCl_3$, δ=7.26; $CD_2HCN$, δ=1.93, center line; acetone-$d_6$ δ=2.04, center line). Alternatively, NMR-solvents designated as "w/TMS" were referenced to tetramethylsilane (δ=0.00 ppm) added as an internal standard. Data were reported as follows: chemical shift, multiplicity (s=singlet, d=doublet, t=triplet, q=quartet, quint=quintet, sept=septet, m=multiplet, br=broad, app=apparent), coupling constant (J) in Hertz (Hz), and integration.

$^{13}$C NMR spectra were recorded at 23° C. on a Varian Unity 500 MHz spectrometer. Chemical shifts (δ) were reported in ppm downfield from tetramethylsilane and referenced to carbon resonances in the NMR solvent ($CDCl_3$, δ=77.0, center line; $CD_3CN$, δ=1.30, center line, acetone-$d_6$ δ=29.80, center line) or to added tetramethylsilane (δ=0.00). Carbons bearing boron substituents were not observed (quadrupolar relaxation).

$^{11}$B NMR spectra were recorded using a General Electric GN300WB instrument and referenced to an external standard of ($BF_3.Et_2O$). High resolution mass spectra (HRMS) were performed by Furong Sun and Dr. Steve Mullen at the University of Illinois School of Chemical Sciences Mass Spectrometry Laboratory. Infrared spectra were collected from a thin film on NaCl plates or as KBr pellets on a Spectrum BX FT-IR spectrometer (Perkin-Elmer; Waltham, Mass.), a Mattson Galaxy Series FT-IR 5000 spectrometer or a Mattson Infinity Gold FT-IR spectrometer. Absorption maxima ($v_{max}$) were reported in wavenumbers ($cm^{-1}$). X-ray crystallographic analysis of 2i was carried out by Dr. Scott Wilson and Dr. Danielle Gray at the University of Illinois George L. Clark X-Ray facility.

Example 1

Preparation of Protected Organoboronic Acids From Corresponding Unprotected Boronic Acids The general method for synthesizing protected organoboronic acids was as follows. To a roundbottom flask equipped with a stir bar was added the boronic acid (1 equiv), N-methyliminodiacetic acid (1-1.5 equiv), DMSO and either toluene or benzene. The flask was fitted with a Dean-Stark trap, and the Dean-Stark trap was fitted with a reflux condenser vented to ambient atmosphere. The stirred mixture was heated to reflux with azeotropic removal of water for 2-18 hours. The solution was concentrated in vacuo (1 Torr, 100° C.). Unless otherwise noted, the resulting residue was adsorbed onto Celite in vacuo from an acetone suspension and the resulting powder was subjected to flash chromatography ($Et_2O \to Et_2O$:MeCN). An example of this method is depicted in the scheme below.

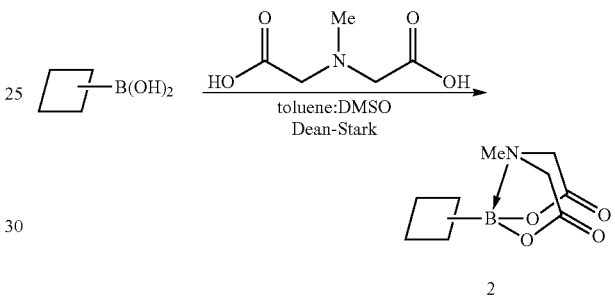

To form protected organoboronic acid 2a, the general procedure was followed using furan-2-boronic acid (5.029 g, 44.95 mmol, Sigma-Aldrich), N-methyliminodiacetic acid (7.275 g, 49.44 mmol), toluene (210 mL) and DMSO (40 mL). The mixture was refluxed for 8 h. The product was eluted with $Et_2O \to Et_2O$:acetone 1:1. The solid thus obtained was dissolved in a minimum of acetone, to which $Et_2O$ was slowly added to promote crystallization. Filtration of the mixture afforded 2a as an off-white crystalline solid (8.98 g, 90%). TLC (EtOAc) $R_f$=0.33, stained with $KMnO_4$. $^1$H-NMR (500 MHz, $CD_3CN$) δ 7.66 (dd, J=2.0, 1.0 Hz, 1H), 6.71 (dd, J=3.0, 1.0 Hz, 1H), 6.43 (dd, J=3.0, 2.0 Hz, 1H), 4.06 (d, J=17 Hz, 2H), 3.89 (d, J=17 Hz, 2H), 2.60 (s, 3H). $^{13}$C-NMR (125 MHz, $CD_3CN$) δ 169.2, 147.0, 119.1, 110.8, 62.4, 47.9. $^{11}$B-NMR (96 MHz, $CD_3CN$) δ 9.5. HRMS (EI+) Calculated for $C_9H_{10}BNO_5$ (M)$^+$: 223.0652, Found: 223.0651. IR (thin film, $cm^{-1}$) 3136, 3109, 3002, 2990, 2962, 1751, 1570, 1481, 1457, 1419, 1346, 1336, 1302, 1245, 1227, 1197, 1153, 1085, 1057, 1004, 965, 932, 873, 839, 828, 823.

To form protected organoboronic acid 2b, the general procedure was followed using benzofuran-2-boronic acid (5.247 g, 32.39 mmol, Sigma-Aldrich), N-methyliminodiacetic acid (5.005 g, 34.02 mmol), toluene (135 mL) and DMSO (15 mL). The mixture was refluxed for 8 h. The product was eluted with $Et_2O \to Et_2O$:MeCN 2:1. The solid thus obtained was dissolved in a minimum of acetone, to which $Et_2O$ was slowly added to promote crystallization. Filtration of the mixture afforded 2b as a colorless crystalline solid (7.61 g, 86%). TLC (EtOAc) $R_f$=0.45, visualized by UV (254 nm) and $KMnO_4$ stain. $^1$H-NMR (500 MHz, $CD_3CN$) δ 7.63 (app dq, J=7.5, 1.0 Hz, 1H), 7.51 (app. dt, J=8.5, 1.0 Hz, 1H), 7.30 (m, 1H), 7.22 (app tt, J=7.5, 0.5 Hz, 1H), 7.11 (s, 1H), 4.14 (d, J=17 Hz, 2H), 3.97 (d, J=17 Hz, 2H), 2.69 (s, 3H). $^{13}$C-NMR (125 MHz, CD$_3$CN) δ 169.2, 158.2, 129.1, 125.7, 123.6, 122.4, 115.8, 112.2, 62.6, 48.1. $^{11}$B-NMR (96 MHz, CD$_3$CN) δ 9.5. HRMS (EI+) Calculated for C$_{13}$H$_{12}$BNO$_5$ (M)$^+$: 273.0809, Found: 273.0810. IR (thin film, cm$^{-1}$) 3008, 2956, 1765, 1560, 1448, 1335, 1282, 1249, 1191, 1157, 1138, 1052, 1005, 942, 853.

To form protected organoboronic acid 2c, the general procedure was followed using thiophene-2-boronic acid (4.871 g, 38.06 mmol, Sigma-Aldrich), N-methyliminodiacetic acid (5.884 g, 39.99 mmol), benzene (180 mL) and DMSO (20 mL). The mixture was refluxed for 8 h. The product was eluted with Et$_2$O→Et$_2$O:MeCN 2:1. The solid thus obtained was dissolved in a minimum of acetone, to which Et$_2$O was slowly added to promote crystallization. Filtration of the mixture afforded 2c as a colorless crystalline solid (7.13 g, 78%). TLC (EtOAc) R$_f$=0.34, visualized by UV (254 and 366 nm) and KMnO$_4$ stain. $^1$H-NMR (500 MHz, CD$_3$CN) δ 7.62 (dd, J=5.0, 1.0 Hz, 1H), 7.28 (dd, J=3.5, 1.0 Hz, 1H), 7.19 (dd, J=5.0, 3.5 Hz, 1H), 4.07 (d, J=17 Hz, 2H), 3.90 (d, J=18 Hz, 2H), 2.58 (s, 3H). $^{13}$C-NMR (125 MHz, CD$_3$CN) δ 169.1, 134.2, 130.7, 129.5, 62.4, 48.3. $^{11}$B-NMR (96 MHz, CD$_3$CN) δ 11.2. HRMS (EI+) Calculated for C$_9$H$_{10}$BNO$_4$S (M)$^+$: 239.0424, Found: 239.0432. IR (thin film, cm$^{-1}$) 3007, 2954, 1773, 1704, 1514, 1457, 1421, 1337, 1285, 1226, 1172, 1029, 979, 894, 860, 814, 713.

To form protected organoboronic acid 2f, the general procedure was followed using 1-(phenylsulfonyl)-2-indoleboronic acid (1.396 g, 4.64 mmol, Sigma-Aldrich), N-methyliminodiacetic acid (0.717 g, 4.88 mmol), toluene (30 mL) and DMSO (15 mL). The mixture was refluxed for 3 h. The mixture was cooled to room temperature and the toluene was removed in vacuo. The resulting DMSO solution was transferred to a separatory funnel and was diluted with H$_2$O (50 mL). The aqueous phase was extracted with THF:Et$_2$O (1:1, 3×25 mL). The combined organics were washed with brine (2×25 mL), dried over MgSO$_4$, filtered and concentrated in vacuo. The residue was adsorbed onto Celite from an acetone solution and the resulting powder was subjected to flash chromatography on silica gel (Et$_2$O:MeCN 100:0→2:1) to afford 2f as a colorless crystalline solid (1.326 g, 69%). TLC (EtOAc) R$_f$=0.42, visualized by UV (254 nm). $^1$H-NMR (500 MHz, CD$_3$CN) δ 8.18 (d, J=8.5 Hz, 1H), 7.99 (d, J=7.0, 2H), 7.59 (m, 2H), 7.49 (t, J=8.5 Hz, 2H), 7.36 (ddd, J=8.5, 7.5, 1.5 Hz, 1H), 7.26 (app. td, J=7.0, 1.0 Hz, 1H), 7.16 (d, J=0.5 Hz, 1H), 4.16 (d, J=18 Hz, 2H), 4.11 (d, J=18 Hz, 2H), 3.00 (s, 3H). $^{13}$C-NMR (125 MHz, CD$_3$CN) δ 140.4, 139.7, 135.3, 131.3, 130.4, 127.8, 126.6, 124.8, 123.8, 122.6, 115.7, 65.9, 50.7. $^{11}$B-NMR (96 MHz, CD$_3$CN) δ 10.9. HRMS (EI+) Calculated for C$_{19}$H$_{17}$O$_6$N$_2$SB (M)$^+$: 412.0900, Found: 412.0897. IR (KBr, cm$^{-1}$) 3068, 3014, 1769, 1528, 1469, 1448, 1363, 1340, 1299, 1228, 1176, 1124, 1091, 1042, 1010, 966, 865, 750, 727, 686, 656, 589, 573, 561.

To form protected organoboronic acid 2h (Uno, 2009), the general procedure was followed using cyclopropyl boronic acid (5.139 g, 59.82 mmol, purchased from Oakwood Products), N-methyliminodiacetic acid (10.56 g, 71.79 mmol), DMSO (20 mL) and toluene (20 mL). The mixture was refluxed for 2 h. The mixture was cooled to room temperature and then was concentrated in vacuo (1 Torr, 100° C.). Although the product is stable to chromatography, for convenience the purification step was modified to employ crystallization. The residue oil was suspended in EtOAc (500 mL) and was transferred to a 2 L separatory funnel. The mixture was washed with water (250 mL). The aqueous phase was extracted with EtOAc (3×250 mL). The combined organics were washed with brine (50 mL) and then were dried over MgSO$_4$, filtered, and concentrated in vacuo. The resulting crude product was dissolved in acetone (approximately 100 mL), and then was diluted slowly over 1 h with Et$_2$O (1.5 L) to promote crystallization of the product. The mixture was filtered to isolate 2h as a colorless, crystalline solid (8.775 g, 74%). TLC (EtOAc) R$_f$=0.21, stained with KMnO$_4$. $^1$H-NMR (500 MHz, CD$_3$CN) δ 3.92 (d, J=17 Hz, 2H), 3.80 (d, J=17 Hz, 2H), 2.98 (s, 3H), 0.46 (dq, J=9.5, 3.0 Hz, 2H), 0.12 (m, 2H), −0.33 (m, 1H). $^{13}$C-NMR (125 MHz, acetone-d6) δ 169.0, 62.7, 46.8, 1.2. $^{11}$B-NMR (96 MHz, CD$_3$CN) δ 13.2. HRMS (FAB+) Calculated for C$_8$H$_{13}$BNO$_4$ (M+H)$^+$: 198.0938, Found: 198.0937. IR (thin film, cm$^{-1}$) 2998, 1744, 1457, 1358, 1337, 2197, 1246, 1129, 1048, 985, 956, 892, 880, 845, 704.

To form protected organoboronic acid 2j, the general procedure was followed using N-methylindole-2-boronic acid (3.00 g, 17.1 mmol), N-methyliminodiacetic acid (2.77 g, 18.9 mmol), benzene (60 mL) and DMSO (30 mL). The mixture was refluxed for 3 h. The product was eluted with Et$_2$O:MeCN 2:1 to afford the boronate ester 2j as a colorless crystalline solid (4.55 g, 93%). TLC (EtOAc) R$_f$=0.39, visualized by UV (254 nm) and KMnO$_4$. $^1$H-NMR (500 MHz, CD$_3$CN) δ 7.57 (app dt, J=8.0, 1.0 Hz, 1H), 7.39 (dd, J=8.0, 1.0 Hz, 1H), 7.20 (ddd, J=8.0, 7.0, 1.0 Hz, 1 H), 7.04 (ddd, J=8.0, 7.0, 1.0 Hz, 1H), 6.66 (d, J=1.0 Hz, 1H), 4.07 (d, J=17 Hz, 2H), 3.92 (d, J=17 Hz, 2H), 3.82 (s, 3H), 2.56 (s, 3H). $^{13}$C-NMR (125 MHz, CD$_3$CN) δ 169.4, 141.3, 129.0, 122.9, 121.5, 120.0, 111.4, 110.6, 62.3, 47.8, 32.8. $^{11}$B-NMR (96 MHz, CD$_3$CN) δ 10.8. HRMS (EI+) Calculated for C$_{14}$H$_{15}$BN$_2$O$_4$ (M)$^+$: 286.1125, Found: 286.1127. IR (thin film, cm$^-$) 3000, 2948, 1765, 1653, 1617, 1508, 1456, 1509, 1456, 1360, 1332, 1276, 1236, 1161, 1037, 998, 962, 897, 859.

Example 2

Preparation of Protected Organoboronic Acid 2d

A catalyst solution was prepared. In a glove box, to a 40 mL vial equipped with a stir bar was added Pd(OAc)$_2$ (0.137 g, 0.610 mmol), dicyclohexylphosphino-2',6'-dimethoxy-1,1'-biphenyl (SPhos) (0.502 g, 1.22 mmol) and THF (25 mL). The solution was stirred for 30 minutes upon which the color of the solution changed from orange to yellow.

The catalyst solution was then utilized in a reaction to form boronate ester 2d. To a 500 mL two-neck flask equipped with a stir bar was added 2-bromothiophene-5-MIDA boronate ester (Gillis, 2007) (4.862 g, 15.29 mmol), 4-methylthiophene-2-boronic acid (4.808 g, 30.58 mmol) and K$_3$PO$_4$ (anhydrous, finely ground, 9.739 g, 45.89 mmol). The flask was fitted with a reflux condenser and the second arm was fitted with a rubber septum. The flask was placed under Ar atm. and to the flask was added THF (150 mL). To the flask was added via cannula the catalyst stock solution (25 mL). The mixture was heated to 45° C. with stirring for 12 h. The mixture was cooled to room temperature and then was filtered through a thin pad of silica gel eluting with a copious volume of MeCN. The filtrate was concentrated in vacuo and the crude residue was adsorbed onto Celite from an acetone solution. The resulting powder was subjected to flash chromatography on silica gel (Et$_2$O, then Et$_2$O:MeCN 2:1) to afford a green foam, which was further purified by dissolving the product in a minimum of acetone followed by slow addition of Et$_2$O to promote crystallization. Filtration of the resulting mixture afforded 2d as a pale green solid (3.744 g, 73%). This method is depicted in the scheme below.

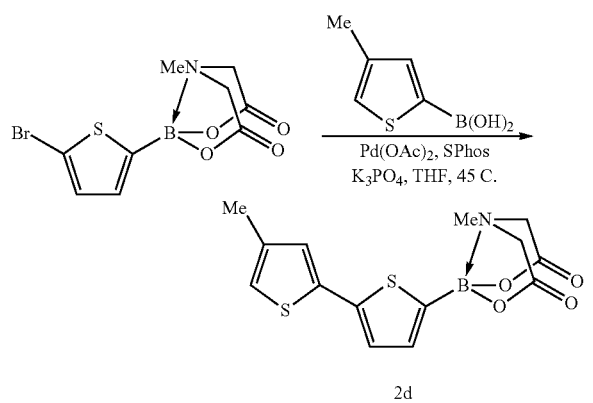

2d

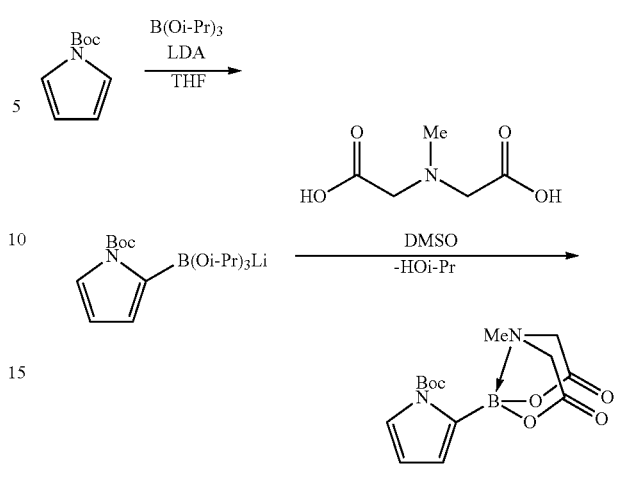

2e

TLC (EtOAc) $R_f$=0.38, visualized by UV (254 and 366 nm) and KMnO$_4$ stain. $^1$H-NMR (500 MHz, CD$_3$CN) δ 7.24 (d, J=3.5 Hz, 1H), 7.17 (d, J=3.5 Hz, 1H), 7.09 (d, J=1.5 Hz, 1H), 6.91 (app quint, J=1.0 Hz, 1H), 4.07 (d, J=17 Hz, 2H), 3.91 (d, J=17 Hz, 2H), 2.66 (s, 3H), 2.22 (d, J=1.0 Hz, 3H). $^{13}$C-NMR (125 MHz, CD$_3$CN) δ 169.1, 142.5, 139.8, 137.6, 135.3, 127.3, 125.9, 121.2, 62.4, 48.4, 15.7. $^{11}$B-NMR (96 MHz, CD$_3$CN) δ 10.9. HRMS (EI+) Calculated for C$_{14}$H$_{14}$BNO$_4$S$_2$ (M)$^+$: 335.0457, Found: 335.0457. IR (thin film, cm$^{-1}$) 3004, 2953, 1773, 1453, 1419, 1336, 1285, 1231, 1193, 1169, 1037, 980, 858, 806.

Example 3

Preparation of Protected Organoboronic Acid 2e

To a 50 mL Schlenk flask equipped with a stir bar was added THF (15 mL) and diisopropylamine (920 microliters). The solution was cooled to −78° C. and then to the stirred solution was added dropwise n-BuLi (2.5 M in hexanes, 2.75 mL). The solution was maintained at −78° C. for 10 min, and then was allowed to warm to room temperature with stirring for 3 h. The solution was cooled to −78° C., and to the stirred solution was added dropwise via cannula N-tert-butoxycarbonylpyrrole (1.016 g, 6.074 mmol) as a solution in THF (15 mL+10 mL washing). The solution was stirred for 30 min. To the yellow solution was added dropwise triisopropylborate (1.40 mL, 6.07 mmol). The solution was stirred for 10 min at −78° C. and then was allow to warm to room temperature with stirring overnight (11 h). To the near-black solution was added DMSO (15 mL). The THF was then removed in vacuo and the resulting DMSO solution was transferred to a 50 mL pressure-equalizing addition funnel. The funnel was fitted onto a 100 mL 3-neck round-bottom flask charged with N-methyliminodiacetic acid (1.407 g, 9.563 mmol) and DMSO (20 mL). To a second neck was fitted a short-path distillation apparatus connected to vacuum. The third neck of the flask was sealed with a septum. The system was placed under vacuum (1 Torr) and the mixture was heated to 75° C. upon which the DMSO began to distill. The DMSO solution of lithium triisopropyl 2-(N-tert-butoxycarbonyl)pyrrole borate was added to the distilling mixture dropwise over 1 h. The mixture was further distilled to near dryness (1 h). The resulting residue was suspended in acetone and concentrated in vacuo onto Celite (10 g). The resulting powder was lyophilized for one day to remove additional DMSO and then was subjected to flash chromatography on silica gel (Et$_2$O: MeCN, 100:0→80:20) to afford 2e as an off-white crystalline solid (565 mg, 29%). This method is depicted in the scheme below.

TLC (EtOAc) $R_f$=0.35, stained with KMnO$_4$. $^1$H-NMR (500 MHz, CD$_3$CN) δ 7.38 (dd, J=3.0, 1.5 Hz, 1H), 6.61 (dd, J=3.0, 1.5 Hz, 1H), 6.20 (t, J=3.0 Hz, 1H), 4.09 (d, J=17 Hz, 2H), 4.05 (d, 17 Hz, 2H), 2.79 (s, 3H), 1.54 (s, 9H). $^{13}$C-NMR (125 MHz, CD$_3$CN) δ 169.9, 151.2, 126.2, 124.9, 112.1, 84.9, 65.9, 49.9, 28.0. $^{11}$B-NMR (96 MHz, CD$_3$CN) δ 11.1. HRMS (EI+) Calculated for C$_{14}$H$_{20}$BN$_2$O$_6$ (M+H)$^+$: 323.1414, Found: 323.1414. IR (KBr, cm$^{-1}$) 3174, 3118, 3012, 2982, 2941, 1743, 1457, 1337, 1304, 1296, 1253, 1235, 1146, 1027, 1008, 815, 747.

Example 4

Preparation of Protected Organoboronic Acid 2i

To a 250 mL Schlenk flask equipped with a stir bar was added 2-bromopyridine (6.00 mL, 62.9 mmol), triisopropylborate (15.0 mL, 65.2 mmol) and THF (100 mL). The solution was cooled to −78° C. To the stirred solution was added dropwise n-BuLi (25.0 mL, 2.5 M in hexanes) at a rate sufficiently slow as to avoid the accumulation of a red color in the mixture (approximately 20 minutes). The resulting beige mixture was stirred for 30 min and then was allowed to warm to room temperature with stirring overnight (12 h). The mixture was concentrated in vacuo onto Celite (10 g) to afford a free-flowing powder. Separately, a 500 mL 3-neck round-bottom flask equipped with a stir bar was charged with N-methyliminodiacetic acid (15.77 g, 107.2 mmol) and DMSO (100 mL). To one neck of the flask was fitted a solid addition funnel charged with the Celite-adsorbed lithium triisopropyl 2-pyridylborate. To a second neck was fitted a short-path distillation apparatus connected to vacuum. The third neck of the flask was sealed with a septum. The system was placed under vacuum (1 Torr) and the mixture was heated to 75° C. upon which the DMSO began to distill. The lithium triisopropyl 2-pyridylborate was added to the distilling mixture portion-wise over 1 h. The mixture was further distilled to near dryness (1 h). The resulting residue was suspended in acetone, and then concentrated in vacuo onto additional Celite (10 g). The resulting powder was lyophilized for 3 days to remove additional DMSO, and then was subjected to flash chromatography on silica gel (40 g silica gel, Et$_2$O:MeCN, 100:0→0:100). The product thus obtained was suspended in acetone (5 mL) and then diluted with Et$_2$O (100 mL) to promote crystallization. The mixture was filtered to isolate 2i as an off-white crystalline solid (4.024 g, 27%). This method is depicted in the scheme below.

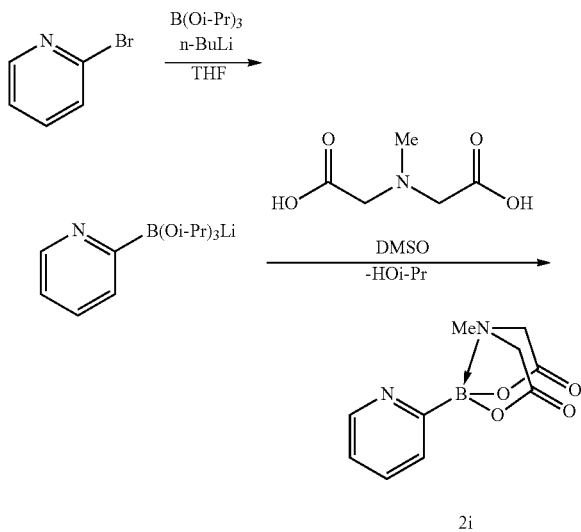

TLC (MeCN) $R_f$=0.26, visualized by UV (254 nm) and $KMnO_4$ stain. $^1$H-NMR (500 MHz, $CD_3CN$) δ 8.67 (ddd, J=2.5, 1.5, 1.0 Hz, 1H), 7.70 (td, J=7.5, 1.5 Hz, 1H), 7.62 (dt, J=7.5, 1.0 Hz, 1H), 7.28 (ddd, J=8.5, 1.5 Hz, 1H), 8.67 (ddd, J=4.5, 1.5, 1.0 Hz, 1H), 4.09 (d, J=17 Hz, 2H), 3.98 (d, J=17 Hz, 2H), 2.55 (s, 3H). $^{13}$C-NMR (125 MHz, $CD_3CN$) δ 169.6, 150.8, 135.8, 128.1, 124.3, 62.9, 47.6. $^{11}$B-NMR (96 MHz, $CD_3CN$) δ 10.3. HRMS (EI+) Calculated for $C_{10}H_{12}O_4N_2B$ $(M+H)^+$: 235.0890, Found: 235.0895. IR (KBr, $cm^{-1}$) 3174, 3118, 3012, 2982, 2941, 1743, 1457, 1337, 1304, 1296, 1253, 1235, 1146, 1027, 1008, 815, 747.

Example 5

Preparation of Unprotected Organoboronic Acids

The general method for synthesizing unprotected organoboronic acids was as follows. Under ambient atmosphere, to a 100 mL flask equipped with a stir bar and charged with MIDA boronate (2) (5 mmol) as a solution in THF (50 mL) was added aqueous NaOH (1.0 M, 15 mL). The mixture was vigorously stirred for 20 min. The mixture was then transferred to a separatory funnel and was diluted with $Et_2O$ (50 mL) and 0.5 M pH 7 sodium phosphate buffer (50 mL). The mixture was shaken, and the phases were separated. The aqueous phase was extracted with THF:$Et_2O$ (1:1, 2×25 mL). The combined organics were dried over $MgSO_4$, filtered and concentrated in vacuo. Residual solvent was co-evaporated with MeCN, and the resulting solid was placed under vacuum (~1 Torr) for 30 min. All boronic acids thus obtained were judged to be >95% pure by $^1$H-NMR and were utilized in cross-coupling reactions immediately after preparation. An example of this method is depicted in the scheme below.

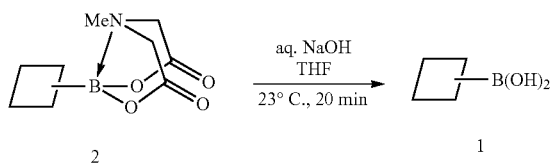

To form unprotected organoboronic acid 1a, the general procedure was followed using MIDA boronate 2a (1.127 g, 5.002 mmol) to yield the 1a as an off white solid (0.531 g, 95%). TLC (EtOAc) $R_f$=0.46, stained with $KMnO_4$. $^1$H-NMR (500 MHz, DMSO-$d_6$:$D_2O$ 95:5 w/ TMS) δ 7.81 (dd, J=1.5, 0.5 Hz, 1H), 7.07 (dd, J=3.0, 0.5 Hz, 1H), 6.48 (dd, J=3.5, 2.0 Hz, 1H). $^{13}$C-NMR (125 MHz, DMSO-$d_6$:$D_2O$ 95:5 w/ TMS) δ 146.4, 121.5, 110.3. HRMS (EI+) Calculated for $C_4H_5O_3B$ $(M)^+$: 112.0332, Found: 112.0332.

To form unprotected organoboronic acid 1b, the general procedure was followed using MIDA boronate 2b (1.374 g, 5.033 mmol) to yield 1b as an off white solid (0.728 g, 89%). TLC (EtOAc) $R_f$=0.14, visualized by UV (254 and 366 nm) and $KMnO_4$ stain. $^1$H-NMR (500 MHz, DMSO-$d_6$:$D_2O$ 95:5 w/ TMS) δ 7.71 (d, J=8.0 Hz, 1H), 7.60 (d, J=8.5 Hz, 1H), 7.50 (s, 1H), 7.37 (t, J=8.0 Hz, 1H), 7.26 (t, J=7.5 Hz, 1H). $^{13}$C-NMR (125 MHz, DMSO-$d_6$:$D_2O$ 95:5 w/ TMS) δ 156.4, 127.6, 125.3, 122.5, 121.8, 117.5, 111.4.

To form unprotected organoboronic acid 1c, the general procedure was followed using MIDA boronate 2c (1.207 g, 5.048 mmol) to yield 1c as a white solid (0.641 g, 99%). TLC (EtOAc) $R_f$=0.23, visualized by UV (254 nm) and $KMnO_4$ stain. $^1$H-NMR (500 MHz, DMSO-$d_6$:$D_2O$ 95:5 w/ TMS) δ 7.75 (d, J=5.0 Hz, 1H), 7.69 (d, J=3.5 Hz, 1H), 7.18 Hz (app t, J=4.0 Hz, 1H). $^{13}$C-NMR (125 MHz, DMSO-$d_6$:$D_2O$ 95:5 w/ TMS) δ 135.9, 131.5, 128.1.

To form unprotected organoboronic acid 1d, the general procedure was followed using MIDA boronate 2d (1.099 g, 3.277 mmol) and aqueous NaOH (1.0 M, 10 mL). Reaction and workup volumes were scaled accordingly. Boronic acid 1d was isolated as a green solid (0.667 g, 91%). TLC (EtOAc) $R_f$=0.34, visualized by UV (254 and 366 nm) and $KMnO_4$ stain. $^1$H-NMR (500 MHz, DMSO-$d_6$:$D_2O$ 95:5 w/ TMS) δ 7.59 (d, J=3.5 Hz, 1H), 7.29 (d, J=3.5 Hz, 1H), 7.17 (d, J=1.0 Hz, 1H), 7.08 (s, 1H), 2.22 (s, 3H). $^{13}$C-NMR (125 MHz, DMSO-$d_6$:$D_2O$ 95:5 w/ TMS) δ 142.0, 138.3, 137.0, 136.3, 126.3, 124.6, 120.6, 15.3. HRMS (ESI+) Calculated for $C_9H_{10}O_2S_2B$ $(M+H)^+$: 225.0215, Found: 225.0204.

To form unprotected organoboronic acid 1e, the general procedure was followed using MIDA boronate 2e (0.691 g, 2.144 mmol) and aqueous NaOH (1.0 M, 6.5 mL). Reaction volumes were scaled accordingly. After addition of NaOH, the reaction was stirred at 23° C. for 10 min. The reaction mixture was transferred to a separatory funnel and was diluted with $Et_2O$ (20 mL) and 1M aqueous NaOH (20 mL). The mixture was shaken and the organic phase was separated and discarded. The aqueous phase was diluted with THF:$Et_2O$ (1:1, 20 mL) and saturated aqueous $NH_4Cl$ (20 mL). The mixture was shaken and the phases were separated. The aqueous phase was extracted with THF:$Et_2O$ (1:1, 2×10 mL). The combined organics were dried over $MgSO_4$, filtered and concentrated in vacuo to afford 1e as a colorless solid (0.403 g, 89%). TLC (EtOAc) $R_f$=0.50, visualized by UV (254 nm) and $KMnO_4$ stain. $^1$H-NMR (500 MHz, DMSO-$d_6$: $D_2O$ 95:5 w/ TMS) δ 7.34 (dd, J=1.5 Hz, 1H), 6.46 (dd, J=3.5, 2.0 Hz, 1H), 6.23 (t, J=3.0 Hz, 1H), 1.54 (s, 9H). $^{13}$C-NMR (125 MHz, DMSO-$d_6$:$D_2O$ 95:5 w/ TMS) δ 149.8, 123.0, 120.6, 111.7, 84.1, 27.3.

To form unprotected organoboronic acid 1f, the general procedure was followed using MIDA boronate 2f (1.236 g, 2.999 mmol) THF (30 mL), and aqueous NaOH (1.0 M, 9 mL). The mixture was stirred 5 min. The mixture was transferred to a separatory funnel and was diluted with $Et_2O$ (30 mL) and aqueous NaOH (1.0 M, 30 mL). The mixture was shaken and the organic phase was separated and discarded. The aqueous phase was diluted with THF:$Et_2O$ (1:1, 30 mL) and saturated aqueous $NH_4Cl$ (30 mL). The mixture was shaken and the phases were separated. The aqueous phase was extracted with THF:$Et_2O$ (1:1, 2×15 mL). The combined organics were dried over MgSO$_4$, filtered and concentrated in vacuo to afford 2f as a pale yellow solid (584 mg, 65%). TLC (EtOAc) R$_f$=0.53, visualized by UV (254 and 366 nm). $^1$H-NMR (500 MHz, DMSO-d$_6$:D$_2$O 95:5 w/ TMS) δ 8.02 (d, J=7.5 Hz, 2H), 7.84 (d, J=8.0 Hz, 1H), 7.65 (t, J=7.5 Hz, 1H), 7.56 (t, J=7.5 Hz, 3H), 7.28 (t, J=7.5 Hz, 1H), 7.20 (t, J=8.0 Hz, 1H), 6.81 (s, 1H). $^{13}$C-NMR (125 MHz, DMSO-d$_6$:D$_2$O 95:5 w/ TMS) δ 137.1, 135.4, 134.2, 131.1, 129.4, 126.9, 124.3, 123.3, 121.1, 114.4, 113.3.

To form unprotected organoboronic acid 1g, the general procedure was followed using MIDA boronate 2g (0.915 g, 5.00 mmol) and aqueous NaOH (1.0 mL, 15 mL). Due to the volatility of the product, solvent removal was performed at 23° C. Residual solvent was co-evaporated with CH$_2$Cl$_2$. To further remove solvent, the product was briefly (<1 minute) placed under vacuum (~1 Torr). Boronic acid 1g was isolated as a white solid (0.161 g, 45%). TLC (EtOAc) R$_f$=0.31, stained with KMnO$_4$. $^1$H-NMR (500 MHz, DMSO-d$_6$:D$_2$O 95:5 w/ TMS) δ 6.01 (dd, J=19, 5.5 Hz, 1H), 5.80 (m, 2H). $^{13}$C-NMR (125 MHz, DMSO-d$_6$:D$_2$O 95:5 w/ TMS) δ 133.7. HRMS (CI+) Calculated for C$_2$H$_6$O$_2$B (M+H)$^+$: 73.04609, Found: 73.04602.

To form unprotected organoboronic acid 1h, the general procedure was followed using MIDA boronate 2h (0.789 g, 4.00 mmol) and aqueous NaOH (1.0 M, 12 mL). Reaction and workup volumes were scaled accordingly. Boronic acid 1h was isolated as an off-white solid (0.183 g, 53%). TLC (EtOAc) R$_f$=0.22, stained with KMnO$_4$. $^1$H-NMR (500 MHz, DMSO-d$_6$:D$_2$O 95:5 w/ TMS) δ 0.43 (m, 2H), 0.33 (m, 2H), −0.39 (m, 1H). $^{13}$C-NMR (125 MHz, DMSO-d$_6$:D$_2$O 95:5 w/ TMS) δ 3.29.

Example 6

Determination of Benchtop Stability of Boronic Acids and MIDA boronates

The stability of boronic acids or MIDA boronates to storage as solids under air at 23° C. was quantified using the following general procedure. Two 7-mL vials were charged with 10 mg of freshly prepared boronic acid or MIDA boronate at 23° C. under ambient atmosphere. The vials containing these solid samples were then sealed with PTFE-lined screwcaps under ambient atmosphere and placed on the benchtop at 23° C. The solid sample present in one of the vials was then immediately analyzed by $^1$H-NMR to verify the purity and quantity of boronic acid present at time zero (the NMR assay is described below). After 15 days (boronic acids) or 60 days (MIDA boronates), the solid sample in the second vial was analyzed by $^1$H NMR, again by the method described below, to determine the quantity of boronic acid remaining at the indicated time. The results of the analysis for unprotected organoboronic acids 1a-1h and for protected organoboronic acids 2a-2h are listed in FIG. 2.

In the NMR assay, an NMR stock solution was prepared. To a 25 mL volumetric flask was added bromoacetophenone (0.336 g, 1.69 mmol, internal standard for quantification of the boronic acid), tetramethylsilane (1 mL, internal standard for the NMR shifts), and DMSO-d$_6$:D$_2$O 95:5 to a final solution volume of 25.0 mL. To a vial containing solid boronic acid or solid MIDA boronate (see above) was added 1.00 mL of this NMR stock solution, and the resulting solution was analyzed by 1H NMR. The mmol of boronic acid or MIDA boronate present in the sample was determined by comparing the ratio of the integrated 4-bromoacetophenone aryl C—H doublets (7.90 ppm relative to TMS) to that of the boronic acid or MIDA boronate C—H signals.

Example 7

Comparison of Slow-Release Cross-Coupling Yields of Boronic Acids Vs. MIDA Boronates Under ambient atmosphere, to a 40 mL I-Chem vial equipped with a stir bar was added 1-tert-butoxy-4-chlorobenzene (3a) (185 mg, 1.00 mmol), the MIDA boronate or freshly-prepared boronic acid (1.00 mmol), 2-dicyclohexylphosphino-2',6'-dimethoxybiphenyl (SPhos) (41 mg, 0.10 mmol) and Pd(OAc)$_2$ (11 mg, 0.050 mmol). The vial was sealed with a PTFE-lined septum screw-cap and was placed under Ar atmosphere. To the vial was added dioxane (12.5 mL) and the resulting mixture was stirred at 23° C. for 10 min. To the vial was then added aqueous K$_3$PO$_4$ (3.0 M, 2.5 mL, degassed by sparging with Ar for 30 min). The vial was placed in a 60° C. oil bath with stirring for 6 h. After cooling to room temperature the mixture was transferred to a 60 mL separatory funnel and was diluted with aqueous NaOH (1.0 M, 10 mL) and Et$_2$O (10 mL). The mixture was shaken and the phases were separated. The aqueous phase was extracted with Et$_2$O (3×10 mL). The combined organic fractions were dried over MgSO$_4$, filtered and concentrated in vacuo. The crude residue was subjected to flash-chromatography on silica gel (hexanes:EtOAc). This method is depicted in the scheme below, and the yields of cross-coupling are listed in FIG. 2.

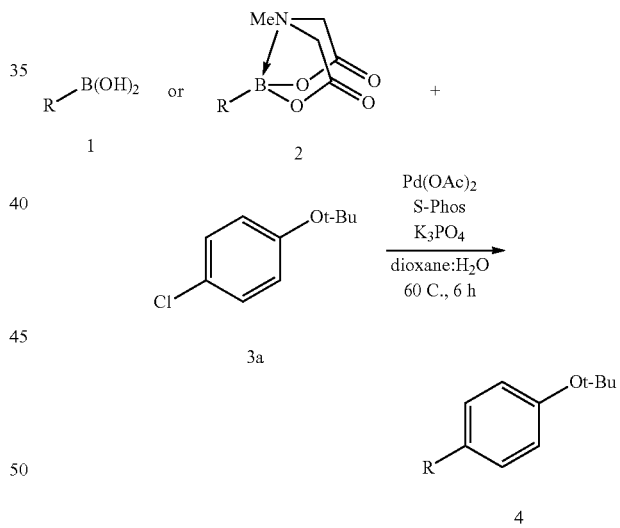

To form 2-(4-tert-butoxyphenyl)furan (4a), the general procedure was followed using MIDA boronate 2a (223 mg, 1.00 mmol) to afford 4a as a colorless oil (203 mg, 94%). A parallel reaction using freshly-prepared boronic acid 1a (112 mg, 1.00 mmol) under otherwise identical conditions afforded 4a as a colorless oil (147 mg, 68%). TLC (hexanes: EtOAc 20:1) R$_f$=0.33, visualized by UV (254 nm). $^1$H-NMR (500 MHz, CDCl$_3$) δ 7.60 (d, J=8.5 Hz, 2H), 7.45 (dd, J=1.5, 0.5 Hz, 1H), 7.04 (d, J=8.5 Hz, 2H), 6.58 (d, J=3.0 Hz, 1H), 6.46 (dd, J=3.0, 1.5 Hz, 1H), 1.38 (s, 9H). $^{13}$C-NMR (125 MHz, CDCl$_3$) δ 154.8, 153.9, 141.6, 126.3, 124.4, 124.3, 111.5, 104.0, 78.7, 28.8. HRMS (CI+) Calculated for C$_{14}$H$_{16}$O$_2$ (M)$^+$: 216.1150, Found: 216.1151. IR (thin film, cm$^{-1}$) 2977, 1612, 1587, 1566, 1512, 1481, 1414, 1390, 1366, 1245, 1162, 1106, 1078, 1007, 904, 895, 854, 798, 730, 667, 594.

To form 2-(4-tert-butoxyphenyl)benzofuran (4b), the general procedure was followed using MIDA boronate 2b (273 mg, 1.00 mmol) to afford 4b as a colorless solid (246 mg, 92%). A parallel reaction using freshly-prepared boronic acid 1b (162 mg, 1.00 mmol) under otherwise identical conditions afforded 4b as a pale yellow solid (134 mg, 50%). TLC (hexanes:EtOAc 20:1) $R_f$=0.28, visualized by UV (254 nm).
$^1$H-NMR (500 MHz, CDCl$_3$) δ 7.83 (d, J=8.5 Hz, 2H), 7.62 (d, J=8.0 Hz, 1H), 7.58 (d, J=8.0 Hz, 1H), 7.33 (t, J=7.0 Hz, 1H), 7.29 (t, J=7.0 Hz, 1H), 7.14 (d, J=8.5 Hz, 2H), 6.96 (s, 1H), 1.46 (s, 9H). $^{13}$C-NMR (125 MHz, CDCl$_3$) δ 156.0, 156.9, 154.7, 129.3, 125.6, 125.5, 124.1, 123.8, 122.8, 120.6, 111.0, 110.3, 78.9, 28.8. HRMS (EI+) Calculated for C$_{18}$H$_{18}$O$_2$ (M)$^+$: 266.1307, Found: 266.1303. IR (thin film, cm$^{-1}$) 2978, 1609, 1499, 1451, 1364, 1298, 1239, 1209, 1157, 1099, 1029, 1007, 918, 893, 853, 806, 750, 713.

To form 2-(4-tert-butoxyphenyl)thiophene (4c) (Messmore, 2004), the general procedure was followed using MIDA boronate 2c (239 mg, 1.00 mmol) to afford 4c as a pale yellow solid (217 mg, 94%). A parallel reaction using freshly-prepared boronic acid 1c (128 mg, 1.00 mmol) under otherwise identical conditions afforded 4c as a pale yellow oil (87 mg, 37%). TLC (hexanes:EtOAc 10:1) $R_f$=0.50, visualized by UV (254 nm). $^1$H-NMR (500 MHz, CDCl$_3$) δ 7.52 (d, J=7.0 Hz, 2H), 7.24 (s, 1H), 7.23 (d, J=1.0 Hz, 1H), 7.06 (dd, J=5.0, 4.0 Hz, 1H), 7.00 (d, J=8.5 Hz, 2H), 1.37 (s, 9H). $^{13}$C-NMR (125 MHz, CDCl$_3$) δ 154.9, 144.1, 129.6, 127.9, 126.4, 124.4, 124.2, 122.4, 78.7, 28.8. HRMS (EI+) Calculated for C$_{14}$H$_{16}$OS (M)$^+$: 232.0922, Found: 232.0921. IR (thin film, cm$^{-1}$) 2978, 1604, 1534, 1498, 1432, 1366, 1243, 1164, 1102, 922, 895, 850, 819, 694, 606, 540.

To form 5'-(4-tert-butoxyphenyl)-4-methyl-2,2'-bithiophene (4d), the general procedure was followed using MIDA boronate 2d (335 mg, 1.00 mmol) to afford 4d as a yellow solid (317 mg, 96%). A parallel reaction using freshly-prepared boronic acid 1d (224 mg, 1.00 mmol) under otherwise identical conditions afforded 4d as a yellow solid (158 mg, 45%; yield corrected for residual 3a). TLC (hexanes: EtOAc 10:1) $R_f$=0.41, visualized by UV (254 and 366 nm).
$^1$H-NMR (500 MHz, CDCl$_3$)
δ 7.50 (d, J=8.5 Hz, 2H), 7.14 (d, J=4.0 Hz, 1H), 7.10 (d, J=4.0 Hz, 1H), 7.01 (m, 3H), 6.79 (s, 1H), 2.27 (s, 3H), 1.39 (s, 9H). $^{13}$C-NMR (125 MHz, CDCl$_3$) δ 155.0, 142.6, 138.3, 137.1, 136.3, 129.2, 126.0, 125.6, 124.3, 124.2, 123.0, 119.4, 78.7, 28.7, 15.6. HRMS (EI+) Calculated for C$_{19}$H$_{20}$OS$_2$ (M)$^+$: 328.0956, Found: 328.0958. IR (thin film, cm$^{-1}$) 2973, 1502, 1466, 1365, 1246, 1160, 1106, 897, 850, 836, 804, 733, 717, 589, 528.

To form N-(tert-butoxycarbonyl)-2-(4-tert-butoxyphenyl) pyrrole (4e), the general procedure was followed using MIDA boronate 2e (322 mg, 1.00 mmol) to afford 4e as a pale yellow solid (284 mg, 90%). A parallel reaction using freshly-prepared boronic acid 1e (211 mg, 1.00 mmol) under otherwise identical conditions afforded 4e as a pale yellow oil (192 mg, 61%). TLC (hexanes:EtOAc 10:1) $R_f$=0.37, visualized by UV (254 nm). $^1$H-NMR (500 MHz, CDCl$_3$) δ 7.36 (dd, J=3.0, 1.5 Hz, 1H), 7.23 (d, J=8.5 Hz, 2H), 6.97 (d, J=8.5 Hz, 2H), 6.22 (t, J=1.5 Hz, 1H), 6.15 (dd, J=3.5, 2.0 Hz, 1H), 1.38 (s, 9H), 1.34 (s, 9H). $^{13}$C-NMR (125 MHz, CDCl$_3$) δ 154.5, 149.5, 134.6, 129.7, 129.6, 123.1, 122.3, 114.2, 110.4, 83.5, 78.4, 28.8, 27.6. HRMS (CI+) Calculated for C$_{19}$H$_{25}$O$_3$N (M)$^+$: 315.1834, Found: 315.1834.

IR (thin film, cm$^{-1}$) 2978, 2934, 1739, 1511, 1474, 1392, 1369, 1337, 1314, 1238, 1162, 1074, 1040, 975, 897, 855, 814, 773, 729.

To form N-phenylsulfonyl-2-(4-tert-butoxyphenyl)indole (4f), the general procedure was followed using MIDA boronate 2f (412 mg, 1.00 mmol). Purification by flash chromatography (SiO$_2$ hexanes:EtOAc 100:0→80:20 followed by C$_{18}$ silica gel (H$_2$O:MeCN 1:1→1:9) afforded 4f as a colorless solid (376 mg, 93%). A parallel reaction using freshly-prepared boronic acid 1f (301 mg, 1.00 mmol) under otherwise identical reaction and purification conditions afforded 4f as a colorless solid (59 mg, 14%). TLC (hexanes:EtOAc 10:1) $R_f$=0.20, visualized by UV (254 and 366 nm).
$^1$H-NMR (500 MHz, CDCl$_3$ w/ TMS) δ 8.32 (d, J=8.5 Hz, 1H), 7.43 (m, 2H), 7.34 (m, 5H), 7.25 (m, 3H), 7.01 (d, J=9.0 Hz, 2H), 6.50 (s, 1H), 1.43 (s, 9H). $^{13}$C-NMR (125 MHz, CDCl$_3$) δ 156.1, 141.8, 138.2, 137.7, 133.4, 131.1, 130.4, 128.5, 126.7, 126.6, 124.6, 124.2, 122.6, 120.5, 116.5, 112.9, 78.8, 28.9. HRMS (EI+) Calculated for C$_{24}$H$_{23}$O$_3$NS (M)$^+$: 405.13987, Found: 405.13919. IR (thin film, cm$^{-1}$) 2979, 2971, 1496, 1446, 1367, 1256, 1238, 1217, 1182, 1171, 1163, 1152, 1120, 1087, 1055, 992, 899, 858, 822, 756, 729, 682, 593, 568, 547.

To form 1-tert-butoxy-4-vinylbenzene (4g) (Conlon, 1989), the general procedure was followed using MIDA boronate 2g (183 mg, 1.00 mmol) with the modification that the reaction was run at 100° C. to afford 4g as a pale yellow liquid (172 mg, 98%). A parallel reaction using freshly-prepared boronic acid 1g (72 mg, 1.0 mmol) under otherwise identical conditions afforded 4g as pale yellow liquid (0.17 g, 79%; yield corrected for residual 3a). TLC (hexanes:EtOAc 10:1) $R_f$=0.54, visualized by UV (254 nm). $^1$H-NMR (500 MHz, CDCl$_3$) δ 7.34 (d, J=8.5 Hz, 2H), 6.97 (d, J=8.5 Hz, 2H), 6.70 (dd, J=18, 11 Hz, 1H), 5.67 (d, J=18 Hz, 1H), 5.19 (d, J=11 Hz, 1H), 1.37 (s, 9H). $^{13}$C-NMR (125 MHz, CDCl$_3$) δ 155.2, 136.3, 132.7, 126.7, 124.1, 112.4, 78.5, 28.8. HRMS (CI+) Calculated for C$_{12}$H$_{16}$O (M)$^+$: 176.1201, Found: 176.1198. IR (thin film, cm$^{-1}$) 2978, 2931, 1630, 1603, 1505, 1473, 1390, 1366, 1243, 1161, 1107, 989, 923, 898, 858, 840.

To form 1-tert-butoxy-4-cyclopropylbenzene (4h), the general procedure was followed using MIDA boronate 2h (183 mg, 1.00 mmol) with the modification that the reaction was run at 100° C. to afford 4h as a pale yellow liquid (183 mg, 96%). A parallel reaction using freshly-prepared boronic acid 1h (86 mg, 1.0 mmol) under otherwise identical conditions afforded 4h as pale yellow liquid (0.18 g, 95%).

TLC (hexanes:EtOAc 10:1) $R_f$=0.51, visualized by UV (254 nm). $^1$H-NMR (500 MHz, CDCl$_3$) δ 6.98 (d, J=8.5 Hz, 2H), 6.90 (d, J=8.5 Hz, 2H), 1.87 (m, 1H), 1.34 (s, 9H), 0.94 (m, 2H), 0.67 (m, 2H). $^{13}$C-NMR (125 MHz, CDCl$_3$) δ 152.9, 138.6, 125.9, 124.1, 78.0, 28.7, 14.8, 8.9. HRMS (CI+) Calculated for C$_{13}$H$_{18}$O (M)$^+$: 190.1358, Found: 190.1357.

IR (thin film, cm$^{-1}$) 3082, 2977, 2932, 1609, 1510, 1474, 1460, 1389, 1365, 1239, 1164, 1105, 1046, 1015, 923, 900, 845, 813.

Example 8

Kinetics of Boronic Acid Cross-Coupling

Under ambient atmosphere, to a 25 mL Schlenk flask equipped with a stir bar was added 2-dicyclohexylphosphino-2',6'-dimethoxybiphenyl (SPhos) (41 mg, 0.10 mmol), Pd(OAc)$_2$ (11 mg, 0.050 mmol) and freshly-prepared 2-furylboronic acid (1a) (106 mg, 0.949 mmol). The flask was placed under Ar atmosphere and to the flask was added dioxane (12.5 mL). To the solution was added dodecane (100 microliters, internal standard) and 1-tert-butoxy-4-chlorobenzene (3a) (175 microliters, 0.980 mmol), and the solution was stirred at 23° C. for 10 minutes. The solution was sampled and analyzed by GC to determine the ratio of halide:dodecane. To the dark amber solution was added aqueous K$_3$PO$_4$ (3.0 M, 2.5 mL, degassed by sparging with Ar for 30 min) and the dark mixture was stirred for 5 minutes. The organic phase was sampled as the initial time-point (t=0), and the mixture was then immediately placed in a 60° C. oil bath with stirring. The organic phase was sampled periodically and the consumption of the halide was determined by GC analysis versus the internal standard. FIG. 4 depicts a graph of the data for cross-coupling conversion of 2-furyl boronic acid 1a with 1-tert-butoxy-4-chlorobenzene 3a.

Example 9

Kinetics of In Situ Boronic Acid Decomposition

A stock solution of 2-furylboronic acid (1a) and 4-bromoanisole (internal standard) in dioxane-d$_8$ was prepared as follows: 2-furylboronic acid (9 mg, 0.08 mmol) and 4-bromoanisole (15 mg, 0.080 mmol) were dissolved in dioxane-d$_8$ (1.0 mL). To each of eight argon-filled 1.5 mL vials equipped with stir bars and sealed with PTFE-lined septum-screwcaps was added the boronic acid stock solution (100 microliters), followed by a solution of K$_3$PO$_4$ in D$_2$O (3.0 M, 20 microliters) by syringe. The mixtures were heated to 60° C. with stirring for the specified time (10 min, 20 min, 30 min, 1 h, etc.). The mixtures were then immediately quenched by the addition of a solution of pH 7 potassium phosphate buffer in D$_2$O (2M, 120 microliters) and were diluted with DMSO-d$_6$ (0.5 mL, containing TMS internal standard). The resulting solutions, once cooled to 23° C., were immediately analyzed by $^1$H NMR. The percent boronic acid remaining was calculated by comparing the ratio of the integrated 4-bromoanisole C—H signal (doublet, 7.41 ppm) to that of the boronic acid C—H signal (doublet, 7.74 ppm). FIG. 5 depicts a graph of the decomposition of 1a over time.

Example 10

Kinetics of Fast-Release of Boronic Acid from MIDA Boronate

To a 1.5 mL vial equipped with a small stir bar was added the 2-furyl MIDA boronate stock solution of Example 6 (100 microliters), followed by a solution of NaOH in D$_2$O (3.0 M, 20 microliters). The mixture was stirred at 60° C. for 10 min. The mixture was diluted with CD$_3$CN (0.5 mL containing TMS internal standard) and was immediately analyzed by $^1$H-NMR. This analysis revealed complete deprotection of the MIDA boronate.

Example 11

Comparison of Fast-Release Cross-Coupling Yields of Boronic Acids Vs. MIDA Boronates To form 2-(4-tert-butoxyphenyl)furan (4a), the general procedure of Example 11 was followed using MIDA boronate 2a (225 mg, 1.00 mmol), except that the aqueous K$_3$PO$_4$ was replaced with 3 M aqueous NaOH (3.0 M, 2.5 mL, degassed by sparging with Ar for 30 min). This reaction afforded 4a as a yellow liquid (127 mg, 59%). A parallel reaction using freshly-prepared boronic acid 1a (112 mg, 1.00 mmol) under otherwise identical conditions afforded 4a as yellow liquid (0.168 g, 64%; yield corrected for residual 3a). This method is depicted in the scheme below.

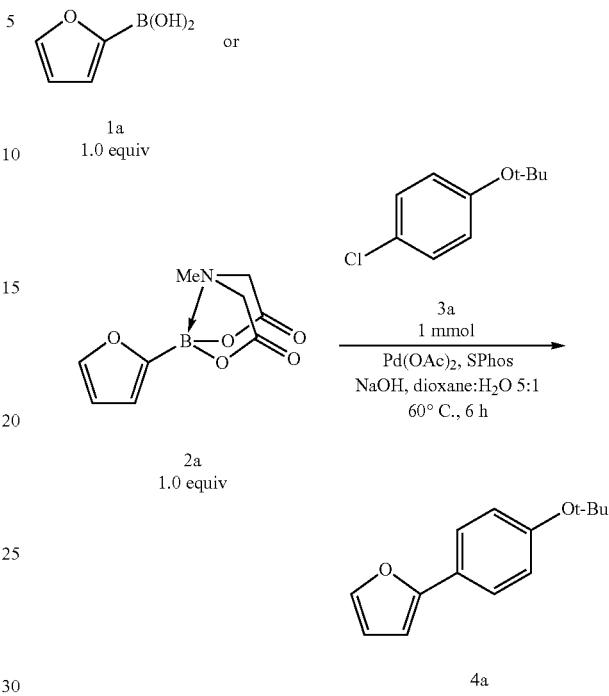

Example 12

Kinetics of Slow-Release of Boronic Acids from MIDA Boronates

Stock solutions of the MIDA boronate and 4-bromoanisole (internal standard) in dioxane-d$_8$ were prepared as follows: 4-tolyl MIDA boronate (Gillis, 2007) (16 mg, 0.064 mmol) and 4-bromoanisole (12 mg, 0.065 mmol) were dissolved in dioxane-d$_8$ (800 microliters); 2-furyl MIDA boronate (2a) (54 mg, 0.24 mmol) and 4-bromoanisole (45 mg, 24 mmol) were dissolved in dioxane-d$_8$ (3.0 mL); vinyl MIDA boronate (2g) (11.7 mg, 0.064 mmol) and 4-bromoanisole (12 mg, 0.065 mmol) were dissolved in dioxane-d$_8$ (800 microliters); cyclopropyl MIDA boronate (2h) (12.8 mg, 0.065 mmol) and 4-bromoanisole (12.0 mg, 0.064 mmol) were dissolved in dioxane-d$_8$ (800 microliters). To each 1.5 mL vial equipped with a small stir bar was added the boronate stock solution (100 microliters) followed by a solution of K$_3$PO$_4$ in D$_2$O (3.0 M, 20 microliters). The mixtures were stirred at the specified temperature (23° C., 60° C., or 100° C.) for the specified time (0.5 h, 1.0 h, 2.0 h, etc.). The mixtures were then immediately cooled to room temperature and were diluted with CD$_3$CN (0.5 mL containing TMS internal standard). The solutions were immediately analyzed by 1H-NMR.

The percent MIDA boronate remaining was calculated by comparing the ratio of the integrated 4-bromoanisole OCH$_3$ singlet (3.76 ppm, internal standard) to that of the MIDA boronate NCH$_3$ singlet (tolyl=2.47 ppm; furyl=2.60 ppm; vinyl=2.77 ppm; cyclopropyl=2.98 ppm). FIG. 6 depicts a graph of the deprotection data for these MIDA boronates. FIG. 7 is a graph of the deprotection data for 2a at 23° C., 60° C. and 100° C. FIG. 8 is a graph of the deprotection data for 2a at 23° C.

Example 13

Cross-Coupling Reaction Performed with Syringe Pump Addition of Organoboronic Acid Under ambient atmosphere, to a 40 mL I-Chem vial equipped with a stir bar was added 1-tert-butoxy-4-chlorobenzene (3a) (0.185 g, 1.00 mmol), dicyclohexylphosphino-2',6'-dimethoxy-1,1'-biphenyl (SPhos) (41 mg, 0.10 mmol) and Pd(OAc)$_2$ (11 mg, 0.050 mmol). The vial was sealed with a PTFE-lined septum screw-cap, and then placed under an Ar atmosphere. To the vial was added dioxane (9.5 mL) and the resulting mixture was stirred at 23° C. for 10 min. To the vial was added aqueous K$_3$PO$_4$ (3.0 M, 2.5 mL, degassed by sparging with Ar for 30 min). The vial was placed in a 60° C. oil bath, and to the stirred mixture was added dropwise over 3 h via syringe pump freshly prepared 2-furylboronic acid (1a) (0.112 g, 1.00 mmol) as a solution in dioxane (3.0 mL). After the addition was complete the reaction mixture was stirred at 60° C. for an additional 3 h. The mixture was cooled to room temperature and was then transferred to a 60 mL separatory funnel and was diluted with aqueous NaOH (1.0 M, 10 mL). The mixture was extracted with Et$_2$O (3×10 mL). The combined organic fractions were dried over MgSO$_4$, filtered and then concentrated in vacuo. The resulting residue was purified by flash chromatography (hexanes:EtOAc, 100:0→9:1) to afford a colorless oil (0.213 g, 98%). This method is depicted in the scheme below.

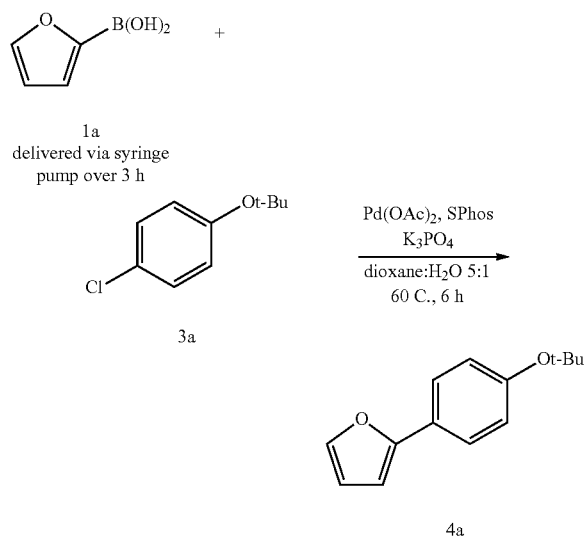

Example 14

Slow-Release Cross-Coupling with MIDA Boronates

The general method for in situ slow-release of MIDA boronates and cross-coupling with organohalides was as follows. Under ambient atmosphere, to a 40 mL I-Chem vial equipped with a stir bar was added the aryl chloride (1.00 mmol), the MIDA boronate (1.20 mmol), dicyclohexylphosphino-2',6'-dimethoxy-1,1'-biphenyl (SPhos) (41 mg, 0.10 mmol) and Pd(OAc)$_2$ (11 mg, 0.050 mmol). The vial was sealed with a PTFE-lined septum screw-cap, and then placed under an Ar atmosphere. To the vial was added dioxane (12.5 mL) and the resulting mixture was stirred at 23° C. for 10 min. To the vial was added aqueous K$_3$PO$_4$ (3.0 M, 2.5 mL, degassed by sparging with Ar for 30 min). The vial was placed in a 60° C. oil bath with stirring for 6 h. The mixture was cooled to room temperature, and was then transferred to a 60 mL separatory funnel and diluted with aqueous NaOH (1.0 M, 10 mL). The mixture was extracted with Et$_2$O (3×10 mL). The combined organic fractions were dried over MgSO$_4$, filtered, and then concentrated in vacuo. The resulting residue was subjected to flash-chromatography on silica gel (hexanes:EtOAc). The yields of cross-coupling are listed in FIGS. 9A and 9B.

To form 2-(2,4-dimethoxyphenyl)furan (4i) (Kang, 1998), the general procedure was followed using 1-chloro-2,4-dimethoxybenzene (3b) (173 mg, 1.00 mmol), 2-furan MIDA boronate (2a) (267 mg, 1.20 mmol), SPhos (41 mg, 0.10 mmol) and Pd(OAc)$_2$ (12 mg, 0.052 mmol) to afford 4i as a pale orange liquid (202 mg, 99%). TLC (hexanes:EtOAc 9:1) R$_f$=0.36, visualized by UV (254 nm). $^1$H-NMR (500 MHz, CDCl$_3$ w/ TMS) δ 7.74 (d, J=8.5 Hz, 1H), 7.41 (d, J=1.0 Hz, 1H), 6.79 (d, J=3.5 Hz, 1H), 6.55 (dd, J=8.5, 2.5 Hz, 1H), 6.52 (d, J=2.0 Hz, 1H), 6.46 (q, J=2.0 Hz, 1H), 3.89 (s, 3H), 3.82 (s, 3H). $^{13}$C-NMR (125 MHz, CDCl$_3$) δ 159.9, 156.5, 150.4, 140.4, 126.8, 113.4, 111.4, 107.8, 104.6, 98.7, 55.4 (2 carbons).

HRMS (EI+) Calculated for C$_{12}$H$_{12}$O$_3$ (M)$^+$: 204.0787, Found: 204.0790. IR (thin film, cm$^{-1}$) 3002, 2960, 2937, 2836, 1614, 1585, 1514, 1468, 1418, 1307, 1288, 1270, 1208, 1160, 1054, 1029, 1003, 827, 798, 735.

To form 2-(2,4,6-trimethylphenyl)furan (4j) (Hashmi, 2006), the general procedure was followed using mesityl chloride (3c) (154 mg, 1.00 mmol), 2-furyl MIDA boronate (2a) (267 mg, 1.20 mmol), SPhos (42 mg, 0.10 mmol) and Pd(OAc)$_2$ (11 mg, 0.049 mmol) to afford 4j as a colorless crystalline solid (181 mg, 97%). TLC (hexanes) R$_f$=0.40, visualized by UV (254 nm). $^1$H-NMR (500 MHz, CDCl$_3$ w/ TMS) δ 7.46 (s, 1H), 6.90 (s, 2H), 6.44 (t, J=3.0 Hz, 1H), 6.23 (d, J=3.0 Hz, 1H), 2.28 (s, 3H), 2.15 (s, 6H). $^{13}$C-NMR (125 MHz, CDCl$_3$) δ 152.4, 141.4, 138.3, 138.3, 128.2, 128.2, 110.3, 109.0, 21.0, 20.4. HRMS (EI+) Calculated for C$_{13}$H$_{14}$O (M)$^+$: 186.1045, Found: 186.1043. IR (thin film, cm$^{-1}$) 2975, 2954, 2919, 1612, 1505, 1473, 1440, 1373, 1257, 1212, 1169, 1148, 1028, 1005, 898, 863, 743.

To form 5-(2-furanyl)-2-methylbenzoxazole (4k), the general procedure was followed using 5-chloro-2-methylbenzoxazole (3d) (168 mg, 1.00 mmol), 2-furyl MIDA boronate (2a) (266 mg, 1.19 mmol), SPhos (41 mg, 0.10 mmol) and Pd(OAc)$_2$ (11 mg, 0.049 mmol) to afford 4k as a pale orange crystalline solid (198 mg, 99%). TLC (hexanes:EtOAc 3:1) R$_f$=0.30, visualized by UV (254 nm). $^1$H-NMR (500 MHz, CDCl$_3$ w/ TMS) δ 7.93 (d, J=1.0 Hz, 1H), 7.61 (dd, J=8.5, 1.5 Hz, 1H), 7.47 (d, J=1.0 Hz, 1H), 7.44 (d, J=8.5 Hz, 1H), 6.63 (d, J=3.5 Hz, 1H), 6.47 (dd, J=3.5, 2.0 Hz, 1H), 2.62 (s, 3H). $^{13}$C-NMR (125 MHz, CDCl$_3$) δ 164.5, 153.7, 150.3, 141.9, 141.9, 127.6, 120.8, 114.6, 111.6, 110.3, 104.6, 14.5. HRMS (EI+) Calculated for C$_{12}$H$_9$NO$_2$ (M)$^+$: 199.0633, Found: 199.0634. IR (KBr, cm$^{-1}$) 2934, 2857, 1576, 1504, 1458, 1383, 1300, 1269, 1228, 1170, 1011, 885, 811.

To form 3-(2-furanyl)-2,5-dimethylpyrazine (4l) (Aoyagi, 1992), the general procedure was followed using 3-chloro-2,5-dimethylpyrazine (3e) (143 mg, 1.00 mmol), 2-furyl MIDA boronate (2a) (267 mg, 1.20 mmol), SPhos (41 mg, 0.10 mmol) and Pd(OAc)$_2$ (11 mg, 0.049 mmol) to afford 4l as a golden liquid (159 mg, 91%). TLC (hexanes:EtOAc 3:1) R$_f$=0.28, visualized by UV (254 nm). $^1$H-NMR (500 MHz, CDCl$_3$ w/ TMS) δ 8.20 (s, 1H), 7.61 (d, J=1.0 Hz, 1H), 7.00 (d, J=3.5 Hz, 1H), 6.54 (dd, J=3.0, 1.5 Hz, 1H), 2.74 (s, 3H), 2.54 (s, 3H). $^{13}$C-NMR (125 MHz, CDCl$_3$) δ 151.7, 150.2, 146.5, 143.9, 142.5, 141.2, 112.3, 111.7, 23.3, 21.2. HRMS (EI+) Calculated for $C_{10}H_{10}N_2O$ (M)$^+$: 174.0793, Found: 174.0799. IR (thin film, cm$^{-1}$) 3116, 3038, 2966, 2926, 2858, 2359, 2228, 1553, 1537, 1449, 1446, 1389, 1357, 1289, 1255, 1220, 1203, 1174, 1149, 1095, 1061, 1012, 973, 928, 886, 867, 821, 735, 596.

To form 2-(2,4-dimethoxyphenyl)benzofuran (4m), the general procedure was followed using 1-chloro-2,4-dimethoxybenzene (3b) (172 mg, 1.00 mmol), 2-benzofuranyl MIDA boronate (2b) (328 mg, 1.20 mmol), SPhos (41 mg, 0.10 mmol) and Pd(OAc)$_2$ (12 mg, 0.051 mmol) to afford 4m as a colorless liquid (239 mg, 94%). TLC (hexanes:EtOAc 9:1) $R_f$=0.25, visualized by UV (254 nm). $^1$H-NMR (500 MHz, CDCl$_3$ w/ TMS) δ 7.97 (d, J=8.5 Hz, 1H), 7.56 (d, J=7.5 Hz, 1H), 7.48 (d, J=7.5 Hz, 1H), 7.24-7.17 (m, 3H), 6.60 (dd, J=8.5, 2.5 Hz, 1H), 6.55 (d, J=2.0 Hz, 1H), 3.95 (s, 3H), 3.84 (s, 3H). $^{13}$C-NMR (125 MHz, CDCl$_3$) δ 160.8, 157.7, 153.6, 152.4, 130.0, 127.9, 123.5, 122.5, 120.7, 112.7, 110.6, 104.8, 104.2, 98.7, 55.4, 55.4. HRMS (EI+) Calculated for $C_{16}H_{14}O_3$ (M)$^+$: 254.0943, Found: 254.0941. IR (thin film, cm$^{-1}$) 3002, 2960, 2937, 2834, 1611, 1586, 1503, 1452, 1291, 1255, 1211, 1160, 1050, 1032, 1013.

To form 5-(2-benzofuranyl)indole (4n) (Kitamura, 2007), the general procedure was followed using 5-chloroindole (3f) (153 mg, 1.01 mmol), 2-benzofuranyl MIDA boronate (2b) (329 mg, 1.20 mmol), SPhos (41 mg, 0.10 mmol) and Pd(OAc)$_2$ (12 mg, 0.053 mmol). The extraction step was modified to use Et$_2$O (10 mL), then EtOAc (2×10 mL). Benzofuran 4n was isolated as a pale yellow solid (220 mg, 94%). TLC (hexanes:EtOAc 3:1) $R_f$=0.31, visualized by UV (254 nm). $^1$H-NMR (500 MHz, acetone-d$_6$) δ 10.44 (br s, 1H), 8.23 (s, 1H), 7.74 (dd, J=8.5, 1.5 Hz, 1H), 7.59 (d, J=7.0 Hz, 1H), 7.56 (app. d, J=8.5 Hz, 2H), 7.41 (t, J=3.0 Hz, 1H), 7.26 (td, J=7.5, 1.0 Hz, 1H), 7.22 (td, J=7.5, 1.0 Hz, 1H), 7.13 (s, 1H), 6.62 (t, J=2.0 Hz, 1H). $^{13}$C-NMR (125 MHz, acetone-d$_6$) δ 158.7, 155.4, 137.4, 130.7, 129.2, 126.9, 124.3, 123.6, 122.6, 121.3, 119.7, 118.0, 112.7, 111.5, 103.1, 100.0. HRMS (EI+) Calculated for $C_{16}H_{11}NO$ (M)$^+$: 233.0841, Found: 233.0843. IR (KBr, cm$^{-1}$) 3439, 1582, 1475, 1458, 1444, 1417, 1332, 1295, 1254, 1020, 1006, 890, 877, 807, 753, 728, 594, 487, 442, 410.

To form 5-(2-benzofuranyl)-2-pyridinamine (4o), the general procedure was followed using 2-amino-5-chloropyridine (3g) (128 mg, 1.00 mmol), 2-benzofuranyl MIDA boronate (2b) (359 mg, 1.50 mmol), SPhos (41 mg, 0.10 mmol) and Pd(OAc)$_2$ (12 mg, 0.052 mmol). The extraction step was modified to use Et$_2$O (10 mL), then EtOAc (2×10 mL). Benzofuran 4o was isolated as a pale orange solid (180 mg, 85%). TLC (EtOAc) $R_f$=0.45, visualized by UV (254 nm). $^1$H-NMR (500 MHz, acetone-d$_6$) δ 8.57 (d, J=2.0 Hz, 1H), 7.89 (dd, J=9.0, 2.5 Hz, 1H), 7.57 (d, J=8.5 Hz, 1H), 7.50 (d, J=8.5 Hz, 1H), 7.24 (td, J=7.5, 1.5 Hz, 1H), 7.20 (td, J=7.5, 1.5 Hz, 1H), 7.03 (d, J=1.0 Hz, 1H), 6.66 (d, J=8.5 Hz, 1H), 5.85 (br s, 2H). $^{13}$C-NMR (125 MHz, acetone-d$_6$) δ 160.8, 155.9, 155.3, 146.1, 134.6, 130.4, 124.4, 123.8, 121.3, 116.6, 111.5, 108.8, 99.4. HRMS (EI+) Calculated for $C_{13}H_{10}N_2O$ (M)$^+$: 210.0793, Found: 210.0793. IR (KBr, cm$^{-1}$) 3436, 3308, 3114, 3106, 2964, 1650, 1614, 1574, 1500, 1451, 1399, 1352, 1321, 1294, 1271, 1254, 1207, 1151, 1142, 1040, 1007, 934, 918, 835, 806, 747, 532, 515, 450, 412.

To form 2-(3-thienyl)benzofuran (4p) (O'Brien, 2006), the general procedure was followed using 3-chlorothiophene (3h) (119 mg, 1.01 mmol), 2-benzofuranyl MIDA boronate (2b) (360 mg, 1.50 mmol), SPhos (41 mg, 0.10 mmol) and Pd(OAc)$_2$ (11 mg, 0.050 mmol) to afford 4p as a colorless solid (171 mg, 85%). TLC (hexanes:EtOAc 9:1) $R_f$=0.53, visualized by UV (254 nm). $^1$H-NMR (500 MHz, CDCl$_3$ w/ TMS) δ 7.67 (d, J=1.5 Hz, 1H), 7.52 (d, J=8.0 Hz, 1H), 7.47 (d, J=8.0 Hz, 1H), 7.40 (d, J=4.5 Hz, 1H), 7.32 (dd, J=4.5, 3.0 Hz, 1H), 7.24 (t, J=7.5 Hz, 1H), 7.19 (t, J=7.5 Hz, 1H), 6.77 (s, 1H). $^{13}$C-NMR (125 MHz, CDCl$_3$) δ 154.5, 152.6, 132.2, 129.0, 126.5, 125.0, 124.0, 122.9, 121.4, 120.8, 111.0, 101.0. HRMS (EI+) Calculated for $C_{12}H_8OS$ (M)$^+$: 200.0296, Found: 200.0295. IR (KBr, cm$^{-1}$) 3100, 1607, 1452, 1280, 1255, 1041, 944, 854, 807, 785, 749, 601, 436.

To form 2-(2,4-dimethoxyphenyl)thiophene (4q) (Littke, 2002), the general procedure was followed using 1-chloro-2,4-dimethoxybenzene (3b) (173 mg, 1.00 mmol), 2-thiophenyl MIDA boronate (2c) (285 mg, 1.19 mmol), SPhos (41 mg, 0.10 mmol) and Pd(OAc)$_2$ (11 mg, 0.051 mmol) to afford 4q as a pale golden liquid (215 mg, 98%). TLC (hexanes:EtOAc 9:1) $R_f$=0.27, visualized by UV (254 nm).

$^1$H-NMR (500 MHz, CDCl$_3$ w/ TMS) δ 7.53 (d, J=9.5 Hz, 1H), 7.37 (d, J=3.5 Hz, 1H), 7.25 (d, J=5.5 Hz, 1H), 7.05 (t, J=4.5 Hz, 1H), 6.53-6.51 (m, 2H), 3.88 (s, 3H), 3.82 (s, 3H). $^{13}$C-NMR (125 MHz, CDCl$_3$) δ 160.1, 156.7, 139.6, 129.3, 126.7, 124.3, 124.2, 116.5, 105.0, 98.9, 55.5, 55.4. HRMS (EI+) Calculated for $C_{12}H_{12}O_2S$ (M)$^+$: 220.0558, Found: 220.0563. IR (thin film, cm$^{-1}$) 3102, 3069, 3000, 3959, 3937, 2835, 1610, 1577, 1528, 1464, 1432, 1417, 1354, 1303, 1273, 1242, 1210, 1160, 1114, 1031, 959, 927, 848, 824, 798, 697, 577.

To form 2-methyl-5-(2-thienyl)benzoxazole (4r), the general procedure was followed using 5-chloro-2-methylbenzoxazole (3d) (168 mg, 1.00 mmol), 2-thiophenyl MIDA boronate (2c) (287 mg, 1.20 mmol), SPhos (41 mg, 0.10 mmol) and Pd(OAc)$_2$ (11 mg, 0.051 mmol) to afford 4r as a crystalline pale yellow solid (213 mg, 99%). TLC (hexanes:EtOAc 3:1) $R_f$=0.35, visualized by UV (254 nm). $^1$H-NMR (500 MHz, CDCl$_3$ w/ TMS) δ 7.85 (d, J=1.0 Hz, 1H), 7.50 (dd, J=8.0, 1.5 Hz, 1H), 7.39 (d, J=8.5 Hz, 1H), 7.26 (d, J=3.0 Hz, 1H), 7.24 (d, J=5.0 Hz, 1H), 7.04 (dd, J=5.0, 3.5 Hz, 1H), 2.59 (s, 3H). $^{13}$C-NMR (125 MHz, CDCl$_3$) δ 164.4, 150.3, 144.0, 142.1, 130.9, 127.9, 124.6, 123.0, 122.8, 116.6, 110.2, 14.4. HRMS (EI+) Calculated for $C_{12}H_9NOS$ (M)$^+$: 215.0405, Found: 215.0403. IR (KBr, cm$^{-1}$) 3098, 3064, 1622, 1577, 1473, 1428, 1380, 1271, 1160, 1050, 923, 867, 798.

To form 2-(2-thienyl)quinoxaline (4s) (Gazit, 1996), the general procedure was followed using 1-chloroisoquinoline (3i) (165 mg, 1.00 mmol), 2-thiophenyl MIDA boronate (2c) (287 mg, 1.20 mmol), SPhos (41 mg, 0.10 mmol) and Pd(OAc)$_2$ (11 mg, 0.050 mmol) to afford 4s as a yellow solid (206 mg, 97%). TLC (hexanes:EtOAc 3:1) $R_f$=0.42, visualized by UV (254 nm). $^1$H-NMR (500 MHz, CDCl$_3$ w/ TMS) δ 9.20 (s, 1H), 8.04 (app d, J=8.0 Hz, 2H), 7.82 (s, 1H), 7.71 (t, J=7.0 Hz, 1H), 7.66 (t, J=7.0 Hz, 1H), 7.52 (d, J=4.0 Hz, 1H), 7.17 (s, 1H). $^{13}$C-NMR (125 MHz, CDCl$_3$) δ 147.2, 142.1, 142.0, 141.9, 141.2, 130.3, 129.7, 129.1, 129.0, 129.0, 128.3, 126.8.

HRMS (EI+) Calculated for $C_{12}H_8N_2S$ (M)$^+$: 212.0408, Found: 212.0407. IR (thin film, cm$^{-1}$) 3118, 3093, 1573, 1547, 1491, 1428, 1321, 1238, 1208, 1134, 1054, 998, 941, 926, 852.

To form N-(tert-butoxycarbonyl)-2-(2,3-dimethoxyphenyl)pyrrole (4t), the general procedure was followed using 1-chloro-2,4-dimethoxybenzene (3b) (87 mg, 0.51 mmol), 2-(N-tert-butoxycarbonyl)pyrrole MIDA boronate (2e) (196 mg, 0.61 mmol), SPhos (20 mg, 0.048 mmol), Pd(OAc)$_2$ (6 mg, 0.03 mmol), K$_3$PO$_4$ (3.0 M, 1.25 mL) and dioxane (6.0 mL) to afford 4t as a very pale yellow oil (124 mg, 81%). TLC (hexanes:EtOAc 3:1) $R_f$=0.59, visualized by UV (254 nm). $^1$H-NMR (500 MHz, CDCl$_3$ w/ TMS) δ 7.32 (s, 1H), 7.17 (d, J=8.0 Hz, 1H), 6.48 (d, J=8.5 Hz, 1H), 6.45 (s, 1H), 6.22 (t, J=3.0 Hz, 1H), 6.10 (s, 1H), 3.82 (s, 3H), 3.72 (s, 3H), 1.36 (s, 9H). $^{13}$C-NMR (125 MHz, CDCl$_3$) δ 160.7, 158.3, 149.4, 131.1, 130.6, 121.6, 117.0, 113.5, 110.2, 103.4, 98.2, 82.6, 55.3, 55.2, 27.6. HRMS (EI+) Calculated for C$_{17}$H$_{21}$NO$_4$ (M)$^+$: 303.1471, Found: 303.1469. IR (thin film, cm$^{-1}$) 2976, 2938, 2834, 1736, 1617, 1584, 1512, 1464, 1437, 1419, 1394, 1370, 1341, 1316, 1209, 1159, 1127, 1034, 974, 840, 726.

To form 5-(N-tert-butoxycarbonyl-pyrrole)-2-methylbenzoxazole (4u), the general procedure was followed using 5-chloro-2-methylbenzoxazole (3d) (84 mg, 0.50 mmol), 2-(N-tert-butoxycarbonyl)pyrrole MIDA boronate (2e) (195 mg, 0.61 mmol), SPhos (21 mg, 0.050 mmol), Pd(OAc)$_2$ (6 mg, 0.03 mmol), K$_3$PO$_4$ (3.0 M, 1.25 mL) and dioxane (6.0 mL) to afford 4u as a very pale yellow oil (146 mg, 98%). TLC (hexanes:EtOAc 3:1) R$_f$=0.42, visualized by UV (254 nm). $^1$H-NMR (500 MHz, CDCl$_3$ w/ TMS) δ 7.63 (s, 1H), 7.43 (d, J=8.5 Hz, 1H), 7.36 (s, 1H), 7.28 (d, J=8.5 Hz, 1H), 6.23 (t, J=3.0 Hz, 1H), 6.20 (s, 1H), 2.64 (s, 3H), 1.34 (s, 9H). $^{13}$C-NMR (125 MHz, CDCl$_3$) δ 164.2, 150.2, 149.1, 140.9, 134.4, 130.6, 126.1, 122.4, 120.0, 114.7, 110.4, 109.0, 83.5, 27.5, 14.5. HRMS (EI+) Calculated for C$_{17}$H$_{18}$N$_2$O$_3$ (M)$^+$: 298.1318, Found: 298.1317. IR (thin film, cm$^{-1}$) 2982, 1739, 1584, 1584, 1456, 1395, 1365, 1370, 1336, 1313, 1264, 1166, 1140, 985, 906, 836, 809.

To form N-phenylsulfonyl-2-(2,3-dimethoxyphenyl)indole (4v), the general procedure was followed using 1-chloro-2,4-dimethoxybenzene (3b) (173 mg, 1.00 mmol), 1-(phenylsulfonyl)indole-2-MIDA boronate (2f) (495 mg, 1.20 mmol), SPhos (42 mg, 0.10 mmol) and Pd(OAc)$_2$ (11 mg, 0.049 mmol) to afford 4v as an off-white solid (382 mg, 97%). TLC (hexanes:EtOAc 3:1) R$_f$=0.37, visualized by UV (254 nm). $^1$H-NMR (500 MHz, acetone-d$_6$) δ 8.19 (d, J=8.0 Hz, 1H), 7.57-7.53 (m, 3H), 7.50 (d, J=7.5 Hz, 1H), 7.43 (t, J=7.5 Hz, 2H), 7.32 (dt, J=7.0, 1.0 Hz, 1H), 7.23 (t, J=7.5 Hz, 1H), 7.17 (d, J=8.0 Hz, 1H), 6.62 (d, J=2.0 Hz, 1H), 6.58 (dd, J=8.0, 2.0 Hz, 1H), 6.56 (s, 1H), 3.87 (s, 3H), 3.72 (s, 3H). $^{13}$C-NMR (125 MHz, acetone-d$_6$) δ 163.0, 160.6, 139.4, 139.3, 138.1, 134.5, 133.2, 131.3, 129.8, 127.4, 125.0, 124.5, 121.5, 116.1, 115.0, 113.0, 104.7, 98.8, 55.7, 55.7. HRMS (EI+) Calculated for C$_{12}$H$_{19}$NO$_4$S (M)$^+$: 393.1035, Found: 393.1036. IR (KBr, cm$^{-1}$) 3000, 2978, 2938, 2842, 1617, 1501, 1449, 1445, 1360, 1284, 1239, 1187, 1163, 1121, 1093, 1069, 1048, 832, 752, 728, 681, 582, 559.

To form 5-(N-phenylsulfonyl-indole)-2-methylbenzoxazole (4w), the general procedure was followed using 5-chloro-2-methylbenzoxazole (3d) (168 mg, 1.00 mmol), 1-(phenylsulfonyl)indole-2-MIDA boronate (2f) (495 mg, 1.20 mmol), SPhos (41 mg, 0.10 mmol) and Pd(OAc)$_2$ (12 mg, 0.052 mmol) to afford 4w as an off-white solid (366 mg, 93%). TLC (hexanes:EtOAc 1:1) R$_f$=0.36, visualized by UV (254 nm). $^1$H-NMR (500 MHz, acetone-d$_6$) δ 8.27 (d, J=8.5 Hz, 1H), 7.78 (d, J=1.0 Hz, 1H), 7.61 (d, J=8.5 Hz, 1H), 7.55 (t, J=7.5 Hz, 1H), 7.51 (d, J=8.0 Hz, 2H), 7.45 (app. d, J=8.0 Hz, 2H), 7.39 (app. t, J=8.0 Hz, 3H), 7.28 (dt, J=7.0, 1.0 Hz, 1H), 6.75 (s, 1H), 2.65 (s, 3H). $^{13}$C-NMR (125 MHz, acetone-d$_6$) δ 165.6, 152.3, 142.9, 142.4, 139.3, 138.6, 134.8, 131.7, 129.9, 129.6, 128.2, 127.5, 125.8, 125.4, 122.0, 121.9, 117.3, 114.9, 110.1, 14.4. HRMS (EI+) Calculated for C$_{22}$H$_{16}$N$_2$O$_3$S (M)$^+$: 388.0882, Found: 388.0880. IR (thin film, cm$^{-1}$) 3063, 3012, 1712, 1623, 1581, 1477, 1449, 1432, 1365, 1262, 1220, 1177, 1157, 1122, 1092, 1065, 1021, 999, 921, 823.

To form 2,4,6-trimethylstyrene (4x) (Lando, 2003), the general procedure was followed using mesityl chloride (3c) (155 mg, 1.01 mmol), vinyl MIDA boronate (2g) (220 mg, 1.20 mmol), SPhos (41 mg, 0.10 mmol) and Pd(OAc)$_2$ (12 mg, 0.051 mmol). The reaction time and temperature were modified so that the reaction mixture was heated to 100° C. for 2 h. Styrene 4x was isolated as a colorless liquid (150 mg, 91%; yield corrected for residual 3c). TLC (hexanes) R$_f$=0.64, visualized by UV (254 nm). $^1$H-NMR (500 MHz, CDCl$_3$ w/ TMS) δ 6.86 (s, 2H), 6.66 (dd, J=18.0, 11.5 Hz, 1H), 5.50 (dt, J=11.5, 2.0 Hz, 1H), 5.23 (dt, J=18.0, 2.0 Hz, 1H), 2.27 (s, 6H), 2.26 (s, 3H). $^{13}$C-NMR (125 MHz, CDCl$_3$) δ 136.1, 135.7, 135.0, 134.8, 128.5, 119.0, 20.9, 20.8. HRMS (EI+) Calculated for C$_{11}$H$_{14}$ (M)$^+$: 146.1096, Found: 146.1098.

IR (thin film, cm$^{-1}$) 3080, 2999, 2952, 2918, 2856, 1631, 1612, 1481, 1442, 1376, 994, 919, 850.

To form 2-vinylquinoxaline (4y), the general procedure was followed using 2-chloroquinoxaline (3i) (165 mg, 1.00 mmol), vinyl MIDA boronate (2g) (219 mg, 1.20 mmol), SPhos (41 mg, 0.10 mmol) and Pd(OAc)$_2$ (11 mg, 0.051 mmol). The reaction time and temperature were modified so that the reaction mixture was heated to 100° C. for 2 h. Following the aqueous workup, the crude residue was subjected to purification on C$_{18}$ silica gel (43g RediSep column) eluting with H$_2$O:THF (95:5→55:45, 24 mL/min over 25 min) to afford 4y as an orange oil (133 mg, 87%). TLC (hexanes:EtOAc 3:1) R$_f$=0.31, visualized by UV (254 nm). $^1$H-NMR (500 MHz, CDCl$_3$ w/ TMS) δ 9.00 (s, 1H), 8.08 (app. t, J=9.0 Hz, 2H), 7.77-7.70 (m, 2H), 7.04 (dd, J=17.5, 11.0 Hz, 1H), 6.48 (d, J=17.5 Hz, 1H), 5.79 (d, J=11.0 Hz, 1H).

$^{13}$C-NMR (125 MHz, CDCl$_3$) δ 150.4, 143.5, 142.1, 141.7, 134.8, 130.2, 129.5, 129.3, 129.1, 122.1. HRMS (ESI+) Calculated for C$_{10}$H$_9$N$_2$ (M+H)$^+$: 157.0766, Found: 157.0768. IR (thin film, cm$^{-1}$) 3064.0, 3018, 2928, 2847, 1631, 1596, 1546, 1492, 1466, 1414, 1365, 1342, 1331, 1303, 1282, 1258, 1212, 1185, 1121, 1065, 1014, 989, 972, 927, 762.

To form 2-amino-5-vinylpyridine (4z), the general procedure was followed using 2-amino-5-chloropyridine (3g) (129 mg, 1.00 mmol), vinyl MIDA boronate (2g) (220 mg, 1.20 mmol), SPhos (42 mg, 0.10 mmol) and Pd(OAc)$_2$ (11 mg, 0.050 mmol). The reaction time and temperature were modified so that the reaction mixture was heated to 100° C. for 2 h. The extraction step was modified to use Et$_2$O (10 mL), then EtOAc (2×10 mL). Pyridine 4z was isolated as a pale orange crystalline solid (91 mg, 76%). TLC (EtOAc) R$_f$=0.48, visualized by UV (254 nm). $^1$H-NMR (500 MHz, CDCl$_3$ w/ TMS) δ 8.05 (s, 1H), 7.56 (dd, J=8.5, 2.0 Hz, 1H), 6.58 (dd, J=17.5, 11.0 Hz, 1H), 6.48 (d, J=9.0 Hz, 1H), 5.56 (d, J=17.5 Hz, 1H), 5.11 (d, J=11.0 Hz, 1H), 4.60 (br s, 2H). $^{13}$C-NMR (125 MHz, CDCl$_3$) δ 157.9, 147.0, 134.4, 133.3, 124.0, 111.2, 108.5. HRMS (EI+) Calculated for C$_7$H$_8$N$_2$ (M)$^+$: 120.0688, Found: 120.0688. IR (KBr, cm$^{-1}$) 3448, 3296, 3128, 1631, 1599, 1509, 1388, 1324, 1274, 1144, 1002, 888, 828.

To form 5-vinyl-2-methylbenzoxazole (4aa), the general procedure was followed using 5-chloro-2-methylbenzoxazole (3d) (167 mg, 1.01 mmol), vinyl MIDA boronate (2g) (218 mg, 1.19 mmol), SPhos (42 mg, 0.10 mmol) and Pd(OAc)$_2$ (11 mg, 0.050 mmol). The reaction time and temperature were modified so that the reaction mixture was heated to 100° C. for 2 h. Benzoxazole 4aa was isolated as a pale golden liquid (152 mg, 96%). TLC (hexanes:EtOAc 3:1) R$_f$=0.46, visualized by UV (254 nm).

$^1$H-NMR (500 MHz, CDCl$_3$ w/ TMS) δ 7.67 (s, 1H), 7.38 (d, J=8.0 Hz, 1H), 7.34 (d, J=8.0 Hz, 1H), 6.79 (dd, J=17.5, 11.0 Hz, 1H), 5.74 (d, J=17.5 Hz, 1H), 5.24 (d, J=11.0 Hz, 1H), 2.61 (s, 3H). $^{13}$C-NMR (125 MHz, CDCl$_3$) δ 164.3, 150.6, 141.9, 136.5, 134.2, 122.9, 116.8, 113.4, 109.9, 14.5. HRMS (EI+) Calculated for C$_{10}$H$_9$NO (M)$^+$: 159.0684, Found: 159.0685. IR (KBr, cm$^{-1}$) 3087, 3006, 2984, 2928, 1623, 1622, 1578, 1477, 1433, 1381, 1335, 1262, 1179, 1114, 1040, 989, 918, 881, 840, 815.

To form 2,4,6-trimethyl-cyclopropylbenzene (4bb) (Lemhadri, 2006), the general procedure was followed using mesityl chloride (3c) (155 mg, 1.00 mmol), cyclopropyl MIDA boronate (2h) (296 mg, 1.50 mmol), SPhos (42 mg, 0.10 mmol) and Pd(OAc)$_2$ (11 mg, 0.047 mmol). The reaction time and temperature were modified so that the reaction mixture was heated to 100° C. for 24 h. Compound 4bb was isolated as a colorless liquid (127 mg, 79%). TLC (hexanes) R$_f$=0.66, visualized by UV (254 nm). $^1$H-NMR (500 MHz, CDCl$_3$ w/ TMS) δ 6.81 (s, 2H), 2.38 (s, 6H), 2.24 (s, 3H), 1.64 (m, 1H), 0.96 (m, 2H), 0.49 (m, 2H). $^{13}$C-NMR (125 MHz, CDCl$_3$) δ 138.8, 136.0, 135.5, 128.6, 20.8, 20.5, 11.7, 8.0. HRMS (EI+) Calculated for C$_{12}$H$_{16}$ (M)$^+$: 160.1252, Found: 160.1252. IR (thin film, cm$^{-1}$) 3080, 3003, 2969, 2954, 2918, 2859, 1612, 1485, 1457, 1375, 1223, 1057, 1025, 901, 850, 814.

To form 2,4-dimethoxy-cyclopropylbenzene (4cc), the general procedure was followed using 1-chloro-2,4-dimethoxybenzene (3b) (173 mg, 1.00 mmol), cyclopropyl MIDA boronate (2h) (236 mg, 1.20 mmol), SPhos (41 mg, 0.10 mmol) and Pd(OAc)$_2$ (11 mg, 0.048 mmol). The reaction temperature was modified so that the reaction mixture was heated to 100° C. for 6 h. Compound 4cc was isolated as a colorless liquid (175 mg, 97%). TLC (hexanes:EtOAc 9:1) R$_f$=0.65, visualized by UV (254 nm). $^1$H-NMR (500 MHz, CDCl$_3$ w/ TMS) δ 6.77 (d, J=8.5 Hz, 1H), 6.44 (d, J=2.5 Hz, 1H), 6.39 (dd, J=8.5, 2.5 Hz, 1H), 3.83 (s, 3H), 3.77 (s, 3H), 2.03 (m, 1H), 0.85 (m, 2H), 0.57 (m, 2H). $^{13}$C-NMR (125 MHz, CDCl$_3$) δ 159.2, 158.6, 125.7, 124.2, 103.8, 98.4, 55.5, 55.3, 9.0, 6.9. HRMS (EI+) Calculated for C$_{11}$H$_{14}$O$_2$ (M)$^+$: 178.0994, Found: 178.0995. IR (thin film, cm$^{-1}$) 3080, 3000, 2955, 2940, 2835, 1615, 1585, 1510, 1464, 1439, 1416, 1370, 1319, 1290, 1261, 1209, 1172, 1158, 1117, 1062, 1037, 938, 884, 834, 823, 799.

Example 15

Slow-Release Cross-Coupling of 2-Pyridyl MIDA Boronate

The general method for in situ slow-release of 2-pyridyl MIDA boronate 2i and cross-coupling with organohalides was as follows. Under ambient atmosphere, to a 15 mL vial equipped with a stir bar was added the halide (1.0 mmol), 2-pyridyl MIDA boronate (2i) (1.5 mmol), K$_2$CO$_3$ (5.0 mmol) and Cu(OAc)$_2$ (0.50 mmol). The vial was transferred to a glove box. In the glove box, to 8.0 mL of a 4:1 mixture of DMF and IPA (DMF:IPA 4:1) was added 2-dicyclohexylphosphino-2',4',6'-triisopropyl-biphenyl (X-Phos) (0.06 mmol) and Pd$_2$dba$_3$ (0.015 mmol). The mixture was premixed and incubated for 5 min at 100° C., and then transferred to the vial at ~40° C. to avoid incomplete solubility at room temperature. The resulting reaction mixture was stirred at 100° C. for 4 h. The mixture was cooled to room temperature and then was transferred to a 60 mL separatory funnel and was diluted with aqueous NaOH (1.0 M, 10 mL). The mixture was extracted with Et$_2$O (3×10 mL). The combined organics were dried over MgSO$_4$, filtered and concentrated in vacuo. The crude residue was subjected to flash-chromatography on silica gel (hexanes:EtOAc). The yields of cross-coupling are listed in FIG. 10.

To form 4-(2-pyridinyl)acetophenone (4dd) (Hitchcock, 1995), the general procedure was followed using 4-chloroacetophenone (3k) (155 mg, 1.00 mmol), 2-pyridyl MIDA boronate (2i) (349 mg, 1.49 mmol), K$_2$CO$_3$ (694 mg, 5.02 mmol) and Cu(OAc)$_2$ (90 mg, 0.50 mmol). Flash chromatography on silica gel (hexanes:EtOAc, 100:0→80:20) afforded 4dd as a colorless solid (142 mg, 72%). TLC (hexanes:EtOAc 1:1) R$_f$=0.47, visualized by UV (254 nm). $^1$H-NMR (500 MHz, CDCl$_3$) δ 8.73 (d, J=5.0 Hz, 1H), 8.10 (d, J=8.5 Hz, 2H), 8.06 (d, J=8.5 Hz, 2H), 7.79 (m, 2H), 7.29 (q, J=4.5 Hz, 1H), 2.65 (s, 3H). $^{13}$C-NMR (125 MHz, CDCl$_3$) δ 197.8, 156.0, 149.9, 143.5, 137.1, 136.9, 128.8, 127.0, 122.9, 121.0, 26.7. HRMS (CI+) Calculated for C$_{13}$H$_{12}$ON (M+H)$^+$: 198.0919, Found: 198.0919. IR (KBr, cm$^{-1}$) 3048, 2999, 1679, 1604, 1584, 1574, 1558, 1466, 1434, 1400, 1356, 1315, 1266, 1156, 1113, 1013, 989, 960, 849, 785, 723, 696, 618, 600, 592.

To form 4-(2-pyridinyl)benzonitrile (4ee) (Billingsley, 2008), the general procedure was followed using 4-chlorobenzonitrile (3k) (137 mg, 1.00 mmol), 2-pyridyl MIDA boronate (2i) (352 mg, 1.50 mmol), K$_2$CO$_3$ (693 mg, 5.01 mmol) and Cu(OAc)$_2$ (91 mg, 0.50 mmol). Flash chromatography on silica gel (hexanes:EtOAc, 9:1) afforded 4ee as a pale yellow solid (109 mg, 60%). TLC (hexanes:EtOAc 1:1) R$_f$=0.59, visualized by UV (254 nm). $^1$H-NMR (500 MHz, CDCl$_3$) δ 8.73 (d, J=5.0 Hz, 1H), 8.11 (d, J=9.0 Hz, 2H), 7.81 (td, J=7.5, 1.5 Hz, 1H), 7.75 (m, 3H), 7.31 (ddd, J=7, 4.5, 1 Hz, 1H). $^{13}$C-NMR (125 MHz, CDCl$_3$) δ 155.2, 150.0, 143.4, 137.1, 132.5, 127.4, 123.3, 121.0, 118.8, 112.5. HRMS (CI+) Calculated for C$_{12}$H$_9$N$_2$ (M+H)$^+$: 181.0766, Found: 181.0765. IR (KBr, cm$^{-1}$) 2228, 1588, 1466, 1433, 1393, 1303, 1152, 1152, 990, 852, 776, 738, 718, 620, 563, 518.

To form 2-(2-pyridinyl)quinoxaline (4ff) (Cui, 2005), the general procedure was followed using 2-chloroquinoxaline (3i) (165 mg, 1.00 mmol), 2-pyridyl MIDA boronate (2i) (353 mg, 1.51 mmol), K$_2$CO$_3$ (693 mg, 5.01 mmol) and Cu(OAc)$_2$ (91 mg, 0.50 mmol). Flash chromatography on silica gel (hexanes:EtOAc, 100:0→80:20) afforded 4ff as a pale orange solid (164 mg, 79%). TLC (hexanes:EtOAc 1:1) R$_f$=0.56, visualized by UV (254 nm). $^1$H-NMR (500 MHz, CDCl$_3$) δ 9.95 (s, 1H), 8.77 (ddd, J=5.0, 1.5, 1.0 Hz, 1H), 8.58 (d, J=8.0 Hz, 1H), 8.15 (m, 2H), 7.88 (td, J=7.5, 1.5 Hz, 1H), 7.77 (m, 2H), 7.39 (ddd, J=7.5, 4.5, 1.0 Hz, 1H). $^{13}$C-NMR (125 MHz, CDCl$_3$) δ 154.5, 150.1, 149.4, 144.1, 142.5, 141.7, 137.1, 130.1, 130.0, 129.7, 129.3, 124.6, 122.0. HRMS (CI+) Calculated for C$_{13}$H$_{10}$N$_3$ (M+H)$^+$: 208.0875, Found: 208.0871. IR (KBr, cm$^{-1}$) 3050, 3004, 1591, 1548, 1492, 1479, 1457, 1437, 1403, 1367, 1143, 1131, 1059, 1043, 996, 961, 806, 785, 772, 742, 716, 670, 556.

To form 2,5-dimethyl-3-(2-pyridinyl)pyrazine (4gg), the general procedure was followed using 3-chloro-2,5-dimethylpyrazine (3e) (142 mg, 1.00 mmol), 2-pyridyl MIDA boronate (2i) (352 mg, 1.50 mmol), K$_2$CO$_3$ (694 mg, 5.02 mmol) and Cu(OAc)$_2$ (90 mg, 0.50 mmol). The aqueous phase was extracted an additional time with EtOAc (10 mL). Flash chromatography on silica gel (hexanes:EtOAc, 100:0→55:45) afforded 4gg as a pale amber liquid (96 mg, 52%). TLC (hexanes:EtOAc 1:1) R$_f$=0.39, visualized by UV (254 nm). $^1$H-NMR (500 MHz, CDCl$_3$ w/TMS) δ 8.72 (d, J=3.5 Hz, 1H), 8.38 (s, 1H), 7.83 (m, 2H), 7.33 (m, 1H), 2.73 (s, 3H), 2.59 (s, 3H). $^{13}$C-NMR (125 MHz, CDCl$_3$) δ 157.2, 150.2, 149.9, 149.4, 148.7, 142.6, 136.6, 124.1, 123.0, 120.1, 22.6, 21.0. HRMS (CI+) Calculated for C$_{11}$H$_{12}$N$_3$ (M+H)$^+$: 186.1031, Found: 186.1034.

IR (thin film, cm$^{-1}$) 3055, 2927, 1693, 1589, 1561, 1474, 1452, 1422, 1371, 1292, 1171, 1071, 1048, 995, 804, 752, 744.

To form 1-(2-pyridinyl)isoquinoline (4hh), the general procedure was followed 1-chloroisoquinoline (31) (164 mg, 1.00 mmol), 2-pyridyl MIDA boronate (2i) (350 mg, 1.49 mmol), K$_2$CO$_3$ (697 mg, 5.05 mmol) and Cu(OAc)$_2$ (89 mg, 0.49 mmol). The aqueous phase was extracted an additional time with EtOAc (10 mL). Flash chromatography on silica gel (hexanes:EtOAc, 70:30→30:70) afforded 4hh as an off-white solid (152 mg, 74%). TLC (EtOAc) $R_f$=0.47, visualized by UV (254 and 366 nm).

$^1$H-NMR (500 MHz, CDCl$_3$) δ 8.79 (ddd, J=5.0, 1.5, 1.0 Hz, 1H), 8.63 (d, J=5.5 Hz, 1H), 8.60 (d, J=8.5 Hz, 1H), 7.99 (dt, J=8.0 Hz, 1.0 Hz, 1H), 7.91 (td, J=7.5, 2.0 Hz, 1H), 7.87 (d, J=8.0 Hz, 1H), 7.70 (d, J=5.5 Hz, 1H), 7.69 (ddd, J=8.0, 7.0, 1.5, 1H), 7.59 (ddd, J=8.5, 7.0, 1 Hz, 1H), 7.40 (ddd, J=7.5, 5.0, 1.0 Hz, 1H). $^{13}$C-NMR (125 MHz, CDCl$_3$) δ 158.2, 157.6, 148.6, 141.8, 137.0, 136.9, 130.0, 127.7, 127.6, 126.8, 126.6, 125.2, 123.2, 121.2. HRMS (CI+) Calculated for C$_{14}$H$_{11}$N$_2$ (M+H)$^+$: 207.0922; Found: 207.0926. IR (KBr, cm$^{-1}$) 3051, 3012, 1581, 1562, 1551, 1470, 1455, 1434, 1379, 1350, 1322, 1245, 1129, 1095, 992, 979, 966, 826, 811, 780, 753, 742, 713, 674, 644, 618, 573, 465, 441.

Example 16

Slow-Release Cross-Coupling of MIDA Boronates with Aryl Bromides and Aryl Chlorides The general method for in situ slow-release of MIDA boronates and cross-coupling with aryl bromides and aryl chlorides was as follows. In a glove box, to a first vial equipped with a stir bar was added 2-dicyclohexylphosphino-2',6'-dimethoxy-1,1'-biphenyl (SPhos), followed by a 0.02 M solution of Pd(OAc)$_2$ in THF in a volume sufficient to afford a 0.04 M solution with respect to the phosphine ligand. The first vial was sealed with a PTFE-lined screwcap and stirred at 23° C. for 30 minutes during which time the orange solution became yellow. Under ambient atmosphere, to a second vial (20 mL) equipped with a stir bar was added the organohalide (1.0 mmol), solid base (7.5 mmol), and the MIDA boronate (1.5 mmol). The second vial was brought into a glove box, and to it was added THF (9.0 mL) and the catalyst stock solution (1.0 mL) from the first vial. The second vial was sealed with a PTFE-lined septum-screwcap and was removed from the glove box, and to the vial was added degassed H$_2$O (2 mL, sparged with Ar for 30 min.). The resulting biphasic mixture was maintained, with vigorous stirring, at 60° C. for 24 h. The reaction mixture was allowed to cool to 23° C. and then was transferred to a 60 mL separatory funnel. The mixture was diluted with aq. 1M NaOH (10 mL) and Et$_2$O (10 mL), shaken, and then the phases were separated. The aqueous phase was extracted with Et$_2$O (3×10 mL). The combined organic phases were washed with brine (10 mL), were dried over MgSO$_4$ and were then filtered. The filtrate was concentrated in vacuo and the resulting residue was subjected to flash chromatography on silica gel, unless otherwise noted. The yields of the cross-coupling are listed in FIG. 11.

To form cross-coupled product 6a, 1-(4-(furan-2-yl)phenyl)ethanone, the general procedure was followed using 4-bromoacetophenone (0.200 g, 1.00 mmol), MIDA boronate 2a (0.336 g, 1.51 mmol), and K$_3$PO$_4$.H$_2$O (1.733 g, 7.53 mmol). The product was eluted with 100% CH$_2$Cl$_2$ to afford 6a as a pale yellow solid (0.183 g, 98%). TLC (hexanes: EtOAc 6:1) $R_f$=0.25, visualized by UV (254 and 366 nm) and KMnO$_4$. $^1$H-NMR (500 MHz, CDCl$_3$) δ 7.98 (d, J=8 Hz, 2H), 7.75 (d, J=8 Hz, 2H), 7.53 (d, J=2 Hz, 1H), 6.80 (d, J=3.5 Hz, 1H), 6.52 (dd, J=3.5, 2 Hz, 1H), 2.61 (s, 3H). $^{13}$C-NMR (125 MHz, CDCl$_3$) δ 197.3, 152.8, 143.2, 135.5, 134.8, 128.9, 123.5, 112.0, 107.4, 26.5. HRMS (CI+) Calculated for C$_{12}$H$_{11}$O$_2$ (M+H)$^+$: 187.0759; Found: 187.0756. IR (thin film, cm$^{-1}$) 3110, 1669, 1609, 1475, 1416, 1378, 1299, 1223, 1120, 1079, 1020, 1010, 905, 839, 821.

To form cross-coupled product 6b, 2-(4-methoxyphenyl)furan, the general procedure was followed using 4-bromoanisole (0.188 g, 1.01 mmol), MIDA boronate 2a (0.336 g, 1.51 mmol), and K$_3$PO$_4$.H$_2$O (1.732 g, 7.52 mmol). The product was eluted with hexanes: CH$_2$Cl$_2$ 3:1 to afford 6b as a colorless solid (0.164 g, 94%). TLC (hexanes:EtOAc 6:1) $R_f$=0.46, visualized by UV (254 nm) and KMnO$_4$. $^1$H-NMR (500 MHz, CDCl$_3$) δ 7.63 (d J=9.0 Hz, 2H), 7.45 (dd, J=2.0, 1.0 Hz, 1H), 6.94 (d, J=9.0 Hz, 2H), 6.53 (dd, J=3.0, 0.5 Hz, 1H), 6.46 (dd, J=3.5, 2.0 Hz, 1H), 3.84 (s, 3H). $^{13}$C-NMR (125 MHz, CDCl$_3$) δ 158.9, 154.0, 141.3, 125.2, 123.9, 114.0, 111.5, 103.3, 55.2. HRMS (EI+) Calculated for C$_{11}$H$_{10}$O$_2$ (M)$^+$: 174.0681; Found: 174.0682. IR (thin film, cm$^{-1}$) 2960, 2836, 1676, 1598, 1513, 1484, 1465, 1441, 1297, 1251, 1175, 1113, 1078, 1025, 902, 884, 833.

To form cross-coupled product 6c, 2-p-tolylfuran, the general procedure was followed using 4-chlorotoluene (0.128 g, 1.01 mmol), MIDA boronate 2a (0.336 g, 1.51 mmol), and K$_3$PO$_4$.H$_2$O (1.740 g, 7.56 mmol). The product was eluted with hexanes to afford 6c as a colorless liquid (0.150 g, 94%). TLC (hexanes): $R_f$=0.37, visualized by UV (254 nm) and KMnO$_4$. $^1$H-NMR (500 MHz, CDCl$_3$) δ 7.58 (d, J=8.5 Hz, 2H), 7.45 (dd, J=1.5, 0.5 Hz, 1H), 7.20 (d, J=7.5 Hz, 2H), 6.60 (d, J=3.5 Hz, 1H), 6.47 (dd, J=3.0, 1.5 Hz, 1H), 2.37 (s, 3H). $^{13}$C-NMR (125 MHz, CDCl$_3$) δ 154.2, 141.6, 137.1, 129.3, 128.2, 123.7, 111.5, 104.2, 21.2. HRMS (ESI+) Calculated for C$_{11}$H$_{11}$O (M+H)$^+$: 159.0810; Found: 159.0806. IR (thin film, cm$^{-1}$) 3115, 3030, 2920, 2860, 1903, 1793, 1718, 1653, 1597, 1516, 1485, 1449, 1412, 1376, 1311, 1279, 1217, 1184, 1157, 1121, 1111, 1079, 1042, 1018, 1008, 943, 903, 885, 821.

To form cross-coupled product 6d, 1-(4-(benzofuran-2-yl)phenyl)-ethanone, the general procedure was followed using 4-bromoacetophenone (0.200 g, 1.00 mmol), MIDA boronate 2b (0.411 g, 1.51 mmol), and K$_3$PO$_4$.H$_2$O (1.733 g, 7.53 mmol). The product was eluted with a gradient of hexanes: CH$_2$Cl$_2$ 1:1→0:100 to afford 6d as a colorless solid (0.233 g, 98%). TLC (hexanes:EtOAc 6:1): $R_f$=0.23, visualized by UV (254 and 366 nm) and KMnO$_4$. $^1$H-NMR (500 MHz, CDCl$_3$) δ 8.04 (d, J=8.5 Hz, 2H), 7.95 (d, J=8.5 Hz, 2H), 7.62 (d, J=7.5 Hz, 1H), 7.55 (app. d, J=8.5 Hz, 1H), 7.34 (td, J=8, 1 Hz, 1H), 7.26 (td, J=8, 1 Hz, 1H), 7.17 (s, 1H), 2.64 (s, 3H). $^{13}$C-NMR (125 MHz, CDCl$_3$) δ 197.3, 155.1, 154.5, 136.4, 134.5, 128.9, 125.1, 124.7, 123.2, 121.3, 111.3, 103.6, 103.6, 26.6. HRMS (CI+) Calculated for C$_{16}$H$_{13}$O$_2$ (M+H)$^+$: 237.0916; Found: 237.0915. IR (thin film, cm$^{-1}$) 2920, 1676, 1450, 1423, 1408, 1358, 1305, 1272, 1110, 1076, 1031, 917, 882, 832.

To form cross-coupled product 6e, 2-(4-methoxyphenyl)benzofuran, the general procedure was followed using 4-bromoanisole (0.187 g, 1.00 mmol), MIDA boronate 2b (0.410 g, 1.50 mmol), and K$_3$PO$_4$.H$_2$O (1.730 g, 7.51 mmol). The product was eluted with hexanes:CH$_2$Cl$_2$ 3:1 to afford 6e as a colorless solid (0.216 g, 96%). TLC (hexanes:EtOAc 6:1): $R_f$=0.43, visualized by UV (254 nm) and KMnO$_4$. $^1$H-NMR (500 MHz, CDCl$_3$) δ 7.81 (d, J=9.0 Hz, 2H), 7.56 (ddd, J=7.5, 1.5, 1.0 Hz, 1H), 7.51 (m, 1H), 7.26 (td, J=7.5, 1.5 Hz, 1H), 7.22 (td, J=7.5, 1.5 Hz, 1H), 6.99 (d, J=9.0 Hz, 2H), 6.89 (d, J=0.5 Hz, 1H), 3.87 (s, 3H). $^{13}$C-NMR (125 MHz, CDCl$_3$) δ 159.9, 156.0, 154.7, 129.5, 126.4, 123.7, 123.3, 122.8, 120.5, 114.2, 111.0, 99.6, 55.3. HRMS (EI+) Calculated for C$_{15}$H$_{12}$O$_2$ (M)$^+$: 224.0837; Found: 224.0838. IR (thin film, cm$^{-1}$) 2958, 2836, 1611, 1598, 1507, 1453, 1297, 1252, 1183, 1112, 1040, 1023, 932, 919, 886, 835, 817.

To form cross-coupled product 6f, 2-p-tolylbenzofuran, the general procedure was followed using 4-chlorotoluene (0.127 g, 1.00 mmol), MIDA boronate 2b (0.410 g, 1.50 mmol), and K$_3$PO$_4$.H$_2$O (1.727 g, 7.50 mmol). The product was eluted with hexanes:EtOAc (100:0→90:10) to afford 6f as a colorless solid (0.198 g, 95%). TLC (hexanes:EtOAc 4:1): $R_f$=0.35, visualized by UV (254 and 280 nm).

$^1$H-NMR (500 MHz, CDCl$_3$) δ 7.72 (d, J=8.0 Hz, 2H), 7.53 (d, J=8.0 Hz, 1H), 7.49 (d, J=8.0 Hz, 1H), 7.26-7.16 (m, 4H), 6.90 (s, 1H), 2.35 (s, 3H). $^{13}$C-NMR (125 MHz, CDCl$_3$) δ 156.1, 154.7, 138.5, 129.4, 129.3, 127.7, 124.8, 123.9, 122.8, 120.7, 111.0, 100.5, 21.3. HRMS (ESI+) Calculated for C$_{15}$H$_{13}$O (M+H)$^+$: 209.0966; Found: 209.0968. IR (thin film, cm$^{-1}$) 2933, 1306, 1255, 1205, 1169, 1110, 1033, 919, 823.

To form cross-coupled product 6g, 1-(4-(thiophen-2-yl)phenyl)ethanone, the general procedure was followed using 4-bromoacetophenone (0.201 g, 1.01 mmol), MIDA boronate 2c (0.361 g, 1.51 mmol), and K$_3$PO$_4$.H$_2$O (1.74 g, 7.56 mmol). For this reaction, a catalyst stock of Pd(PPh$_3$)$_4$ (0.02 M in THF) was used. The product was eluted with hexanes:CH$_2$Cl$_2$:EtOAc 75:20:5 to afford 6g as a colorless solid (0.194 g, 95%). TLC (hexanes:EtOAc 6:1): $R_f$=0.24, visualized by UV (254 and 355 nm).

$^1$H-NMR (500 MHz, CDCl$_3$) δ 7.97 (d, J=9 Hz, 2H), 7.70 (d, J=8.5 Hz, 2H), 7.43 (dd, J=3.5, 1.0 Hz, 1H), 7.37 (dd, J=5.0, 1.0 Hz, 1H), 7.12 (dd, J=5.0, 3.5 Hz, 1H), 2.61 (s, 3H). $^{13}$C-NMR (125 MHz, CDCl$_3$) δ 197.2, 142.9, 138.7, 135.7, 129.1, 128.3, 126.4, 125.6, 124.6, 26.5. HRMS (EI+) Calculated for C$_{12}$H$_{10}$OS (M)$^+$: 202.0452; Found: 202.0448. IR (thin film, cm$^{-1}$) 1678, 1424, 1410, 1359, 1116, 849, 821, 713.

To form cross-coupled product 6h, 2-(4-methoxyphenyl)thiophene, the general procedure was followed using 4-bromoanisole (0.188 g, 1.01 mmol), MIDA boronate 2c (0.360 g, 1.51 mmol), and K$_3$PO$_4$.H$_2$O (1.736 g, 7.54 mmol). The product was eluted with hexanes:EtOAc (100:0→90:10) to afford 6h as a colorless solid (0.188 g, 98%). TLC (hexanes): $R_f$=0.18, visualized by UV (254 nm). $^1$H-NMR (500 MHz, CDCl$_3$) δ 7.56 (d, J=9 Hz, 2H), 7.22-7.24 (m, 2H), 7.07 (dd, J=5, 4 Hz, 1H), 6.94 (d, J=9 Hz, 2H), 3.85 (s, 3H). $^{13}$C-NMR (125 MHz, CDCl$_3$) δ 159.1, 144.3, 127.9, 127.2, 127.2, 123.8, 122.0, 114.2, 55.3. HRMS (ESI+) Calculated for C$_{11}$H$_{11}$OS (M+H)$^+$: 191.0531; Found: 191.0525. IR (thin film, cm$^{-1}$) 3097, 3084, 3067, 2960, 2937, 2912, 2832, 1607, 1530, 1502, 1465, 1430, 1293, 1263, 1185, 1113, 1032, 850, 821, 810.

To form cross-coupled product 6i, 2-p-tolylthiophene, the general procedure was followed using 4-chlorotoluene (0.127 g, 1.00 mmol), MIDA boronate 2c (0.359 g, 1.50 mmol), and K$_3$PO$_4$.H$_2$O (1.727 g, 7.50 mmol). The product was eluted with hexanes to afford 6i as a colorless solid (0.153 g, 88%). TLC (hexanes): $R_f$=0.47, visualized by UV (254 and 280 nm). $^1$H-NMR (500 MHz, CDCl$_3$) δ 7.49 (d, J=7.5 Hz, 2H), 7.24 (d, J=4.0 Hz, 1H), 7.20 (d, J=5.0 Hz, 1H), 7.15 (d, J=8.0 Hz, 2H), 7.03 (ddd, J=5.0, 3.5, 1.5 Hz, 1H), 2.34 (s, 3H). $^{13}$C-NMR (125 MHz, CDCl$_3$) δ 144.5, 137.2, 131.6, 129.5, 127.9, 125.8, 124.2, 122.5, 21.1. HRMS (EI+) Calculated for C$_{11}$H$_{10}$S (M)$^+$: 174.0503; Found: 174.0503. IR (thin film, cm$^{-1}$) 3075, 3023, 2935, 1901, 1789, 1651, 1568, 1532, 1501, 1431, 1407, 1377, 1352, 1313, 1259, 1211, 1188, 1123, 1107, 1080, 1052, 1018, 958, 944, 896, 850, 809.

To form cross-coupled product 6j, trithiophene, the general procedure was followed using 2-bromo-5-methylthiophene 5d (0.178 g, 1.01 mmol), MIDA boronate 2d (0.505 g, 1.51 mmol), and K$_3$PO$_4$.H$_2$O (1.738 g, 7.55 mmol). The product was subjected to flash chromatography on C$_{18}$ silica gel (MeCN:H$_2$O 4:1→100:0) to afford the 6j as a yellow solid (0.246 g, 89%). TLC (hexanes:EtOAc 6:1): $R_f$=0.59, visualized by UV (254 and 366 nm) and KMnO$_4$. $^1$H-NMR (500 MHz, CDCl$_3$) δ 7.03 (d, J=4.0 Hz, 1H), 6.98 (s, 1H), 6.98 (d, J=2.0 Hz, 1H), 6.96 (d, J=3.5 Hz, 1H), 6.79 (m, 1H), 6.67 (m, 1H), 2.49 (d, J=1.0 Hz, 3H), 2.27 (d, J=0.5 Hz, 3H). $^{13}$C-NMR (125 MHz, CDCl$_3$) δ 139.2, 138.4, 136.9, 136.4, 135.8, 134.8, 125.9, 125.7, 123.9, 123.4, 123.4, 119.6, 15.7, 15.3. HRMS (EI+) Calculated for C$_{14}$H$_{12}$S$_3$ (M)$^+$: 276.0101; Found: 276.0104. IR (thin film, cm$^{-1}$) 2941, 2908, 1520, 1446, 1228, 1163, 1138, 1043, 991, 958, 907, 855, 831.

To form cross-coupled product 6k, 1-(4-(1-methyl-1H-indol-2-yl)phenyl)-ethanone, the general procedure was followed using 4-bromoacetophenone (0.199 g, 1.00 mmol), MIDA boronate 2j (0.429 g, 1.50 mmol), and K$_3$PO$_4$.H$_2$O (1.727 g, 7.50 mmol). The product was eluted with hexanes:EtOAc (100:0→70:30) to afford 6k as a pale yellow solid (0.247 g, 99%). TLC (hexanes:EtOAc 4:1): $R_f$=0.25, visualized by UV (254 and 280 nm). $^1$H-NMR (500 MHz, CDCl$_3$) δ 8.07 (d, J=8.5 Hz, 2H), 7.70 (d, J=7.5 Hz, 1H), 7.63 (d, J=8.0 Hz, 2H), 7.41 (d, J=8.0 Hz, 1H), 7.33 (t, J=7.0 Hz, 1H), 7.22 (t, J=8.0 Hz, 1H), 6.70 (s, 1H), 3.78 (s, 3H), 2.67 (s, 3H). $^{13}$C-NMR (125 MHz, CDCl$_3$) δ 197.4, 140.0, 138.8, 137.2, 135.8, 128.9, 128.4, 127.7, 122.2, 120.6, 120.0, 109.7, 102.8, 31.3, 26.5. HRMS (ESI+) Calculated for C$_{17}$H$_{16}$NO (M+H)$^+$: 250.1232; Found: 250.1224. IR (thin film, cm$^{-1}$) 3076, 3054, 3025, 2996, 2954, 1784, 1675, 1602, 1464, 1409, 1357, 1316, 1273, 1243, 1210, 1167, 1114, 1099, 1020, 1005, 957, 932, 852, 839.

To form cross-coupled product 6l, 2-(4-methoxyphenyl)-1-methyl-1H-indole, the general procedure was followed using 4-bromoanisole (0.199 g, 1.00 mmol), MIDA boronate 2j (0.429 g, 1.50 mmol), and K$_3$PO$_4$.H$_2$O (1.727 g, 7.50 mmol). The product was eluted with hexanes:EtOAc (100:0→90:10). The isolated white solid was subjected to flash chromatography on C$_{18}$ silica gel (MeCN:H$_2$O 50:50→40:60) to afford 6l as a pale yellow solid (0.234 g, 99%). TLC (hexanes:EtOAc 4:1): $R_f$=0.53, visualized by UV (254 nm). $^1$H-NMR (500 MHz, CDCl$_3$) δ 7.61 (d, J=8.0 Hz, 1H), 7.40 (d, J=8.0 Hz, 2H), 7.32 (d, J=8.0 Hz, 1H), 7.22 (t, J=7.5 Hz, 1H), 7.12 (t, J=7.5, 1H), 6.97 (d, J=8.0 Hz, 2H), 6.49 (s, 1H), 3.82 (s, 3H), 3.68 (s, 3H). $^{13}$C-NMR (125 MHz, CDCl$_3$) δ 159.3, 141.3, 138.1, 130.5, 127.9, 125.1, 121.3, 120.2, 119.7, 113.9, 109.5, 100.9, 55.2, 31.0. HRMS (ESI+) Calculated for C$_{16}$H$_{16}$NO (M+H)$^+$: 238.1232; Found: 238.1237. IR (thin film, cm$^{-1}$) 3050, 2937, 1609, 1549, 1495, 1464, 1337, 1288, 1245, 1176, 1109, 1035, 1001, 840.

To form cross-coupled product 6m, 1-methyl-2-p-tolyl-1H-indole, the general procedure was followed using 4-chlorotoluene (0.127 g, 1.00 mmol), MIDA boronate 2j (0.431 g, 1.51 mmol), and K$_3$PO$_4$.H$_2$O (1.734 g, 7.53 mmol). The crude residue was subjected to flash chromatography on C$_{18}$ silica gel (MeCN:H$_2$O 95:5→5:95). The resulting pale yellow solid was eluted with hexanes through a plug of SiO$_2$ to afford 6m as a colorless solid (0.201 g, 91%). TLC (hexanes): $R_f$=0.26, visualized by UV (254 nm) and KMnO$_4$. $^1$H-NMR (500 MHz, CDCl$_3$) δ 7.61 (d, J=7.5 Hz, 1H), 7.36 (d, J=8 Hz, 2H), 7.30 (d, J=8 Hz, 1H), 7.20-7.23 (m, 3H), 7.12 (t, J=7.5 Hz, 1H), 6.51 (s, 1H), 3.66 (s, 3H), 2.38 (s, 3H). $^{13}$C-NMR (125 MHz, CDCl$_3$) δ 141.6, 138.2, 137.6, 129.8, 129.1, 129.1, 127.9, 121.4, 120.3, 119.7, 109.5, 101.2, 31.0, 21.2. HRMS (ESI+) Calculated for C$_{16}$H$_{16}$N (M+H)$^+$: 222.1283; Found: 222.1279. IR (thin film, cm$^{-1}$) 3042, 2966, 2916, 1924, 1608, 1542, 1499, 1463, 1432, 1410, 1383, 1367, 1339, 1317, 1240, 1218, 1166, 1148, 1133, 1114, 1099, 1007, 918, 831.

To form cross-coupled product 6n, 1-(4-vinylphenyl)ethanone, the general procedure was followed using 4-bromoacetophenone (0.201 g, 1.01 mmol), MIDA boronate 2g (0.277 g, 1.51 mmol), and K$_3$PO$_4$.H$_2$O (1.743 g, 7.57 mmol). The product was eluted with hexanes:EtOAc 6:1 to afford 6n as a colorless solid (0.140 g, 95%). TLC (hexanes:EtOAc 6:1): $R_f$=0.33, visualized by UV (254 nm) and KMnO$_4$. $^1$H-NMR (500 MHz, CDCl$_3$) δ 7.92 (d, J=8.5 Hz, 2H), 7.47 (d, J=8.5 Hz, 2H), 6.75 (dd, J=17.5, 11 Hz, 1H), 5.87 (dd, J=17.5, 0.5 Hz, 1H), 5.39 (dd, J=10.5, 0.5 Hz, 1H), 2.59 (s, 3H). $^{13}$C-NMR (125 MHz, CDCl$_3$) δ 197.5, 142.0, 136.2, 135.8, 128.6, 126.2, 116.7, 26.5. HRMS (CI+) Calculated for C$_{10}$H$_{11}$O (M+H)$^+$: 147.0810; Found: 147.0808. IR (thin film, cm$^{-1}$) 2920, 1685, 1607, 1413, 1358, 1303, 1268, 1182, 1073, 1014, 957, 831.

This synthesis was modified by using a different catalyst stock of Pd(PPh$_3$)$_4$ (0.02 M in THF). Otherwise, the general procedure was followed using 4-bromo-acetophenone (0.200 g, 1.00 mmol), MIDA boronate 2g (0.277 g, 1.51 mmol), and K$_3$PO$_4$.H$_2$O (1.735 g, 7.53 mmol). The product was eluted with hexanes:EtOAc 6:1 to afford 6n as a colorless solid (0.136 g, 93%).

This synthesis was also performed with a different organohalide. The general procedure was followed using 2-chloroacetophenone (0.155 g, 1.00 mmol), MIDA boronate 2g (0.275 g, 1.50 mmol), and K$_3$PO$_4$.H$_2$O (7.727 g, 7.50 mmol). The product was eluted with hexanes:Et$_2$O (100:0→80:20) to afford 6n as a colorless solid (0.141 g, 97%).

To form cross-coupled product 6o, 1-methoxy-4-vinylbenzene, the general procedure was followed using 4-bromoanisole (0.187 g, 1.00 mmol), MIDA boronate 2g (0.275 g, 1.50 mmol), and K$_3$PO$_4$.H$_2$O (7.51 g, 7.51 mmol). All rotary evaporation was performed at 0° C. The product was purified by passage through a plug of silica gel with CH$_2$Cl$_2$ to afford 6o as a colorless liquid (0.124 g, 92%). TLC (hexanes:EtOAc 6:1): R$_f$=0.51, visualized by UV (254 nm) and KMnO$_4$. $^1$H-NMR (500 MHz, CDCl$_3$) δ 7.38 (d, J=8.5 Hz, 2H), 6.89 (d, J=9.0, 2H), 6.70 (dd, J=18, 11 Hz, 1H), 5.64 (d, J=18, 1H), 5.16 (d, J=11, 1H), 3.83 (s, 3H). $^{13}$C-NMR (125 MHz, CDCl$_3$) δ 159.3, 136.2, 130.4, 127.3, 113.8, 111.5, 55.2. HRMS (EI+) Calculated for C$_9$H$_{10}$O (M)$^+$: 134.0732; Found: 134.0731. IR (thin film, cm$^{-1}$) 3086, 3003, 2955, 2934, 2836, 2060, 1885, 1811, 1734, 1628, 1607, 1575, 1511, 1463, 1442, 1408, 1320, 1301, 1248, 1174, 1114, 139, 990, 968, 956, 901, 834, 815.

To form cross-coupled product 6p, 2-vinylnaphthalene, the general procedure was followed using 2-chloronapthalene (0.163 g, 1.00 mmol), MIDA boronate 2g (0.277 g, 1.51 mmol), and K$_3$PO$_4$.H$_2$O (7.727 g, 7.50 mmol). The product was eluted with hexanes to afford 6p as a colorless solid (0.128 g, 84%, corrected for 10% residual 2-chloronaphthalene). TLC (hexanes): R$_f$=0.51, visualized by UV (254 nm). $^1$H-NMR (500 MHz, CDCl$_3$) δ 7.89-7.92 (m, 3H), 7.86 (s, 1H), 7.76 (dd, J=8.5, 2 Hz, 1H), 7.57 (m, 2H), 7.01 (dd, J=17.5, 11 Hz, 1H), 6.01 (d, J=17.5 Hz, 1H), 5.47 (d, J=11 Hz, 1H). $^{13}$C-NMR (125 MHz, CDCl$_3$) δ 136.9, 134.9, 133.5, 133.1, 128.1, 128.0, 127.6, 126.4, 126.2, 125.9, 123.1, 114.1. HRMS (EI+) Calculated for C$_{12}$H$_{10}$ (M)$^+$: 154.0783; Found: 154.0784. IR (thin film, cm$^{-1}$) 3084, 3050, 2971, 2924, 1363, 1217, 991, 965, 949, 895, 860, 821.

To form cross-coupled product 6q, 1-(4-cyclopropylphenyl)ethanone, the general procedure was followed using 4-bromoacetophenone (0.200 g, 1.00 mmol), cyclopropyl MIDA boronate ester (0.298 g, 1.51 mmol), and K$_3$PO$_4$.H$_2$O (1.739 g, 7.55 mmol). However, for this reaction, a catalyst stock of PdCl$_2$dppf.CH$_2$Cl$_2$ (0.041 g, 0.05 mmol) and THF (10 mL) was used, and the reaction was maintained at 85° C. for 24 h. The product was eluted with hexanes:EtOAc 6:1 to afford 6q as a colorless solid (0.150 g, 93%). TLC (hexanes: EtOAc 6:1): R$_f$=0.34, visualized by UV (254 nm) and KMnO$_4$. $^1$H-NMR (500 MHz, CDCl$_3$) δ 7.84 (d, J=8.5 Hz, 2H), 7.11 (d, J=8.5 Hz, 2H), 2.55 (s, 3H), 1.93 (m, 1H), 1.05 (m, 2H), 0.77 (m, 2H). $^{13}$C-NMR (125 MHz, CDCl$_3$) δ 197.3, 150.1, 134.3, 128.2, 125.2, 26.2, 15.5, 10.2. HRMS (CI+) Calculated for C$_{11}$H$_{13}$O (M+H)$^+$: 161.0967; Found: 161.0964. IR (thin film, cm$^{-1}$) 3081, 3005, 1679, 1606, 1413, 1359, 1270, 1186, 1045, 1014, 958, 900, 822, 654.

While various embodiments of the invention have been described, it will be apparent to those of ordinary skill in the art that other embodiments and implementations are possible within the scope of the invention. Accordingly, the invention is not to be restricted except in light of the attached claims and their equivalents.

REFERENCES

Aoyagi, Y; Inoue, A.; Koizumi, I.; Hashimoto, R.; Tokunaga, K.; Gohma, K.; Komatsu, J.; Sekine, K.; Miyafuji, A.; Kunoh, J.; Honma, R.; Akita, Y.; Ohta, A. *Heterocycles* 1992, 33, 257-272.
Ballmer, S. G.; Gillis, E. P.; Burke, M. D. *Org. Syn.*, in press.
Barder, T. E.; Walker, S. D.; Martinelli, J. R.; Buchwald, S. L. *J. Am. Chem. Soc.* 2005, 127, 4685-4696.
Billingsley, K.; Buchwald, S. L. *J. Am. Chem. Soc.* 2007, 129, 3358-3366.
Billingsley, K. L.; Buchwald, S. L 2008, 47, 4695-4698.
Brown, *JACS*, 1972, 94, 4370-4371.
Brown, *J. Org. Chem.* 1982, 47, 3808-3810.
Brown, H. C. et al. *Organometallics* 1983, 2, 1316-1319.
Brown, *Organometallics* 1984, 3, 1392-1395.
Cammidge, A. N. et al. *Organic Letters* 2006, 8, 4071-4074.
Conlon, D. A; Crivello, J. V.; Lee, J. L.; O'Brien, M. J. *Macromolecules*, 1989, 22, 509-516.
Cui, Y.; Tang, X-B.; Shao, C-X.; Li, J-T.; Sun, W-H. *Chin. J. Chem.* 2005, 23, 589-595.
Deng, X.; Mayeux, A.; Cai, C. *J. Org. Chem.* 2002, 67, 5279-5283.
Gazit, A.; App, H.; McMahon, G.; Chen, J.; Levitzki, A.; Bohmer, F. D. *J. Med. Chem.* 1996, 39, 2170-2177.
Gillis, E. P.; Burke, M. D. *J. Am. Chem. Soc.* 2007, 129, 6716-6717.
Gronowitz, S.; Peters, D. *Heterocycles* 1990, 30, 645.
Hall, D. G. Boronic Acids, Wiley-VCH, Germany, 2005, 3-14.
Hashmi, A. S. K.; Salathe, Wolfgang, F. *Chem. Eur. J.* 2006, 12, 6991-6996.
Hitchcock, S. A.; Mayhugh, D. R.; Gregory, G. S. *Tetrahedron Lett.* 1995, 36, 9085-9088.
Hohn, E.; Pietruszka, J. *Adv. Synth. Catal.* 2004, 346, 863-866.
Holmes, D., et al. *Org. Lett.* 2006, 8, 1407-1410.
Hopfl, H., *J. Organomet. Chem.* 581, 129-149, 1999.
Hoye, T. R.; Eklov, B. M.; Voloshin, M. *Org. Lett.*, 2004, 6, 2567-2570.
Johnson, C. N.; Stemp, G.; Anand, N.; Stephen, S.C., Gallagher, T. *Synlett* 1998, 1025-1027.
Kang, S-K.; Ryu, H-C.; Choi, S-C. *Chem. Commun.* 1998, 1317-1318.
Kerins, F.; O'Shea, D. F. *J. Org. Chem.* 2002, 67, 4968-4971.
Kitamura, Y.; Sako, S.; Udzu, T.; Tsutsui, A.; Maegawa, T.; Monguchi, Y.; Hironao, S. *Chem. Commun.* 2007, 47, 5069-5071.
Lando, V. R.; Monteiro, A. L. *Org. Lett.*, 2003, 5, 2891-2894.
Lee, S. J.; Gray, K.C., Paek, J. S., Burke, M. D. *J. Am. Chem. Soc.* 2008, 130, 466-468.
Lemhadri, M.; Doucet, H.; Santelli, M. *Chem. Commun.* 2006, 36, 121-128.
Li, J.-H, Deng, C.-L. Xie, Y.-X. *Synthetic Comm.* 2007, 37, 2433-2448.
Lightfoot, A. P.; Twiddle, S. J. R.; Whiting, A. *SynLett* 2005, 3, 529-531.

Littke, A. F.; Dai, C.; Fu, G. C. *J. Am. Chem. Soc.* 2000, 122, 4020-4028.
Littke, A. F.; Schwarz, L.; Fu, G. C. *J. Am. Chem. Soc.* 2002, 124, 6343-6348.
Matteson, D. S. *J. Am. Chem. Soc.* 1960, 82, 4228-4233.
Matteson, D. S.; Majumdar, D. *J. Am. Chem. Soc.* 1980, 102, 7590-7591.
Messmore, B. W.; Hulvat, J. F.; Sone, E. D.; Stupp, S. I. *J Am. Chem. Soc.* 2004, 126, 14452-14458.
Miyaura, N.; Suzuki, A. *Chem. Rev.* 1995, 95, 2457-2483.
Miyaura et al. *J. Org. Chem.* 1995, 60, 7508-7510.
Miyaura et al. *Tet. Lett.* 1997, 38, 3447-3450.
Molander, G. A.; Biolatto, B. *J. Org. Chem.* 2003, 68, 4302-4314.
Molander, G. A.; Brown, A. R. *J. Org. Chem.* 2006, 71, 9681-9686.
Molander, G. A; Ellis, N. *Acc. Chem. Res.* 2007, 40, 275-286.
Nicolaou, K. C., et al. *Angew. Chem. Int. Ed.* 2005, 44, 4442.
Noguchi, H.; Hojo, K.; Suginome, M. *J. Am. Chem. Soc.* 2007, 129, 758-759.
O'Brien, C. J.; Kantchev, E. A. B.; Valente, C.; Hadei, N.; Chass, G. A.; Lough, A.; Hopkinson, A.; Organ, M. G. *Chem. Eur. J.* 2006, 12, 4743-4748.
Qin, Y. *JACS* 2002, 124, 12672-12673.
Qin, Y. *Macromolecules* 2004, 37, 7123-7131.
Soundararajan et al. *J. Org. Chem.* 1990, 55, 2274-2275.
Still, W.C.; Kahn, M.; Mitra, A.; *J. Org. Chem.* 1978, 43, 2923-2925.
Tyrrell, E.; Brookes, P. *Synthesis,* 2003, 4, 469-483.
Uno, B. E.; Gillis, E. P.; Burke, M. D. *Tetrahedron* 2009, 65, 3130-3138.
Wallace, D. J., Chen, C. *Tetrahedron Lett.* 2002, 43, 6987-6990.
Yamamoto, Y.; Takizawa, M.; Yu, X.-Q., Miyaura, N. *Angew. Chem. Int. Ed.* 2008, 47, 928-931.

What is claimed is:

1. A method of performing a chemical reaction, comprising:
reacting in a reaction mixture
a compound selected from the group consisting of an organohalide and an organo-pseudohalide, and
a protected organoboronic acid represented by formula (IV):

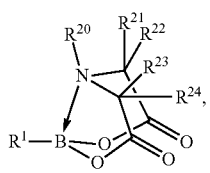

where
$R^1$ represents an organic group selected from the group consisting of a 2-pyrollyl group, a 2-indolyl group, and a vinyl group,
B represents boron having $sp^3$ hybridization,
$R^{20}$, $R^{21}$, $R^{22}$, $R^{23}$, and $R^{24}$ independently are selected from the group consisting of hydrogen and an organic group,
a corresponding unprotected organoboronic acid is unstable by the boronic acid neat stability test, and
the reaction mixture further comprises a base having a $pK_B$ of at least 1, and a palladium catalyst; and
forming a cross-coupled product in the reaction mixture.

2. The method of claim 1, where $R^1$ is selected from the group consisting of a 2-(N-butoxycarbonyl-pyrollyl) group and a 2-(N-phenylsulfonate-indolyl) group.

3. The method of claim 1, where $R^1$ represents a vinyl group.

4. The method of claim 1, where $R^{20}$ is an organic group.

5. The method of claim 4, further comprising forming the protected organoboronic acid represented by formula (IV) by reacting the corresponding unprotected boronic acid with a N-substituted imino-di-carboxylic acid.

6. The method of claim 4, where the protected organoboronic acid is represented by formula (V):

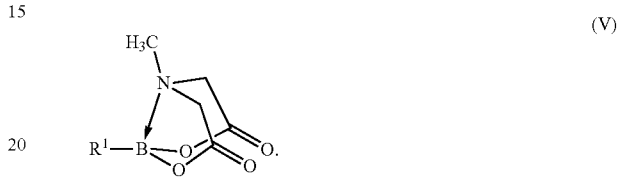

7. The method of claim 1, where the compound is selected from the group consisting of an aryl halide, a heteroaryl halide, an aryl pseudohalide, and a heteroaryl pseudohalide.

8. The method of claim 7, where the compound is selected from the group consisting of an unactivated aryl chloride and an unactivated heteroaryl chloride.

9. The method of claim 1, where the base has a $pK_B$ of at least 1.5.

10. The method of claim 1, where the base has a $pK_B$ of at least 3.

11. The method of claim 1, where the base comprises an anion selected from the group consisting of $[PO_4]^{3-}$, $[C_6H_5O]^-$, $[CO_3]^{2-}$, and $[HCO_3]^-$.

12. A method of performing a chemical reaction, comprising:
deprotecting in a reaction mixture a protected organoboronic acid represented by formula (IV):

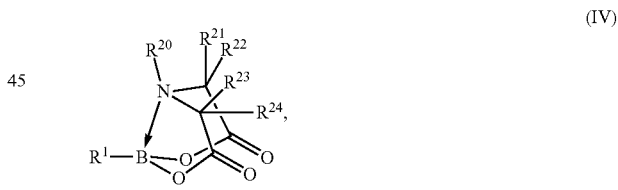

where
$R^1$ represents an organic group selected from the group consisting of a 2-pyrollyl group, a 2-indolyl group, and a vinyl group,
B represents boron having $sp^3$ hybridization,
$R^{20}$, $R^{21}$, $R^{22}$, $R^{23}$, and $R^{24}$ independently are selected from the group consisting of hydrogen and an organic group, and
the reaction mixture further comprises a base and a palladium catalyst, to form a corresponding unprotected organoboronic acid that is unstable by the boronic acid neat stability test;
reacting in the reaction mixture the unprotected organoboronic acid and a compound selected from the group consisting of an organohalide and an organopseudohalide; and
forming a cross-coupled product in the reaction mixture;

where the time required for at least 90% of the protected organoboronic acid to be deprotected in the reaction mixture is at least equal to the time required for 90% of the cross-coupled product to be formed in the reaction mixture.

* * * * *

UNITED STATES PATENT AND TRADEMARK OFFICE
CERTIFICATE OF CORRECTION

PATENT NO. : 9,328,102 B2
APPLICATION NO. : 14/686502
DATED : May 3, 2016
INVENTOR(S) : Martin D. Burke et al.

Page 1 of 1

It is certified that error appears in the above-identified patent and that said Letters Patent is hereby corrected as shown below:

In the Specification

At Column 1, Line 27, replace: "1-492576-510000-191788" with --GM080436--.

At Column 1, Line 27, replace: "may have" with --has--.

Signed and Sealed this
Twenty-fourth Day of July, 2018

Andrei Iancu
*Director of the United States Patent and Trademark Office*

UNITED STATES PATENT AND TRADEMARK OFFICE
CERTIFICATE OF CORRECTION

PATENT NO. : 9,328,102 B2
APPLICATION NO. : 14/686502
DATED : May 3, 2016
INVENTOR(S) : Martin D. Burke et al.

It is certified that error appears in the above-identified patent and that said Letters Patent is hereby corrected as shown below:

In the Specification

At Column 1, Line number 22, please delete:
"The subject matter of this application may have been funded in part under a research grant from the National Science Foundation under Grant Number Career 0747778, and under a research grant from the National Institutes of Health under Chemical Biology Interface Training Number 1-492576-510000-191788. The U.S. Government may have rights in this invention."

And replace with:
-- This invention was made with government support under 0747778 awarded by the National Science Foundation. The government has certain rights in the invention. --

Signed and Sealed this
Nineteenth Day of August, 2025

Coke Morgan Stewart
*Acting Director of the United States Patent and Trademark Office*